United States Patent [19]
Draper

[11] Patent Number: 6,132,966
[45] Date of Patent: *Oct. 17, 2000

[54] METHOD AND REAGENT FOR INHIBITING HEPATITIS C VIRUS REPLICATION

[75] Inventor: Kenneth G. Draper, Boulder, Colo.

[73] Assignee: Ribozyme Pharmaceuticals, Inc., Boulder, Colo.

[ * ] Notice: This patent is subject to a terminal disclaimer.

[21] Appl. No.: 09/064,156

[22] Filed: Apr. 21, 1998

Related U.S. Application Data

[63] Continuation of application No. 08/774,306, Dec. 23, 1996, Pat. No. 5,869,253, which is a continuation of application No. 08/182,968, Jan. 13, 1994, Pat. No. 5,610,054, which is a continuation-in-part of application No. 07/882,888, May 14, 1992, abandoned.

[51] Int. Cl.$^7$ .............................. C12Q 1/68; C07H 21/04; C12N 15/85; C12N 15/63

[52] U.S. Cl. ........................ 435/6; 435/91.31; 435/320.1; 435/325; 435/366; 536/23.1; 536/24.5

[58] Field of Search ............................ 435/6, 91.31, 375, 435/440, 325, 366, 320.1; 536/23.1, 23.2, 24.3, 24.5; 514/44; 800/13

[56] References Cited

U.S. PATENT DOCUMENTS

| | | | |
|---|---|---|---|
| 4,987,071 | 1/1991 | Cech et al. | 435/91.31 |
| 5,298,612 | 3/1994 | Jennings et al. | 536/23.2 |

FOREIGN PATENT DOCUMENTS

| | | |
|---|---|---|
| 0 558 944 | 9/1993 | European Pat. Off. . |
| 91/04319 | 9/1990 | WIPO . |
| 91/10674 | 7/1991 | WIPO . |
| 91/15580 | 10/1991 | WIPO . |
| 92/01786 | 2/1992 | WIPO . |
| 92/03566 | 3/1992 | WIPO . |
| 92/06693 | 4/1992 | WIPO . |

OTHER PUBLICATIONS

Branch TIBS 23:45–50, Feb. 1998.
"Ribozymes," *U.S. Biochemicals Editorial comments* 16(2):1–5 (1989).
"RNAzyme Tet 1.0 Kit," *U.S. Biochemicals Editorial Comments* 16(2):8–9 (1989).
Baringa, "Ribozymes: Killing the Messenger," *Science* 262:1521–1514 (1993).
Cech, "Ribozymes and their Medical Implications," *JAMA* 260:3030–3034 (1988).
Choo et al., "Genetic organization and diversity of the hepatitis C virus," *Proc. Natl. Adac. Sci. USA* 88:2451 (1991).
Christoffersen et al., "Application of computational technologies to ribozyme botechnology products," *Journal of Molecular Structure (Theochem)* 311:273–284 (1994).
Dropulic et al., "Functional Characterization of a U5 Ribozyme: Intracellular Suppression of Human Immunodeficiency Virus Type I Expression," *Journal of Virology* 66:1432–1441 (1992).

Guerrier–Takada et al., "The RNA Moiety of Ribonuclease P Is the Catalytic Subunit of the Enzyme," *Cell* 35:849–857 (1983).
Hampel and Tritz, "RNA Catalytic Properties of the Minimum (–)sTRSV Sequence," *Biochemistry* 28:4929–4933 (1989).
Hampel et al., "'Hairpin' Catalytic RNA Model: Evidence for Helices and Sequence Requirement for Substrate RNA," *Nucleic Acids Research* 18:299–304 (1990).
Haseloff and Gerlack, "Simple RNA Enzymes with New and Highly Specific Endoribonuclease Activities," *Nature* 334:585–591 (1988).
He et al., "In Vitro cleavage of HPV16 E6 and E7 mRNA by designed ribozymes," *Chemical Abstracts* vol. 120, no.1 at abstract no.3342 (1994).
He et al., "In Vitro cleavage of HPV16 E6 and E7 mRNA by designed ribozymes," *FEBS Letters* 322:21–24 (1993).
Jeffries and Symons, "A Catalytic 13–mer Ribozyme," *Nucleic Acids Research* 17:1371–1377 (1989).
Johnston and Hoth, "Present Status and Future Prospects for HIV Therapies," *Science* 260:1286–1293 (1993).
Kashani–Sabat et al., "Reversal of the Malignant Phenotype by an Anti–ras Ribozyme," *Antisense Research & Development* 2:3–15 (1992).
Kim and Cech, "Three–dimensional model of the active site of the self–splicing rRNA precursor of Tetrahymena," *Proc. Natl. Acad. Sci. USA* 84:8788 (1987).
Lu et al., "Ribozyme–mediated in vitro cleavage of transcripts arising from the major transforming genes of human papillomavirus type 16," *Cancer Gene Therapy* 1(4):267–277 (1994).
Mamone et al., "Design of Hammerhead Ribozymes Targeted to Sequences in HIV, HSV and the RAT ANF Gene," Abstract of Keystone, CO (May 27, 1992).
Martell et al., *J. Hepatol.* Suppl. 2, 13:551 (1991).
Okamoto et al., *Virology* 190:894 (1990).
Pavco et al., "Regulation of Self–Splicing Reactions by Antisense RNA," Abstract of Keystone, CO (May 27, 1992).
Perrotta and Been, "Cleavage of Oligoribonucleotides by a Ribozyme Derived from the Hepatitis δ Virus RNA Sequence," *Biochemistry* 31:16–21 (1992).
Rossi and Sarver, "RNA enzymes (ribozymes) as antiviral therapeutic agents," *TIBTECH* 8:179–183 (1990).
Rossi et al, "Ribozymes as Anti–HIV–1 Therapeutic Agents: Principles, Applications, and Problems," *Aids Research and Human Retroviruses* 8:183–189 (1992).
Rossi et al., "Ribozyme Mediated Intracellular Immunity to HIV–1 in CD4," *J. Cell Biochem.* Suppl 14A:D428 (1990).
Rossi et al., "Ribozymes as Anti–HIV–1 Therapeutic Agents: Principles, Applications, and Problems," *Aids Research and Human Retroviruses* 8:183–189 (1992).
Rossi et al., "Ribozymes as potential therapeutic agents," *Proc. Annu. Meeting Am. Assoc. Cancer Res.* 34:592–593 (1993).

(List continued on next page.)

*Primary Examiner*—George C. Elliott
*Assistant Examiner*—Andrew Wang

[57] ABSTRACT

An enzymatic RNA molecule which specifically cleaves RNA of a hepatitis C virus.

29 Claims, 1 Drawing Sheet

OTHER PUBLICATIONS

Rossi et al., "Ribozymes As Therapies For AIDS," *Annals of the New York Academy of Sciences* 606:184–200 (1990).

Sarver et al., "Ribozymes as Potential Anti–HIV–1 Therapeutic Agents" *Science* 247:1222–1225 (1990).

Stull and Szoka, "Antigene, Ribozyme and Aptamer Nucleic Acid Drugs: Progress and Prospects," *Pharmaceutical Research* 12:465–483 (1995).

Tanaka et al., "Molecular cloning of hepatitis C virus genome from a single Japanese carrier: sequence variation within the same individual and among infected individuals," *Virus Research* 23:39 (1992).

Tsukiyama–Kohara et al., "Internal Ribosome Entry Site Within Hepatitis C Virus RNA," *Journal of Virology* 66:1476–1483 (1992).

von Weizsacker et al., "Cleavage of Hepatitis B Virus RNA by Three Ribozymes Transcribed From a Single DNA Template," *Biochemical and Biophysical Research Communications* 189:743–748 (1992).

Weerasinghe et al., "Resistance to Human Immunodeficiency Virus Type 1 (HIV–1) Infection in Human CD4$^+$ Lymphocyte–Derived Cell Lines Conferred by Using Retroviral Vectors Expressing an HIV–1 RNA–Specific Ribozyme," *Journal of Virology* 65:5531–5534 (1994).

Wong–Staal, "Molecular targets for interference with viral replication," *International Conference on AIDS* 9(1):10 (1993).

Yoo et al., *Virology* 191:889 (1992).

METHOD AND REAGENT FOR INHIBITING HEPATITIS C VIRUS REPLICATION

This application is a continuation of 08/774,306 filed Dec. 23, 1996, now U.S. Pat. No. 5,869,253; which is a continuation of 08/182,968 filed Jan. 13, 1994, now U.S. Pat. No. 5,610,054; which is a continuation-in-part of Draper, entitled "Method and Reagent For Inhibiting Hepatitis C Virus Replication", filed May 14, 1992, assigned U.S. Ser. No. 07/882,888, now abandoned, the whole of which is hereby incorporated by reference herein.

BACKGROUND OF THE INVENTION

This invention relates to reagents useful as inhibitors of hepatitis C virus (HCV) replication and gene expression.

The following is a discussion of relevant art, none of which is admitted to be prior art to the pending claims.

The Hepatitis C virus group is responsible for most cases of non-A, non-B hepatitis. Although non-A, non-B hepatitis may be caused by many different viruses, the principal cause is HCV. The infection is transmitted through blood transfusions (25–50% of hemophiliacs have chronic hepatitis), percutaneous infusion from illicit drug usage (25–50% of all drug users have non-A, non-B hepatitis), renal organ transplant (where most late mortality is due to non-A, non-B hepatitis), and maternal-neonatal transfer. Up to 20% of sporadic outbreaks of hepatitis are caused by HCV.

The association of hepatitis C virus in posttransfusion hepatitis (>95% of the cases) and the subsequent observation that infection with this virus, more so than with hepatitis B virus, correlates strongly with the development of hepatocellular carcinoma and liver cirrhosis has led to intense study of the molecular biology of the viral genes.

Hepatitis C virus (HCV) is a positive-stranded, enveloped virus which is evolutionarily related to the flaviviruses and pestiviruses. The HCV genome consists of a 5' untranslated region (5' UTR), a long open reading frame of between 9030 and 9099 nucleotides and a 3' UTR. The 3' end of the genome has been reported to contain a short stretch of poly(A) in type I strains, but this has not been confirmed in type II, III or IV strains. It has been reported that sequences in the 5' UTR exhibit negative translational control over viral gene expression, but the major regulation of HCV gene expression comes from the proteolytic cleavages of the polyprotein. Various proteolytic cleavages of the polyprotein are essential for the efficient expression of replication-associated viral proteins after translation. The resultant replicase proteins interact with a region of between 27 and 45 nucleotides in the 3' UTR which functions as a structural cue for the initiation of viral genomic replication.

Cleavage of the polyprotein of HCV uses both cellular and virally-encoded proteases and generates at least nine proteins. A tenth viral protein (a second protease) has been reported to be generated by alternative cleavage of the polyprotein, but has not been confirmed. Confirmed virally-encoded proteins can be classified as structural or non-structural proteins. The structural proteins of the virus are the C protein (22 kD), E glycoprotein (35 kD) and the E2/NS1 glycoprotein (58 kD). The non-structural proteins include the NS2 (53 kD), NS3 (70 kD), NS4a (8 kD), NS4b (27 kD), NS5a (58 kD) and NS5b (68 kD).

The C protein is a hydrophobic protein which constitutes the core structural component of the viral particle and may play a role in localizing the viral particle to the cellular membrane. There is also evidence from transient assays that the core protein may function as a transactivator of gene expression. This protein is essential to viral replication and appears to be highly conserved at the nucletide level of homology among known types of HCV.

The envelope proteins are necessary for viral replication but their nucleotide (and amino acid) sequences diverge significantly between types of HCV. The NS3 protein functions as the major viral protease and mutations in this protein lead to inactivation of viral replication by inhibiting the processing of the polyprotein. The nucleotide sequence of the NS3 region is highly conserved among viral isolates.

The level of infidelity exhibited by the HCV RNA replicase has been indirectly quantified by assessing the sequential appearance of nucleotide substitutions in the genomes of HCV samples obtained from the same patient. These studies suggested that the nucleotide divergence was minimal but it may have been an underestimate of the actual infidelity of the replicase because the recovered samples were actually pre-selected by growth in the patient. Unacceptible substitutions would have been lost during the outgrowth of the virus.

The replication of HCV in hepatocytes is integrally intertwined with the replication of other hepatitis viruses. Although hepatitis delta virus (HDV) is quite distinct from HCV, the life cycles of the two viruses can be interdependent. Normally HDV depends upon the replication of Hepatitis B Virus (HBV) to supply capsid proteins and other functions necessary for the assembly of infectious HDV particles. Because HCV inhibits HBV and Hepatitis A virus (HAV) growth in co-infected cells, the replication of HCV can also inhibit the maturation of HDV. The use of HDV as a gene vector for treatment of HCV infections would not be influenced by this interference because gene expression of the HDV genome is apparently uninhibited by HCV.

SUMMARY OF THE INVENTION

The invention features novel enzymatic RNA molecules, or ribozymes, and methods for their use for inhibiting HCV replication. Such ribozymes can be used in a method for treatment of diseases caused by these related viruses in man and other animals, including other primates.

Ribozymes are RNA molecules having an enzymatic activity which is able to repeatedly cleave other separate RNA molecules in a nucleotide base sequence specific manner. Such enzymatic RNA molecules can be targeted to virtually any RNA transcript, and efficient cleavage achieved in vitro. Kim et al., 84 *Proc. Nat. Acad. of Sci. USA* 8788, 1987, Hazeloff et al., 234 *Nature* 585, 1988, Cech, 260 *JAMA* 3030, 1988, and Jefferies et al., 17 *Nucleic Acid Research* 1371, 1989.

Ribozymes act by first binding to a target RNA. Such binding occurs through the target RNA binding portion of a ribozyme which is held in close proximity to an enzymatic portion of the RNA which acts to cleave the target RNA. Thus, the ribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein. After a ribozyme has bound and cleaved its RNA target it is released from that RNA to search for another target and can repeatedly bind and cleave new targets.

The enzymatic nature of a ribozyme is advantageous over other technologies, such as antisense technology (where a nucleic acid molecule simply binds to. a nucleic acid target to block its translation) since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it is thought that the specificity of action of a ribozyme is greater than that of antisense oligonucleotide binding the same RNA site.

This class of chemical cleavers will exhibit a high degree of specificity for only the viral mRNA in infected cells. A ribozyme molecule targeted to a highly conserved sequence region will allow the treatment of many strains of human HCV with a single compound. No treatment exists which specifically attacks expression of the viral gene(s) of HCV. Current treatment protocols (interferon and ribavirin) consist of treating the symptoms of the disease, not the viral replication. Upon cessation of current treatment protocols, a rebound of disease ensues because the treatment does not impact the latency of the virus or actual viral replication. The cleavage of viral RNA offers a novel treatment which will reduce virus replication and establishment of latency in newly infected cells.

The methods of this invention can be used to treat human hepatitis C virus infections, which include both acute and chronic virus infection and HCV-induced hepatocyte transformation. The utility can be extended to other species of HCV which infect non-human animals, where such infections are of veterinary importance. Further, the utility may be extended to other members of the pestivirus and flavivirus families.

Treatment will occur at the time of active viral infection and will reduce virus loads in the infected cells and also disable viral replication. Ribozyme treatment may also be used as a means of creating defective genomes which can be used in vaccines.

Thus, in the first aspect the invention features an enzymatic RNA molecule (or ribozyme) which specifically cleaves HCV RNA.

Preferred cleavage sites are within regions required for viral replication, e.g., protein synthesis, such as the 5' non-translated region of the HCV genome. This region is believed to control the translation of viral proteins in a manner which is reminiscent of the cap independent translational control of picornaviruses. Disruption of this region in the RNA results in deficient protein synthesis as well as incomplete DNA synthesis (and inhibition of transcription from the defective genomes).

Alternative regions outside of the 5' non-translated region also make suitable targets of ribozyme-mediated inhibition of HCV replication. Such targets include the genomic regions which encode the viral structural protein, E2/NS1, and the regions encoding the nonstructural proteins, especially the NS3 protease and NS2/NS3 hybrid proteases. Selection of particular target regions will depend upon the secondary structure of the genome. To avoid the potential of viral escape from ribozyme therapy, by random base changes in the genomic RNA, targeting of multiple regions within the 5' UTR, or the C and NS3 genes is anticipated.

Multiple targeting will also minimize the ability of the virus to utilize point mutations for escape from immune surveillance. The phase variation which accompanies amino acid substitutions in the surface proteins (and result from point mutations in the genome of HCV) has been proposed to account for the viral persistence which is typical of HCV infections. Thus, two or more different ribozymes can be used in this invention for therapeutic treatment.

By "gene" is meant to refer to either the protein coding regions of the cognate mRNA, or any regulatory regions in the RNA which regulate synthesis of the protein or stability of the mRNA.

By "enzymatic RNA molecule" it is meant an RNA molecule which has complementarity in a substrate binding region to a specified gene target, and also has an enzymatic activity which is active to specifically cleave RNA in that target. That is, the enzymatic RNA molecule is able to intermolecularly cleave RNA and thereby inactivate a target RNA molecule. This complementarity functions to allow sufficient hybridization of the enzymatic RNA molecule to the target RNA to allow the cleavage to occur. 100% complementarity is preferred, but complementarity as low as 50–75% may also be useful in this invention. By "equivalent" RNA to HCV is meant to include those naturally occurring RNA molecules associated with viral caused diseases in various animals, including humans, and other primates. These viral RNAs have similar structures and equivalent genes to each other.

In preferred embodiments, the enzymatic RNA molecule is formed in a hammerhead motif, but may also be formed in the motif of a hairpin, hepatitis delta virus, group I intron or RNaseP RNA (in association with an RNA guide sequence). Examples of such hammerhead motifs are described by Rossi et al., 8 AIDS RESEARCH AND HUMA RETROVIRUSES 183, 1992, of hairpin motifs by Hampel et al., RNA CATALYST FOR CLEAVING SPECIFIC RNA SEQUENCES, filed Sep. 20, 1989, which is a continuation-in-part of U.S. Ser. No. 07/247,100 filed Sep. 20, 1988, Hampel and Tritz, 28 *Biochemistry* 4929, 1989 and Hampel et al., 18 *Nucleic Acids Research* 299, 1990, and an example of the hepatitis delta virus motif is described by Perrotta and Been, 31 *Biochemistry* 16, 1992, of the RNaseP motif by Guerrier-Takada et al., 35 *Cell* 849, 1983, and of the group I intron by Cech et al., U.S. Pat. No. 4,987,071. These specific motifs are not limiting in the invention and those skilled in the art will recognize that all that is important in an enzymatic RNA molecule of this invention is that it has a specific substrate binding site which is complementary to one or more of the target gene RNA regions, and that it have nucleotide sequences within or surrounding that substrate binding site which impart an RNA cleaving activity to the molecule.

In particularly preferred embodiments, the RNA which is cleaved by the ribozyme is in the 5' UTR of HCV genomic RNA or in the C protein or NS3 ORFs. Nucleotide numbers in the HCV genome are given to delineate the 5' ends of the target regions. Primary sequence data is taken from Tanaka et al, 23 *Virus Res.* 39, 1992. For comparison, the HCV sequence data of Choo et al 88 *Proc. Natl. Acad. Sci. USA* 2451 1991 was used.

TABLE 1

HCV mRNA target sequences.

| Nucleotide No. | Target Sequence[a] | Seq. ID. NO. |
|---|---|---|
| 27 | CGACACU C CACCAUA | Seq. ID. NO. 001 |
| 114 | GCAGCCU C CAGGACC | Seq. ID. NO. 002 |
| 128 | CCCCCCU C CCGGGAG | Seq. ID. NO. 003 |
| 148 | UAGUGGU C UGCGGAA | Seq. ID. NO. 004 |
| 165 | GGUGAGU A CACCGGA | Seq. ID. NO. 005 |
| 175 | CCGGAAU U GCCAGGA | Seq. ID. NO. 006 |
| 199 | CCUUUCU U GGAUCAA | Seq. ID. NO. 007 |
| 213 | ACCCGCU C AAUGCCU | Seq. ID. NO. 008 |
| 252 | GACUGCU A GCCGAGU | Seq. ID. NO. 009 |
| 260 | GCCGAGU A GUGUUGG | Seq. ID. NO. 010 |
| 265 | GUAGUGU U GGGUCGC | Seq. ID. NO. 011 |
| 270 | GUUGGGU C GCGAAAG | Seq. ID. NO. 012 |
| 288 | UUGUGGU A CUGCCUG | Seq. ID. NO. 013 |
| 298 | GCCUGAU A GGGUGCU | Seq. ID. NO. 014 |
| 306 | GGGUGCU U GCGAGUG | Seq. ID. NO. 015 |
| 325 | GGGAGGU C UCGUAGA | Seq. ID. NO. 016 |
| 327 | GAGGUCU C GUAGACC | Seq. ID. NO. 017 |
| 330 | GUCUCGU A GACCGUG | Seq. ID. NO. 018 |
| 407 | AGGACGU C AAGUUCC | Seq. ID. NO. 019 |
| 412 | GUCAAGU U CCCGGGC | Seq. ID. NO. 020 |
| 413 | UCAAGUU C CCGGGCG | Seq. ID. NO. 021 |
| 426 | CGGUGGU C AGAUCGU | Seq. ID. NO. 022 |
| 472 | CCCACGU U GGGUGUG | Seq. ID. NO. 023 |
| 489 | CGCGACU A GGAAGAC | Seq. ID. NO. 024 |
| 498 | GAAGACU U CCGAACG | Seq. ID. NO. 025 |
| 499 | AAGACUU C CGAACGG | Seq. ID. NO. 026 |
| 508 | GAACGGU C GCAACCU | Seq. ID. NO. 027 |
| 534 | ACAACCU A UCCCCAA | Seq. ID. NO. 028 |
| 536 | AACCUAU C CCCAAGG | Seq. ID. NO. 029 |
| 546 | CAAGGCU C GCCGACC | Seq. ID. NO. 030 |
| 561 | CGAGGGU A GGGCCUG | Seq. ID. NO. 031 |
| 573 | CUGGGCU U AGCCUGG | Seq. ID. NO. 032 |
| 583 | CCUGGGU A CCCUUGG | Seq. ID. NO. 033 |
| 588 | GUACCCU U GGCCCCU | Seq. ID. NO. 034 |
| 596 | GGCCCCU C UAUGGCA | Seq. ID. NO. 035 |
| 598 | CCCCUCU A UGGCAAU | Seq. ID. NO. 036 |
| 632 | GAUGGCU C CUGUCAC | Seq. ID. NO. 037 |
| 637 | CUCCUGU C ACCCCGC | Seq. ID. NO. 038 |
| 649 | CGCGGCU C CCGGCCU | Seq. ID. NO. 039 |
| 657 | CCGGCCU A GUUGGGG | Seq. ID. NO. 040 |
| 660 | GCCUAGU U GGGGCCC | Seq. ID. NO. 041 |
| 696 | GCGCAAU C UGGGUAA | Seq. ID. NO. 042 |
| 707 | GUAAGGU C AUCGAUA | Seq. ID. NO. 043 |
| 710 | AGGUCAU C GAUACCC | Seq. ID. NO. 044 |
| 714 | CAUCGAU A CCCUCAC | Seq. ID. NO. 045 |
| 730 | UGCGGCU U CGCCGAC | Seq. ID. NO. 046 |
| 731 | GCGGCUU C GCCGACC | Seq. ID. NO. 047 |
| 748 | AUGGGGU A CAUUCCG | Seq. ID. NO. 048 |
| 752 | GGUACAU U CCGCUCG | Seq. ID. NO. 049 |
| 753 | GUACAUU C CGCUCGU | Seq. ID. NO. 050 |
| 758 | UUCCGCU C GUCGGCG | Seq. ID. NO. 051 |
| 761 | CGCUCGU C GGCGCCC | Seq. ID. NO. 052 |
| 773 | CCCCCCU A GGGGCG | Seq. ID. NO. 053 |
| 806 | AUGGUGU C CGGGUUC | Seq. ID. NO. 054 |
| 812 | UCCGGGU U CUGGAGG | Seq. ID. NO. 055 |
| 813 | CCGGGUU C UGGAGGA | Seq. ID. NO. 056 |
| 832 | GUGAACU A CGCAACA | Seq. ID. NO. 057 |
| 847 | GGGAACU U GCCCGGU | Seq. ID. NO. 058 |
| 855 | GCCCGGU U GCUCUUU | Seq. ID. NO. 059 |
| 859 | GGUUGCU C UUUCUCU | Seq. ID. NO. 060 |
| 982 | AUUGUGU A UGAGGCA | Seq. ID. NO. 061 |
| 1001 | GCAUGAU C AUGCAUA | Seq. ID. NO. 062 |
| 1022 | GGUGCGU A CCCUGCG | Seq. ID. NO. 063 |
| 1031 | CCUGCGU U CGGGAGA | Seq. ID. NO. 064 |
| 1032 | CUGCGUU C GGGAGAA | Seq. ID. NO. 065 |
| 1048 | AACGCCU C CGUUGU | Seq. ID. NO. 066 |
| 1053 | CUCCGU U GUUGGGU | Seq. ID. NO. 067 |
| 1056 | CCGUUGU U GGGUAGC | Seq. ID. NO. 068 |
| 1061 | GUUGGGU A GCGUCUCA | Seq. ID. NO. 069 |
| 1127 | GCCACGU C GACUUGC | Seq. ID. NO. 070 |
| 1132 | GUCGACU U GCUCGUU | Seq. ID. NO. 071 |
| 1136 | ACUUGCU C GUUGGGG | Seq. ID. NO. 072 |
| 1139 | UGCUCGU U GGGGCGG | Seq. ID. NO. 073 |
| 1153 | GCCGCUU U CUGUUCC | Seq. ID. NO. 074 |
| 1154 | CCGCUUU C UGUUCCG | Seq. ID. NO. 075 |
| 1158 | UUUCUGU U CCGCCAU | Seq. ID. NO. 076 |
| 1159 | UUCUGUU C CGCCAUG | Seq. ID. NO. 077 |
| 1168 | GCCAUGU A CGUGGGG | Seq. ID. NO. 078 |
| 1189 | UGCGGAU C CGUUUUC | Seq. ID. NO. 079 |
| 1193 | GAUCCGU U UUCUCG | Seq. ID. NO. 080 |
| 1194 | AUCCGUU U UCCUCGU | Seq. ID. NO. 081 |
| 1195 | UCCGUUU U CCUCGUC | Seq. ID. NO. 082 |
| 1196 | CCGUUUU C CUCGUCU | Seq. ID. NO. 083 |
| 1280 | GCCAUGU A UCAGGUC | Seq. ID. NO. 084 |
| 1282 | CAUGUAU C AGGUCAC | Seq. ID. NO. 085 |
| 1287 | AUCAGGU U ACCGCAU | Seq. ID. NO. 086 |
| 1373 | AAGCUGU C GUGGAUA | Seq. ID. NO. 087 |
| 1380 | CGUGGAU A UGGUGGC | Seq. ID. NO. 088 |
| 1406 | GGGGAGU C CUAGCGG | Seq. ID. NO. 089 |
| 1409 | GAGUCCU A GCGGGUG | Seq. ID. NO. 090 |
| 1418 | CGGGCCU U GCCUACU | Seq. ID. NO. 091 |
| 1423 | CUUGCCU A CUAUUCC | Seq. ID. NO. 092 |
| 1426 | GCCUACU A UUCCAUG | Seq. ID. NO. 093 |
| 1428 | CUACUAU U CCAUGGUG | Seq. ID. NO. 094 |
| 1429 | UACUAUU C CAUGGUG | Seq. ID. NO. 095 |
| 1727 | GCUCCAU C GACAAGU | Seq. ID. NO. 096 |
| 1735 | GACAAGU U CGCUCAG | Seq. ID. NO. 097 |
| 1736 | ACAAGUU C GCUCAGG | Seq. ID. NO. 098 |
| 1740 | GUUCGCU C AGGGAUG | Seq. ID. NO. 099 |
| 1757 | GCCCCAU C ACCUAUA | Seq. ID. NO. 100 |
| 1762 | AUCACCU A UACCGAG | Seq. ID. NC. 101 |
| 1795 | AGGCCUU A CUGCUGG | Seq. ID. NO. 102 |
| 1806 | CUGGCAU U ACGCACC | Seq. ID. NO. 103 |
| 1807 | UGGCAUU A CGCACCU | Seq. ID. NO. 104 |
| 1815 | CGCACCU C GGCAGUG | Seq. ID. NO. 105 |
| 1827 | GUGUGGU A UCGUACC | Seq. ID. NO. 106 |
| 1829 | GUGGUAU C GUACCUG | Seq. ID. NO. 107 |
| 1832 | GUAUCGU A CCUGCGU | Seq. ID. NO. 108 |
| 1840 | CCUGCGU C GCAGGUG | Seq. ID. NO. 109 |
| 1854 | GUGUGGU C CAGUGUA | Seq. ID. NO. 110 |
| 1883 | GCCCUGU U GUGGUGA | Seq. ID. NO. 111 |
| 1886 | CUGUUGU A GUGGGGA | Seq. ID. NO. 112 |
| 1902 | GACCGAU C GGUCCGG | Seq. ID. NO. 113 |
| 1906 | GAUCGGU C CGGUGCC | Seq. ID. NO. 114 |
| 1917 | UGCCCCU A CGUAUAA | Seq. ID. NO. 115 |
| 1921 | CCUACGU A UAACUGG | Seq. ID. NO. 116 |
| 1923 | UACGUAU A ACUGGGG | Seq. ID. NO. 117 |
| 1990 | AACUGGU U UGGCUGU | Seq. ID. NO. 118 |
| 1991 | ACUGGUU U GGCUGUA | Seq. ID. NO. 119 |
| 1998 | UGGCUGU A CAUGGAU | Seq. ID. NO. 120 |
| 2043 | GGGCCCU C CGUGCAA | Seq. ID. NO. 121 |
| 2054 | GCAACAU C GGGGGGG | Seq. ID. NO. 122 |
| 2063 | GGGGGGU C GGCAACC | Seq. ID. NO. 123 |
| 2072 | GCAACCU A CCUUGA | Seq. ID. NO. 124 |
| 2077 | CUCACCU U GACCUGC | Seq. ID. NO. 125 |
| 2121 | GGCCACU U ACACAAA | Seq. ID. NO. 126 |
| 2122 | GCCACUU A CACAAAA | Seq. ID. NO. 127 |
| 2137 | UGUGGCU C GGGCCA | Seq. ID. NO. 128 |
| 2149 | CCAUGGU U AACACCU | Seq. ID. NO. 129 |
| 2150 | CAUGGUU A ACACCUA | Seq. ID. NO. 130 |
| 2219 | UUACCAU C UUUAAGG | Seq. ID. NO. 131 |
| 2221 | ACCAUCU U UAAGGUU | Seq. ID. NO. 132 |
| 2261 | ACAGGCU U AGUGCUG | Seq. ID. NO. 133 |
| 2262 | CAGGCUU A GUGCUGC | Seq. ID. NO. 134 |
| 2295 | AGAGCGU U GCGACCU | Seq. ID. NO. 135 |
| 2320 | GACAGAU C GGAGCUC | Seq. ID. NO. 136 |
| 2327 | CGGAGCU C AGCCCGC | Seq. ID. NO. 137 |
| 2344 | CUGCUGU U CACGACA | Seq. ID. NO. 138 |
| 2417 | UCCACCU C CAUCAGA | Seq. ID. NO. 139 |
| 2421 | CCUCCAU C AGAACAU | Seq. ID. NO. 140 |
| 2429 | AGAACAU C GUGGACG | Seq. ID. NO. 141 |
| 2534 | CGCGCGU C UGUGCCU | Seq. ID. NO. 142 |
| 2585 | CCGCCCU A GAGAACC | Seq. ID. NO. 143 |
| 2600 | UGGUGGU C CUCAACG | Seq. ID. NO. 144 |
| 2603 | UGGUCCU C AACCGUG | Seq. ID. NO. 145 |
| 2671 | GCCUGGU A CAUCAAG | Seq. ID. NO. 146 |
| 2675 | GGUACAU C AAGGGCA | Seq. ID. NO. 147 |
| 2690 | GGCUGGU C CCUGGGG | Seq. ID. NO. 148 |
| 2704 | GCGGCAU A UGCUCUG | Seq. ID. NO. 149 |
| 2709 | AUAUGCU C UGUACGG | Seq. ID. NO. 150 |

TABLE 1-continued

HCV mRNA target sequences.

| Nucleotide No. | Target Sequence[a] | Seq. ID. NO. |
|---|---|---|
| 2713 | GCUCUGU A CGGCGUG | Seq. ID. NO. 151 |
| 2738 | UCCUGCU C CUGCUGG | Seq. ID. NO. 152 |
| 2763 | ACGGGCU U ACGCCAU | Seq. ID. NO. 153 |
| 2764 | CGGGCUU A CGCCAUG | Seq. ID. NO. 154 |
| 2878 | UGGUGGU U ACAAUAC | Seq. ID. NO. 155 |
| 2879 | GGUGGUU A CAAUACU | Seq. ID. NO. 156 |
| 2884 | UUACAAU A CUUUAUC | Seq. ID. NO. 157 |
| 2887 | CAAUACU U UAUCACC | Seq. ID. NO. 158 |
| 2888 | AAUACUU U AUCACCA | Seq. ID. NO. 159 |
| 2910 | GGCGCAU U UGUGCGU | Seq. ID. NO. 160 |
| 2911 | GCGCAUU U GUGCGUG | Seq. ID. NO. 161 |
| 2924 | UGUGGGU C CCCCCUC | Seq. ID. NO. 162 |
| 2931 | CCCCCCU C UCAAUGU | Seq. ID. NO. 163 |
| 2933 | CCCCUCU C AAUGUCC | Seq. ID. NO. 164 |
| 2939 | UCAAUGU C CGGGGGG | Seq. ID. NO. 165 |
| 2958 | CGAUGCU A UCAUCCU | Seq. ID. NO. 166 |
| 2960 | AUGCUAU C AUCCUCC | Seq. ID. NO. 167 |
| 2963 | CUAUCAU C CUCCUCA | Seq. ID. NO. 168 |
| 2966 | UCAUCCU C CUCACAU | Seq. ID. NO. 169 |
| 2969 | UCCUCCU C ACAUGUG | Seq. ID. NO. 170 |
| 3059 | CUGCCAU A ACUGCGA | Seq. ID. NO. 171 |
| 3138 | AGGCCAU U ACGUCCA | Seq. ID. NO. 172 |
| 3139 | GGCCAUU A CGUCCAA | Seq. ID. NO. 173 |
| 3143 | AUUACGU C CAAUGG | Seq. ID. NO. 174 |
| 3154 | AUGGCCU U CAUGAAG | Seq. ID. NO. 175 |
| 3155 | UGGCCUU C AUGAAGC | Seq. ID. NO. 176 |
| 3209 | CCCCGCU A CAGGAUU | Seq. ID. NO. 177 |
| 3216 | ACAGGAU U GGGCCCA | Seq. ID. NO. 178 |
| 3233 | CGGGCCU C CGAGACC | Seq. ID. NO. 179 |
| 3242 | GAGACCU U GCGGUGG | Seq. ID. NO. 180 |
| 3263 | AGCCCGU C GUCUUCU | Seq. ID. NO. 181 |
| 3266 | CCGUCGU C UUCUCUG | Seq. ID. NO. 182 |
| 3268 | GUCGUCU U CUCUGAC | Seq. ID. NC. 183 |
| 3290 | CCAAGAU C AUCACCU | Seq. ID. NO. 184 |
| 3293 | AGAUCAU C ACCUGGG | Seq. ID. NO. 185 |
| 3329 | GGGACAU C AUCUGGG | Seq. ID. NO. 186 |
| 3332 | ACAUCAU C UUGGGAC | Seq. ID. NO. 187 |
| 3334 | AUCAUCU U GGGACUG | Seq. ID. NO. 188 |
| 3347 | UGCCCGU C UCCGCCC | Seq. ID. NO. 189 |
| 3349 | CCCGUCU C CGCCCGA | Seq. ID. NO. 190 |
| 3371 | GGGAGAU A CUUCUGG | Seq. ID. NO. 191 |
| 3416 | GGCGACU C CUUGCCC | Seq. ID. NO. 192 |
| 3419 | GACUCCU U GCCCCCA | Seq. ID. NO. 193 |
| 3428 | CCCCCAU C ACGGCCU | Seq. ID. NO. 194 |
| 3482 | CUAGCCU U ACAGGCC | Seq. ID. NO. 195 |
| 3518 | GGGAGGU U CAAGUGG | Seq. ID. NO. 196 |
| 3519 | GGAGGUU C AAGUGGU | Seq. ID. NO. 197 |
| 3527 | AAGUGGU U UCCACCG | Seq. ID. NO. 198 |
| 3528 | AGUGGUU U CCACCGC | Seq. ID. NO. 199 |
| 3529 | GUGGUUU C CACCGCA | Seq. ID. NO. 200 |
| 3576 | UGUGUGU U GGACCGU | Seq. ID. NO. 201 |
| 3601 | GCCGGCU C AAAGACC | Seq. ID. NO. 202 |
| 3611 | AGACCCA A GCCGGCC | Seq. ID. NO. 203 |
| 3684 | UGCGCCU C CCGGGGC | Seq. ID. NO. 204 |
| 3696 | GGCGCGU U CCCUUAC | Seq. ID. NO. 205 |
| 3697 | GCGCGUU C CCUUACA | Seq. ID. NO. 206 |
| 3701 | GUUCCCU U ACACCAU | Seq. ID. NO. 207 |
| 3702 | UUCCCUU A CACCAUG | Seq. ID. NO. 208 |
| 3724 | GGUAGCU C GGACCUC | Seq. ID. NO. 209 |
| 3731 | CGGACCU C UAUCUGG | Seq. ID. NO. 210 |
| 3733 | GACCUCU A UCUGGUC | Seq. ID. NO. 211 |
| 3735 | CCUCUAU C UGGUCAC | Seq. ID. NO. 212 |
| 3740 | AUCUGGU C ACGAGAC | Seq. ID. NO. 213 |
| 3761 | ACGUCAU U CCGGUGC | Seq. ID. NO. 214 |
| 3762 | CGUCAUU C CGGUGCG | Seq. ID. NO. 215 |
| 3786 | UGACGGU C GGGGGAG | Seq. ID. NO. 216 |
| 3797 | GGAGCCU A CGUCCCC | Seq. ID. NO. 217 |
| 3802 | CUACGUC C CCCAGA | Seq. ID. NO. 218 |
| 3835 | GGCUCUU C GGGUGCC | Seq. ID. NO. 219 |
| 3851 | CACUGCU U GCUGCCUU | Seq. ID. NO. 220 |
| 3858 | CUGCCCU U CGGGGCA | Seq. ID. NO. 221 |
| 3859 | UGCCCUU C GGGGCAC | Seq. ID. NO. 222 |
| 3872 | ACGCUGU A GGCAUCU | Seq. ID. NO. 223 |
| 3878 | UAGGCAU C UUCCGGG | Seq. ID. NO. 224 |
| 3880 | GGCAUCU U CCGGGCU | Seq. ID. NO. 225 |

TABLE 1-continued

HCV mRNA target sequences.

| Nucleotide No. | Target Sequence[a] | Seq. ID. NO. |
|---|---|---|
| 3881 | GCAUCUU C CGGGCUG | Seq. ID. NO. 226 |
| 3908 | GGGGGGU U GCGAAGG | Seq. ID. NO. 227 |
| 4056 | GAGCACU A AAGUGCC | Seq. ID. NO. 228 |
| 4072 | GCUGCGU A CGCAGCC | Seq. ID. NO. 229 |
| 4087 | CAAGGGU A CAAGGUA | Seq. ID. NO. 230 |
| 4115 | CAUCUGU U GCCGCCA | Seq. ID. NO. 231 |
| 4175 | CCAACAU C AGAACUG | Seq. ID. NO. 232 |
| 4187 | CUGGGGU A AGGACCA | Seq. ID. NO. 233 |
| 4228 | UCCACCU U UGGUAAG | Seq. ID. NO. 234 |
| 4233 | CUAUGGU A AGUUCCU | Seq. ID. NO. 235 |
| 4237 | GGUAAGU U CCUUGCC | Seq. ID. NO. 236 |
| 4238 | GUAAGUU C CUUGCCG | Seq. ID. NO. 237 |
| 4241 | AGUUCCU U GCCGACG | Seq. ID. NO. 238 |
| 4280 | AUAUACU A AUAUGUG | Seq. ID. NO. 239 |
| 4283 | UCAUAAU A UGUGAUG | Seq. ID. NO. 240 |
| 4337 | GCACAGU C CUGGACC | Seq. ID. NO. 241 |
| 4370 | CGCGGCU C GUCUGC | Seq. ID. NO. 242 |
| 4373 | GGCUCGU C GUGCUCG | Seq. ID. NO. 243 |
| 4379 | UCGUGCU C GCCACCG | Seq. ID. NO. 244 |
| 4425 | CCCAAAU A UUGAGGA | Seq. ID. NO. 245 |
| 4444 | GCUCUGU C CAACACU | Seq. ID. NO. 246 |
| 4460 | GAGAGAU C CCCUUCU | Seq. ID. NO. 247 |
| 4481 | AGGCCAU C CCCCUCG | Seq. ID. NO. 248 |
| 4487 | UCCCCCU C GAGGCCA | Seq. ID. NO. 249 |
| 4496 | AGGCCAU C AAGGGGG | Seq. ID. NO. 250 |
| 4528 | UGCCACU C AAGAAG | Seq. ID. NO. 251 |
| 4577 | UCGGAAU C AAUGCCG | Seq. ID. NO. 252 |
| 4586 | AUGCCGU A GCGUAUU | Seq. ID. NO. 253 |
| 4591 | GUAGCGU A UUACCGG | Seq. ID. NO. 254 |
| 4593 | AGCGUAU U ACCGGGG | Seq. ID. NO. 255 |
| 4594 | GCGUAUU A CCGGGGU | Seq. ID. NO. 256 |
| 4616 | UGUCCGU C AUACCGA | Seq. ID. NO. 257 |
| 4619 | CCGUCAU A CCGACUA | Seq. ID. NO. 258 |
| 4626 | ACCGACU A GCGGAGA | Seq. ID. NO. 259 |
| 4672 | ACGGGCU A CACCGGU | Seq. ID. NO. 260 |
| 4697 | CGGUGAU C GACUGCA | Seq. ID. NO. 261 |
| 4789 | GCGGUGU C GCGCUCA | Seq. ID. NO. 262 |
| 4795 | UCGCGCU C ACAACGG | Seq. ID. NO. 263 |
| 4920 | CUGUGCU U GGUAUGA | Seq. ID. NO. 264 |
| 4924 | GCUUGGU A UGAGCUC | Seq. ID. NO. 265 |
| 4931 | AUGAGCU C ACGCCCG | Seq. ID. NO. 266 |
| 4947 | UGAGACU A CAGUCAG | Seq. ID. NO. 267 |
| 4952 | CUACAGU C AGGUUGC | Seq. ID. NO. 268 |
| 4957 | GUCAGGU U GCGGGGCU | Seq. ID. NO. 269 |
| 4965 | GCGGGCU U ACCUGAA | Seq. ID. NO. 270 |
| 4966 | CGGGCUU A CCUGAAU | Seq. ID. NO. 271 |
| 4974 | CCUGAAU A CACCAGG | Seq. ID. NO. 272 |
| 4984 | CCAGGGU U GCCCGUC | Seq. ID. NO. 273 |
| 4991 | UGCCCGU C UGCCAGG | Seq. ID. NO. 274 |
| 5004 | GGACCCU C UGGAGUU | Seq. ID. NO. 275 |
| 5102 | ACCUGGU A GCAUACC | Seq. ID. NO. 276 |
| 5107 | GUAGCAU A CCAAGCC | Seq. ID. NO. 277 |
| 5133 | CAGGGCU C AGGCUCC | Seq. ID. NO. 278 |
| 5218 | CUGCUGU A UAGGCUA | Seq. ID. NO. 279 |
| 5220 | GCUGUAU A GGCUAGG | Seq. ID. NO. 280 |
| 5306 | UGGAGGU C GUCACUA | Seq. ID. NO. 281 |
| 5309 | AGGUCGU C ACUAGCA | Seq. ID. NO. 282 |
| 5313 | CGUCACU A GCACCUG | Seq. ID. NO. 283 |
| 5330 | UGCUGGU A GGCGGAG | Seq. ID. NO. 284 |
| 5339 | GCGGAGU C CUUGCAG | Seq. ID. NO. 285 |
| 5342 | GAGUCCU U GCAGUCC | Seq. ID. NO. 286 |
| 5359 | GCCGCAU A UUGCCUG | Seq. ID. NO. 287 |
| 5361 | CGCAUAU U GCCUGAC | Seq. ID. NO. 288 |
| 5376 | AACCGGU A GUGUGGU | Seq. ID. NO. 289 |
| 5399 | GUAGGAU A UUUUGU | Seq. ID. NO. 290 |
| 5423 | CGGCUGU U GUUCCCG | Seq. ID. NO. 291 |
| 5426 | CUGUUGU U CCCGACA | Seq. ID. NO. 292 |
| 5427 | UGUUGUU C CGACAG | Seq. ID. NO. 293 |
| 5524 | GAGCAGU U CAAGCAG | Seq. ID. NO. 294 |
| 5525 | AGCAGUU C AAGCAGA | Seq. ID. NO. 295 |
| 5583 | CGCUGCU A CCGUGGU | Seq. ID. NO. 296 |
| 5596 | GUGGAGU C CAGGUGG | Seq. ID. NO. 297 |
| 5612 | GGGCCCU U GAGGCCU | Seq. ID. NO. 298 |
| 5620 | GAGGCCU U CUGGGCA | Seq. ID. NO. 299 |
| 5621 | AGGCCUU C UGGGCAA | Seq. ID. NO. 300 |

TABLE 1-continued

HCV mRNA target sequences.

| Nucleotide No. | Target Sequence[a] | Seq. ID. NO. |
|---|---|---|
| 5674 | GCAGGCU U AUCCACU | Seq. ID. NO. 301 |
| 5675 | CAGGCUU A UCCACUC | Seq. ID. NO. 302 |
| 5767 | CUCCUGU U CAACAUC | Seq. ID. NO. 303 |
| 5768 | UCCUGUU C AACAUCU | Seq. ID. NO. 304 |
| 5801 | CUCAACU C GCUCCUC | Seq. ID. NO. 305 |
| 5805 | ACUCGCU C CUCCCAG | Seq. ID. NO. 306 |
| 5821 | GCUGCUU C GGCCUUC | Seq. ID. NO. 307 |
| 5827 | UCGGCCU U CGUGGGC | Seq. ID. NO. 308 |
| 5828 | CGGCCUU C GUGGGCG | Seq. ID. NO. 309 |
| 5843 | CCGGCAU U GCCGUG | Seq. ID. NO. 310 |
| 5858 | CGGCCAU U GGCAGCA | Seq. ID. NO. 311 |
| 5867 | GCAGCAU A GGCCUUG | Seq. ID. NO. 312 |
| 5873 | UAGGCCU U GGGAAGG | Seq. ID. NO. 313 |
| 5905 | GCGGGCU A UGGAGCG | Seq. ID. NO. 314 |
| 5930 | GUGCACU C GUGGCUU | Seq. ID. NO. 315 |
| 5937 | CGUGGCU U UUAAGGU | Seq. ID. NO. 316 |
| 5938 | GUGGCUU U UAAGGUC | Seq. ID. NO. 317 |
| 5939 | UGGCUUU U AAGGUCA | Seq. ID. NC. 318 |
| 5940 | GGCUUUU A AGGUCAU | Seq. ID. NO. 319 |
| 5945 | UUAAGGU C AUGAGCG | Seq. ID. NO. 320 |
| 5965 | GCGCCCU C CGCCGAG | Seq. ID. NO. 321 |
| 5981 | ACCUGGU U AACUUGC | Seq. ID. NO. 322 |
| 5982 | CCUGGUU A ACUUGCU | Seq. ID. NO. 323 |
| 5990 | ACUUGCU C CCUGCCA | Seq. ID. NO. 324 |
| 6004 | AUCCUCU C CCCCGGC | Seq. ID. NO. 325 |
| 6020 | CCCUGGU C GUCGGGG | Seq. ID. NO. 326 |
| 6023 | UGGUCGU C GGGGUCG | Seq. ID. NO. 327 |
| 6029 | UCGGGGU C GUGUGUG | Seq. ID. NO. 328 |
| 6044 | CAGCAAU C CUGCGUC | Seq. ID. NO. 329 |
| 6051 | CCUGCGU C GGCACGU | Seq. ID. NO. 330 |
| 6106 | AUAGCGU U CGCUUCG | Seq. ID. NO. 331 |
| 6107 | UAGCGUU C GCUUCGC | Seq. ID. NO. 332 |
| 6111 | GUUCGCU U CGCGGGG | Seq. ID. NO. 333 |
| 6413 | ACGGCAU C AUGCAAA | Seq. ID. NO. 334 |
| 6574 | CCGAACU A UUCCAGG | Seq. ID. NO. 335 |
| 6576 | GAACUAU U CCAGGGC | Seq. ID. NO. 336 |
| 6577 | AACUAUU C CAGGGCG | Seq. ID. NO. 337 |
| 6637 | GGGGACU U CCACUAC | Seq. ID. NO. 338 |
| 6638 | GGGACUU C CACUACG | Seq. ID. NO. 339 |
| 6643 | UUCCACU A CGUGACG | Seq. ID. NO. 340 |
| 6671 | ACAACGU A AAAUGCC | Seq. ID. NO. 341 |
| 6703 | CCCGAAU U CUUCACC | Seq. ID. NO. 342 |
| 6704 | CCGAAUU C UUCACCG | Seq. ID. NO. 343 |
| 6706 | GAAUUCU U CACCGAA | Seq. ID. NO. 344 |
| 6707 | AAUUCUU C ACCGAAU | Seq. ID. NO. 345 |
| 6715 | ACCGAAU U GGACGGG | Seq. ID. NO. 346 |
| 6730 | GUGCGGU U GCACAGG | Seq. ID. NO. 347 |
| 6739 | CACAGGU A CGCUCCG | Seq. ID. NO. 348 |
| 6744 | GUACGCU C CGGCGUG | Seq. ID. NO. 349 |
| 6759 | CAGACCU C UCCUACG | Seq. ID. NO. 350 |
| 6761 | GACCUCU C CUACGGG | Seq. ID. NO. 351 |
| 6764 | CUCUCCU A CGGGAGG | Seq. ID. NO. 352 |
| 6776 | AGGAUGU C ACAUUCC | Seq. ID. NO. 353 |
| 6782 | UCACAUU C CAGGUCG | Seq. ID. NO. 354 |
| 6788 | UCCAGGU C GGGCUCA | Seq. ID. NO. 355 |
| 6794 | UCGGGCU C AACCAAU | Seq. ID. NO. 356 |
| 6802 | AACCAAU A CCUGGUU | Seq. ID. NO. 357 |
| 6809 | ACCUGGU U GGGUCAC | Seq. ID. NO. 358 |
| 6814 | GUUGGGU C ACAGCUC | Seq. ID. NO. 359 |
| 6821 | CACAGCU C CCAUGCG | Seq. ID. NO. 360 |
| 6906 | UAAACGU A AGCUGGAC | Seq. ID. NO. 361 |
| 6922 | AGGGGGU U UCCCCCC | Seq. ID. NO. 362 |
| 6924 | GGGGUCU C CCCCCUC | Seq. ID. NO. 363 |
| 6931 | CCCCCCU C CUUGGCC | Seq. ID. NO. 364 |
| 6934 | CCCUCCU U GGCCAGC | Seq. ID. NO. 365 |
| 6943 | GCCAGCU U UUCAGCU | Seq. ID. NO. 366 |
| 6958 | AGCCAAU U GUCUGCG | Seq. ID. NO. 367 |
| 6961 | CAAUUGU C UGCGCCU | Seq. ID. NO. 368 |
| 7034 | CCAACCU C CUGUGGC | Seq. ID. NO. 369 |
| 7118 | ACCCGCU U CGAGCGG | Seq. ID. NO. 370 |
| 7119 | CCCGCUU C GAGCGGA | Seq. ID. NO. 371 |
| 7145 | GGGAGU A UCCGUUG | Seq. ID. NO. 372 |
| 7195 | CCCGCGU U GCCCAUA | Seq. ID. NO. 373 |
| 7202 | UGCCCAU A UGGGCAC | Seq. ID. NO. 374 |
| 7218 | CCCGGAU U ACAACCC | Seq. ID. NO. 375 |
| 7219 | CCGGAUU A CAACCCU | Seq. ID. NO. 376 |
| 7234 | CCACUGU U AGAGUCC | Seq. ID. NO. 377 |
| 7235 | CACUGUU A GAGUCCU | Seq. ID. NO. 378 |
| 7251 | GAAAAGU C CGGACUA | Seq. ID. NO. 379 |
| 7258 | CCGGACU A CGUCCCU | Seq. ID. NO. 380 |
| 7262 | ACUACGU C CCUCCGG | Seq. ID. NO. 381 |
| 7266 | CGUCCCU C CGGCGGU | Seq. ID. NO. 382 |
| 7288 | UGCCCAU U GCCGCCU | Seq. ID. NO. 383 |
| 7296 | GCCGCCU A CCACGGG | Seq. ID. NO. 384 |
| 7354 | ACAGAGU C CACCGUG | Seq. ID. NO. 385 |
| 7386 | GCUGGCU A CUAAGAC | Seq. ID. NO. 386 |
| 7389 | GGCUACU A AGACUUU | Seq. ID. NO. 387 |
| 7395 | UAAGACU U UCGGCAG | Seq. ID. NO. 388 |
| 7396 | AAGACUU U CGGCAGC | Seq. ID. NO. 389 |
| 7397 | AGACUUU C GGCAGCU | Seq. ID. NO. 390 |
| 7411 | UCCGGAU C GUCGCC | Seq. ID. NO. 391 |
| 7414 | GGAUCGU C GGCCGUU | Seq. ID. NO. 392 |
| 7421 | CGGCCGU U GACAGCG | Seq. ID. NO. 393 |
| 7498 | UCGUACU C CUCCAUG | Seq. ID. NO. 394 |
| 7501 | UACUCCU C CAUGCCC | Seq. ID. NO. 395 |
| 7514 | CCCCCCU U GAGGGGG | Seq. ID. NO. 396 |
| 7539 | CCCGAU C UCAGCGA | Seq. ID. NO. 397 |
| 7541 | CUGAUCU C AGCGACG | Seq. ID. NO. 398 |
| 7552 | GACGGGU C UUGGUCU | Seq. ID. NO. 399 |
| 7554 | CGGGUCU U GGUCUAC | Seq. ID. NO. 400 |
| 7558 | UCUUGGU C UACCGUG | Seq. ID. NO. 401 |
| 7560 | UUGGUCU A CCGUGAG | Seq. ID. NO. 402 |
| 7589 | ACGACAU C GUCUGCU | Seq. ID. NO. 403 |
| 7592 | ACAUCGU C UGCUGCU | Seq. ID. NO. 404 |
| 7600 | UGCUGCU C AAUGUCC | Seq. ID. NO. 405 |
| 7606 | UCAAUGU C CUACACA | Seq. ID. NO. 406 |
| 7667 | UGCCCAU U AACGCGU | Seq. ID. NO. 407 |
| 7723 | ACAACAU A CCGCAGU | Seq. ID. NO. 408 |
| 7775 | UGCAAGU U CUGGACG | Seq. ID. NO. 409 |
| 7789 | GACCACU A CCGGGAC | Seq. ID. NO. 410 |
| 7839 | UAAGGCU U AACUUCU | Seq. ID. NO. 411 |
| 7847 | AACUUCU A UCCGUAG | Seq. ID. NO. 412 |
| 7849 | CUUCUAU C CGUAGAA | Seq. ID. NO. 413 |
| 7853 | UAUCCGU A GAAGAAG | Seq. ID. NO. 414 |
| 7894 | GCCAAAU C UAAAUUU | Seq. ID. NO. 415 |
| 7896 | CAAAUCU A AAUUUGG | Seq. ID. NO. 416 |
| 7900 | UCUAAAU U UGGCUAU | Seq. ID. NO. 417 |
| 7901 | CUAAAUU U GGCUAUG | Seq. ID. NO. 418 |
| 7906 | UUUGGCU A UGGGGCA | Seq. ID. NO. 419 |
| 7955 | ACCACAU C CGCUCCG | Seq. ID. NO. 420 |
| 7960 | AUCCGCU C CGUGGG | Seq. ID. NO. 421 |
| 8075 | CUCGCCU U AUCGUAU | Seq. ID. NO. 422 |
| 8076 | UCGCCUU A UCGUAUU | Seq. ID. NO. 423 |
| 8078 | GCCUUAU C GUAUUCC | Seq. ID. NO. 424 |
| 8170 | UCCUCGU A CGGAUUC | Seq. ID. NO. 425 |
| 8176 | UACGGAU U CCAGUAC | Seq. ID. NO. 426 |
| 8182 | UUCCAGU A CUCUCCU | Seq. ID. NO. 427 |
| 8187 | GUACUCU C CUGGGCA | Seq. ID. NO. 428 |
| 8201 | AGCGGGU U GAGUUCC | Seq. ID. NO. 429 |
| 8206 | GUUGAGU U CCUGGUG | Seq. ID. NO. 430 |
| 8207 | UUGAGUU C CUGGUGA | Seq. ID. NO. 431 |
| 8227 | UGGAAAU C AAAGAAA | Seq. ID. NO. 432 |
| 8357 | AGGCCAA A AAGUCGC | Seq. ID. NO. 433 |
| 8362 | AUAAAGU C GCUACG | Seq. ID. NO. 434 |
| 8366 | AGUCGCU C ACGGAGC | Seq. ID. NO. 435 |
| 8378 | AGCGGCU C UACAUCG | Seq. ID. NO. 436 |
| 8380 | CGGCUCU A CAUCG | Seq. ID. NO. 437 |
| 8384 | UCUACAU C GGGGGCC | Seq. ID. NO. 438 |
| 8424 | CUGCGGU U AUCGCCG | Seq. ID. NO. 439 |
| 8425 | UGCGGUU A UCGCCGU | Seq. ID. NO. 440 |
| 8427 | CGGUUAU C GCCGGUG | Seq. ID. NO. 441 |
| 8460 | GACGACU A GCUGCGG | Seq. ID. NO. 442 |
| 8508 | GGCCUGU C GAGCUGC | Seq. ID. NO. 443 |
| 8522 | CAAAGCU C CAGGACU | Seq. ID. NO. 444 |
| 8540 | CGAUGCU C GUAAAGC | Seq. ID. NO. 445 |
| 8558 | ACGACCU U GUCGUUA | Seq. ID. NO. 446 |
| 8561 | ACCUUGU C GUUAUCU | Seq. ID. NO. 447 |
| 8564 | UUGUCGU U AUCUGUG | Seq. ID. NO. 448 |
| 8638 | AGGUACU C UGCCCCC | Seq. ID. NO. 449 |
| 8671 | CCAGAAU A CGACUUG | Seq. ID. NO. 450 |

TABLE 1-continued

HCV mRNA target sequences.

| Nucleotide No. | Target Sequence[a] | Seq. ID. NO. |
|---|---|---|
| 8698 | UCAUGCU C CUCCAAC | Seq. ID. NO. 451 |
| 8701 | UGCUCCU C CAACGUG | Seq. ID. NO. 452 |
| 8728 | GACGCAU C CGGCAAA | Seq. ID. NO. 453 |
| 8774 | CCCCCCU U GCACGGG | Seq. ID. NO. 454 |
| 8842 | AUCAUGU A UGCGCCC | Seq. ID. NO. 455 |
| 8854 | CCCACCU U AUGGGCA | Seq. ID. NO. 456 |
| 8855 | CCACCUU A UGGGCAA | Seq. ID. NO. 457 |
| 8871 | GAUGAUU U UGAUGAC | Seq. ID. NO. 458 |
| 8880 | GAUGACU C ACUUCUU | Seq. ID. NO. 459 |
| 8931 | CCUGGAU U GUCAGAU | Seq. ID. NO. 460 |
| 8934 | GGAUUGU C AGAUCUA | Seq. ID. NO. 461 |
| 8939 | GUCAGAU C UACGGGG | Seq. ID. NO. 462 |
| 8941 | CAGAUCU A CGGGGCC | Seq. ID. NO. 463 |
| 9065 | CAUGCCU C AGGAAAC | Seq. ID. NO. 464 |
| 9074 | GGAAACU U GGGGUAC | Seq. ID. NO. 465 |
| 9080 | UUGGGGU A CCGCCCU | Seq. ID. NO. 466 |
| 9088 | CCGCCCU U GCGAGUC | Seq. ID. NO. 467 |
| 9095 | UGCGAGU C UGGAGAC | Seq. ID. NO. 468 |
| 9119 | GAAGUGU C CGCGCUA | Seq. ID. NO. 469 |
| 9126 | CCGCGCU A GGCUACU | Seq. ID. NO. 470 |
| 9131 | CUAGGCU A CUGUCCC | Seq. ID. NO. 471 |
| 9136 | CUACUGU C CCAAGGG | Seq. ID. NO. 472 |
| 9226 | GCCGCGU C CCAGCUG | Seq. ID. NO. 473 |
| 9238 | CUGGACU U GUCCAGC | Seq. ID. NO. 474 |
| 9241 | GACUUGU C CAGCUGG | Seq. ID. NO. 475 |
| 9250 | AGCUGGU U CGUUGCU | Seq. ID. NO. 476 |
| 9251 | GCUGGUU C GUUGCUG | Seq. ID. NO. 477 |
| 9254 | GGUUCGU U GCUGGUU | Seq. ID. NO. 478 |
| 9278 | GAGACAU A UAUCACA | Seq. ID. NO. 479 |
| 9280 | GACAUAU A UCACAGC | Seq. ID. NO. 480 |
| 9282 | CAUAUAU C ACAGCCU | Seq. ID. NO. 481 |
| 9292 | AGCCUGU C UCGUGCC | Seq. ID. NO. 482 |
| 9326 | GGUGCCU A CUCCUAC | Seq. ID. NO. 483 |
| 9329 | GCCUACU C CUACUUU | Seq. ID. NO. 484 |
| 9332 | UACUCCU A CUUUCCG | Seq. ID. NO. 485 |
| 9335 | UCCUACU U UCCGUAG | Seq. ID. NO. 486 |
| 9336 | CCUACUU U CCGUAGG | Seq. ID. NO. 487 |
| 9337 | CUACUUU C CGUAGGG | Seq. ID. NO. 488 |
| 9341 | UUUCCGU A GGGGUAG | Seq. ID. NO. 489 |
| 9347 | UAGGGGU A GGCAUCU | Seq. ID. NO. 490 |
| 9353 | UAGGCAU C UACCUGC | Seq. ID. NO. 491 |
| 9355 | GGCAUCU A CCUGCUC | Seq. ID. NO. 492 |
| 9362 | ACCUGCU C CCCAACC | Seq. ID. NO. 493 |
| 9385 | GGGAGCU A AUCACUC | Seq. ID. NO. 494 |
| 9388 | AGCUAAU C ACUCCAG | Seq. ID. NO. 495 |
| 9392 | AAUCACU C CAGGCCA | Seq. ID. NO. 496 |
| 9402 | GGCCAAU A GGCCAUC | Seq. ID. NO. 497 |

[a]Sequences which exhibit perfect homology between the two genomes are highlighted in bold face type.

Methods for preparation of ribozymes useful in this invention are generally described by Draper, entitled, "Method and Reagent For Treatment of Arthritic Conditions", filed Nov. 12, 1993, and assigned U.S. Ser. No. 08/152,487, the whole of which is hereby incorporated by reference herein.

In a second related aspect, the invention features a mammalian cell which includes an enzymatic RNA molecule as described above. Preferably, the mammalian cell is a human or other primate cell.

In a third related aspect, the invention features an expression vector which includes nucleic acid encoding the enzymatic RNA molecules described above, located in the vector, e.g., in a manner which allows expression of that enzymatic RNA molecule within a mammalian cell.

In a fourth related aspect, the invention features a method for treatment of an HCV-caused disease by administering to a patient an enzymatic RNA molecule which cleaves HCV RNA in the regions discussed above.

The invention provides a class of chemical cleaving agents which exhibit a high degree of specificity for the viral RNA of HCV type infected cells. The ribozyme molecule is preferably targeted to a highly conserved sequence region of HCV such that all types and strains of this virus can be treated with a single ribozyme. Such enzymatic RNA molecules can be delivered exogenously to infected cells. In the preferred hammerhead motif the small size (less than 40 nucleotides, preferably between 32 and 36 nucleotides in length) of the molecule allows the cost of treatment to be reduced compared to other ribozyme motifs.

Synthesis of ribozymes greater than 100 nucleotides in length is very difficult using automated methods, and the therapeutic cost of such molecules is prohibitive. Delivery of ribozymes by expression vectors is primarily feasible using only ex vivo treatments. This limits the utility of this approach. In this invention, small ribozyme motifs (e.g., of the hammerhead structure, shown generally in FIG. 1) are used for exogenous delivery. The simple structure of these molecules also increases the ability of the ribozyme to invade targeted regions of the mRNA structure. Thus, unlike the situation when the hammerhead structure is included within longer transcripts, there are no non-ribozyme flanking sequences to interfere with correct folding of the ribozyme structure or with complementary binding of the ribozyme to the mRNA target region.

The enzymatic RNA molecules of this invention can be used to treat HCV virus infections. Infected animals can be treated at the time of productive infection. This timing of treatment will reduce viral loads in infected cells and disable viral replication in any subsequent rounds of infection. This is possible because the preferred ribozymes disable those structures required for successful initiation of viral protein synthesis. For treatment of transformed hepatocytes, the methods of this invention allow inhibition of the expression of viral genes thought to cause cell transformation.

The preferred targets of the present invention are advantageous over other targets since they do not act only at the time of viral absorption or genomic replication during infection. In addition, viral particles which are released during a first round of infection in the presence of such ribozymes will still be immunogenic by virtue of having their capsids intact. Thus, one method of this invention allows the creation of defective but immunogenic viral particles, and thus a continued possibility of initiation of an immune response in a treated animal.

In addition, the enzymatic RNA molecules of this invention can be used in vitro in a cell culture infected with HCV viruses to produce viral particles which have intact capsids and defective genomic RNA. These particles can then be used for instigation of immune responses in a prophylactic manner, or as a treatment of infected animals.

Other features and advantages of the invention will be apparent from the following description of the preferred embodiments thereof, and from the claims.

DESCRIPTION OF THE PREFERRED EMBODIMENTS

Figure 1:
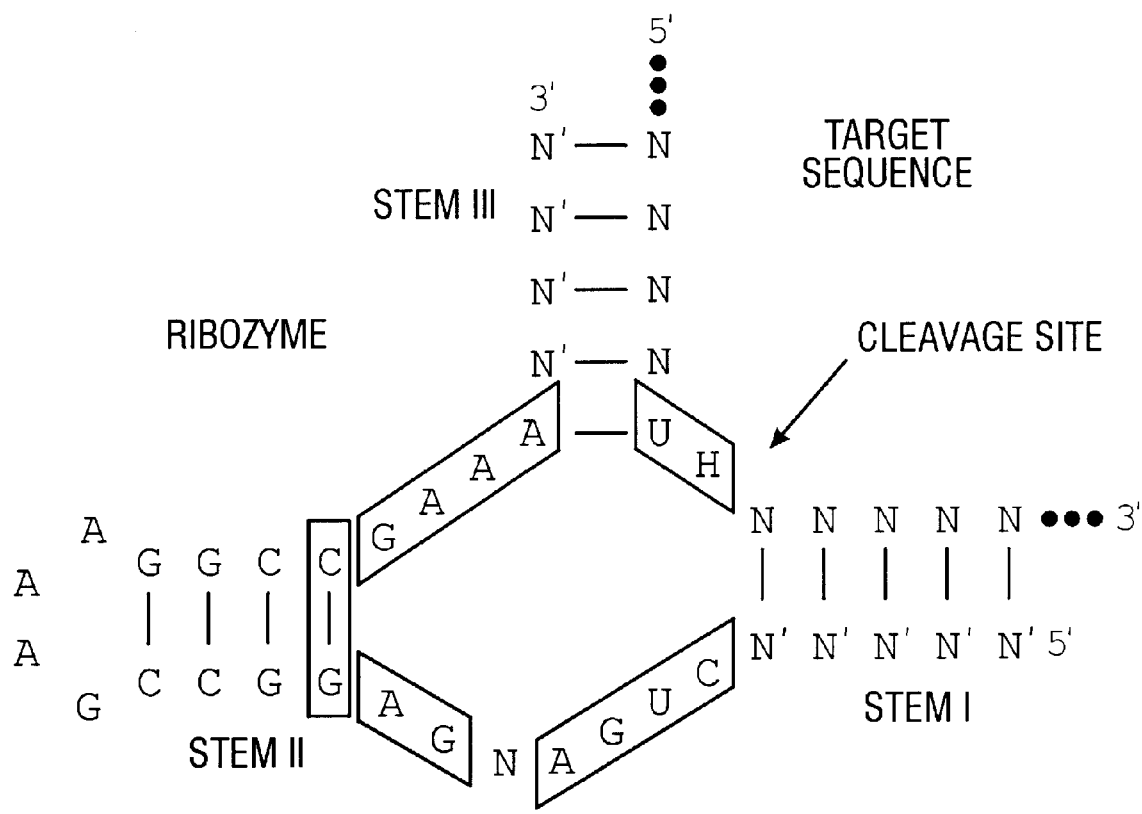

The drawing will first briefly be described.

Drawing

FIG. 1 is a diagrammatic representation of a hammerhead motif ribozyme (SEQ ID NO: 498) showing stems I, II and III (marked (I), (II) and (III) respectively) interacting with an HCV target region. The 5' and 3' ends of both ribozyme and target are shown. Dashes indicate base-paired nucleotides.

Target Sites

The genome of HCV may be subject to rapid genetic drift by virtue of its RNA content and the nature of errors in genomic replication. Those regions (genes) of the genome which are essential for virus replication, however, are expected to maintain a constant sequence (i.e., are conserved) over extensive periods of time. These regions are preferred target sites in this invention since they are more likely to be conserved between different types or strains of HCV viruses, and thus only one ribozyme is needed to destroy all such viruses. Thus, one ribozyme may be used to target all HCV viruses. We have selected several such regions in the genomes of these viruses, and examined their nucleotide sequences for the presence of regions which may be cleaved by ribozymes targeted to those regions. One region analyzed in detail is the 5' non-translated region; other regions (such as the C or NS1 protein ORFs) can be analyzed in a manner similar to that described below.

Ribozymes targeting selected regions of the HCV genome are preferably chosen to cleave the target RNA in a manner which inhibits translation of the RNA. Genes are selected such that such viral replication is inhibited, e.g., by inhibiting protein synthesis. Selection of effective target sites within these critical regions of viral RNA entails testing the accessibility of the target RNA to hybridization with various oligonucleotide probes. These studies can be performed using RNA probes and assaying accessibility by cleaving the hybrid molecule with RNaseH (see below). Alternatively, such a study can use ribozyme probes designed from secondary structure predictions of the RNAs, and assaying cleavage products by polyacrylamide gel electrophoresis (PAGE), to detect the presence of cleaved and uncleaved molecules.

The following is but one example of a method by which suitable target sites can be identified and is not limiting in this invention. Generally, the method involves identifying potential cleavage sites for a hammerhead ribozyme, and then testing each of these sites to determine their suitability as targets by ensuring that secondary structure formation is minimal.

The mRNA sequences of the virus are folded using RNAfold computer analyses. The regions of the mRNA, in this case the 5' nucleotides of the HCV genome, which are predicted to have weak or non-base paired nucleotides are searched for putative ribozyme recognition motifs. These sites represent the preferred sites for hammerhead or other ribozyme cleavage within these target RNAs.

Short RNA substrates corresponding to each of the gene sites are designed. Each substrate is composed of two to three nucleotides at the 5' and 3' ends that will not base pair with a corresponding ribozyme recognition region. The unpaired regions flank a central region of 12–14 nucleotides to which complementary arms in the ribozyme are designed.

The structure of each substrate sequence is predicted using a PC fold computer program. Sequences which give a positive free energy of binding are accepted. Sequences which give a negative free energy are modified by trimming one or two bases from each of the ends. If the modified sequences are still predicted to have a strong secondary structure, they are rejected.

After substrates are chosen, ribozymes are designed to each of the RNA substrates. Ribozyme folding is also analyzed using PC fold.

Ribozyme molecules are sought which form hammerhead motif stem II (see FIG. 1) regions and contain flanking arms which are devoid of intramolecular base pairing. Often the ribozymes are modified by trimming a base from the ends of the ribozyme, or by introducing additional base pairs in stem II to achieve the desired fold. Ribozymes with incorrect folding are rejected. After substrate/ribozyme pairs are found to contain correct intramolecular structures, the molecules are folded together to predict intermolecular interactions. A schematic representation of a ribozyme with its coordinate base pairing to its cognate target sequence is shown in FIG. 1.

Using such analyses, the following predictions of effective target sites in the HCV genomic RNA, based upon computer generated RNA structure analysis, were obtained (see Table 1). The target nucleotide is listed with the genomic nucleotide number (in the HCV genome) given to the left of the sequence. Flanking nucleotides are given for reference.

Those targets thought to be useful as ribozyme targets can be tested to determine accessibility to nucleic acid probes in a ribonuclease H assay (see below). This assay provides a quick test of the use of the target site without requiring synthesis of a ribozyme. It can be used to screen for sites most suited for ribozyme attack.

Synthesis of Ribozymes

Ribozymes useful in this invention can be produced by gene transcription as described by Cech, supra, or by chemical synthesis. Chemical synthesis of RNA is similar to that for DNA synthesis. The additional 2'-OH group in RNA, however, requires a different protecting group strategy to deal with selective 3'-5' internucleotide bond formation, and with RNA susceptibility to degradation in the presence of bases. The recently developed method of RNA synthesis utilizing the t-butyldimethylsilyl group for the protection of the 2' hydroxyl is the most reliable method for synthesis of ribozymes. The method reproducibly yields RNA with the correct 3'-5' internucleotide linkages, with average coupling yields in excess of 99%, and requires only a two-step deprotection of the polymer.

A method based upon H-phosphonate chemistry gives a relatively lower coupling efficiency than a method based upon phosphoramidite chemistry. This is a problem for synthesis of DNA as well. A promising approach to scale-up of automatic oligonucleotide synthesis has been described recently for the H-phosphonates. A combination of a proper coupling time and additional capping of "failure" sequences gave high yields in the synthesis of oligodeoxynucleotides in scales in the range of 14 micromoles with as little as 2 equivalents of a monomer in the coupling step. Another alternative approach is to use soluble polymeric supports e.g., polyethylene glycols), instead of the conventional solid supports. This method can yield short oligonucleotides in hundred milligram quantities per batch utilizing about 3 equivalents of a monomer in a coupling step.

Various modifications to ribozyme structure can be made to enhance the utility of ribozymes. Such modifications will enhance shelf-life, half-life in vitro, stability, and ease of introduction of such ribozymes to the target site, e.g., to enhance penetration of cellular membranes, and confer the ability to recognize and bind to targeted cells.

Exogenous delivery of ribozymes benefits from chemical modification of the backbone, e.g., by the overall negative charge of the ribozyme molecule being reduced to facilitate diffusion across the cell membrane. The present strategies for reducing the oligonucleotide charge include: modification of internucleotide linkages by ethylphosphonates, use of phosphoramidites, linking oligonucleotides to positively charged molecules, and creating complex packages composed of oligonucleotides, lipids and specific receptors or effectors for targeted cells. Examples of such modifications include sulfur-containing ribozymes containing phosphorothioates and phosphorodithioates as internucleotide linkages in RNA. Synthesis of such sulfur-modified ribozymes is achieved by use of the sulfur-transfer reagent, $^3$H-1,2-benzenedithiol-3-one 1,1-dioxide. Ribozymes may also contain ribose modified ribonucleotides. Pyrimidine analogues are prepared from uridine using a procedure employing diethylamino sulphur trifluoride (DAST) as a starting reagent. Ribozymes can also be either electrostatically or covalently attached to polymeric cations for the purpose of reducing charge. The polymer can be attached to the ribozyme by simply converting the 3'-end to a ribonucleoside dialdehyde which is obtained by a periodate cleavage of the terminal 2',3'-cis diol system. Depending on the specific requirements for delivery systems, other possible modifications may include different linker arms containing carboxyl, amino or thiol functionalities. Yet further examples include use of methylphosphonates and 2'-o-methylribose and 5' or 3' capping or blocking with $m_7$GpppG or $m_3^{2,2,7}$GpppG.

For example, a kinased ribozyme is contacted with guanosine triphosphate and guanyltransferase to add a $m^3$G cap to the ribozyme. After such synthesis, the ribozyme can be gel purified using standard procedure. To ensure that the ribozyme has the desired activity, it may be tested with and without the 5' cap using standard procedures to assay both its enzymatic activity and its stability.

Synthetic ribozymes, including those containing various modifiers, can be purified by high pressure liquid chromatography (HPLC). Other liquid chromatography techniques, employing reverse phase columns and anion exchangers on silica and polymeric supports may also be used.

There follows an example of the synthesis of one ribozyme. A solid phase phosphoramidite chemistry is employed. Monomers used are 2'-tert-butyl-dimethylsilyl cyanoethylphosphoramidities of uridine, N-benzoyl-cytosine, N-phenoxyacetyl adenosine and guanosine (Glen Research, Sterling, Va.). Solid phase synthesis is carried out on either an ABI 394 or 380B DNA/RNA synthesizer using the standard protocol provided with each machine. The only exception is that the coupling step is increased from 10 to 12 minutes. The phosphoramidite concentration is 0.1M. Synthesis is done on a 1 µmole scale using a 1 µmole RNA reaction column (Glen Research). The average coupling efficiencies are between 97% and 98% for the 394 model, and between 97% and 99% for the 380B model, as determined by a calorimetric measurement of the released trityl cation.

Blocked ribozymes are cleaved from the solid support (e.g., CPG), and the bases and diphosphoester moiety deprotected in a sterile vial by dry ethanolic ammonia (2 mL) at 55° C. for 16 hours. The reaction mixture is cooled on dry ice. Later, the cold liquid is transferred into a sterile screw cap vial and lyophilized.

To remove the 2'-tert-butyl-dimethylsilyl groups from the ribozyme, the residue is suspended in 1 M tetra-n-butylammonium fluoride in dry THF (TBAF), using a 20 fold excess of the reagent for every silyl group, for 16 hours at ambient temperature (about 15–25° C.). The reaction is quenched by adding an equal volume of sterile 1 M triethylamine acetate, pH 6.5. The sample is cooled and concentrated on a SpeedVac to half the initial volume.

The ribozymes are purified in two steps by HPLC on a C4 300µ 5 mm DeltaPak column in an acetonitrile gradient.

The first step, or "trityl on" step, is a separation of 5'-DMT-protected ribozyme(s) from failure sequences lacking a 5'-DMT group. Solvents used for this step are: A (0.1 M triethylammonium acetate, pH 6.8) and B (acetonitrile). The elution profile is: 20% B for 10 minutes, followed by a linear gradient of 20% B to 50% B over 50 minutes, 50% B for 10 minutes, a linear gradient of 50% B to 100% B over 10 minutes, and a linear gradient of 100% B to 0% B over 10 minutes.

The second step is a purification of a completely deblocked ribozyme by a treatment of 2% trifluoroacetic acid on a C4 300µ 5 mm DeltaPak column in an acetonitrile gradient. Solvents used for this second step are: A (0.1 M Triethylammonium acetate, pH 6.8) and B (80% acetonitrile, 0.1 M triethylammonium acetate, pH 6.8). The elution profile is: 5% B for 5 minutes, a linear gradient of 5S B to 15% B over 60 minutes, 15% B for 10 minutes, and a linear gradient of 15% B to 0% B over 10 minutes.

The fraction containing ribozyme is cooled and lyophilized on a SpeedVac. Solid residue is dissolved in a minimum amount of ethanol and sodium perchlorate in acetone. The ribozyme is collected by centrifugation, washed three times with acetone, and lyophilized.

Expression Vector

While synthetic ribozymes are preferred in this invention, those produced by expression vectors can also be used. In designing a suitable ribozyme expression vector the following factors are important to consider. The final ribozyme must be kept as small as possible to minimize unwanted secondary structure within the ribozyme. A promoter (e.g., the human cytomegalovirus immediate early promoter) should be chosen to be a relatively strong promoter, and expressible both in vitro and in vivo. Such a promoter should express the ribozyme at a level suitable to effect production of enough ribozyme to destroy a target RNA, but not at too high a level to prevent other cellular activities from occurring (unless cell death itself is desired).

A hairpin at the 5' end of the ribozyme is useful to protect the ribozyme from 5'-3' exonucleases. A selected hairpin at the 3' end of the ribozyme is useful because it acts as a protection from 3'-5' exonucleases. Such hairpins can be inserted within the vector sequences to allow standard ribozymes to be placed in an appropriate orientation and expressed with such sequences attached.

Poly(A) tails are also useful to protect the 3' end of the ribozyme. These can be provided by either including a poly(A) signal site in the expression vector (to signal a cell to add the poly(A) tail in vivo), or by introducing a poly(A) sequence directly into the expression vector. In the first approach the signal must be located to prevent unwanted secondary structure formation with other parts of the ribozyme. In the second approach, the poly(A) stretch may reduce in size over time when expressed in vivo, and thus the vector may need to be checked over time. Care must be taken in addition of a poly(A) tail which binds poly(A) binding proteins which prevent the ribozyme from acting upon their target sequence.

Ribozyme Testing

Once the desired ribozymes are selected, synthesized and purified, they are tested in kinetic and ocher experiments to determine their utility. An example of such a procedure is provided below.

Preparation of Ribozyme

Crude synthetic ribozyme (typically 350 µg at a time) is purified by separation on a 15% denaturing polyacrylamide gel (0.75 mm thick, 40 cm long) and visualized by UV shadowing. Once excised, gel slices containing full length ribozyme are soaked in 5 ml gel elution buffer (0.5 M NH$_4$OAc, 1 mM EDTA) overnight with shaking at 4° C. The eluent is desalted over a C-18 matrix (Sep-Pak cartridges, Millipore, Milford, Mass.) and vacuum dried. The dried RNA is resuspended in 50–100 µl TE (TRIS 10 mM, EDTA 1 mM, pH 7.2). An aliquot of this solution is diluted 100 fold into 1 ml TE, half of which was used to spectrophotometrically quantitate the ribozyme solution. The concentration of this dilute stock is typically 150–800 nM. Purity of the ribozyme is confirmed by the presence of a single band on a denaturing polyacrylamide gel.

A ribozyme may advantageously be synthesized in two or more portions. Each portion of a ribozyme will generally have only limited or no enzymatic activity, and the activity will increase substantially (by at least 5–10 fold) when all portions are ligated (or otherwise juxtaposed) together. A specific example of hammerhead ribozyme synthesis is provided below.

The method involves synthesis of two (or more) shorter "half" ribozymes and ligation of them together using T4 RNA ligase. For example, to make a 34 mer ribozyme, two 17 mers are synthesized, one is phosphorylated, and both are gel purified. These purified 17 mers are then annealed to a DNA splint strand complementary to the two 17 mers. This DNA splint has a sequence designed to locate the two 17 mer portions with one end of each adjacent each other. The juxtaposed RNA molecules are then treated with T4 RNA ligase in the presence of ATP. The 34 mer RNA so formed is then HPLC purified.

Preparation of Substrates

Approximately 10–30 pmoles of unpurified substrate is radioactively 5' end-labelled with T4 polynucleotide kinase using 25 pmoles of [Letter to client re action proposed γ-$^{32}$P] ATP. The entire labelling mix is separated on a 20% denaturing polyacrylamide gel and visualized by autoradiography. The full length band is excised and soaked overnight at 4° C. in 100 μl of TE (10 mM Tris-HCl pH 7.6, 0.1 MM EDTA).

Kinetics Reactions

For reactions using short substrates (between 8 and 16 bases) a substrate solution is made 1× in assay buffer (75 MM Tris-HCl, pH 7.6; 0.1 mM EDTA, 10 mM MgCl$_2$) such that the concentration of substrate is less than 1 nM. A ribozyme solution (typically 20 nM) is made 1× in assay buffer and four dilutions are made using 1× assay buffer. Fifteen μl of each ribozyme dilution (i.e., 20, 16, 12, 8 and 4 nM) is placed in a separate tube. These tubes and the substrate tube are pre-incubated at 37° C. for at least five minutes.

The reaction is started by mixing 15 μl of substrate into each ribozyme tube by rapid pipetting (note that final ribozyme concentrations are 10, 8, 6, 4, 2 nM). 5 μl aliquots are removed at 15 or 30 second intervals and quenched with 5 μl stop solution (95% formamide, 20 mM EDTA xylene cyanol, and bromphenol blue dyes). Following the final ribozyme time point, an aliquot of the remaining substrate is removed as a zero ribozyme control.

The samples are separated on either 15% or 20% polyacrylamide gels. Each gel is visualized and quantitated with an Ambis beta scanner (Ambis Systems, San Diego, Calif.).

For the most active ribozymes, kinetic analyses are performed in substrate excess to determine K$_m$ and K$_{cat}$ values.

For kinetic reactions with long RNA substrates (greater than 15 bases in length) the substrates are prepared by transcription using T7 RNA polymerase and defined templates containing a T7 promoter, and DNA encoding appropriate nucleotides of the viral RNA. The substrate solution is made 1× in assay buffer (75 mM Tris-HCl, pH 7.6; 0.1 mM EDTA; 10 mM MgCl$_2$) and contains 58 nanomolar concentration of the long RNA molecules. The reaction is started by addition of gel purified ribozymes to 1 μM concentration. Aliquots are removed at 20, 40, 60, 80 and 100 minutes, then quenched by the addition of 5 μl stop solution. Cleavage products are separated using denaturing PAGE. The bands are visualized and quantitated with an Ambis beta scanner.

Kinetic Analysis

A simple reaction mechanism for ribozyme-mediated cleavage is:

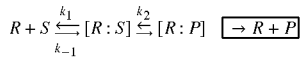

where R=ribozyme, S=substrate, and P=products. The boxed step is important only in substrate excess. Because ribozyme concentration is in excess over substrate concentration, the concentration of the ribozyme-substrate complex ([R:S]) is constant over time except during the very brief time when the complex is being initially formed, i.e.,:

$$\frac{d[R:S]}{dt} = 0$$

where t=time, and thus:

$$(R)(S)k_1 = (RS)(k_2 + k_1)$$

The rate of the reaction is the rate of disappearance of substrate with time:

$$\text{Rate} = \frac{-d(S)}{dt} = k_2(RS)$$

Substituting these expressions:

$$(R)(S)k_1 = 1/k_2 \frac{-d(S)}{dt}(k_2 + k_1)$$

or:

$$\frac{-d(S)}{S} = \frac{k_1 k_2}{(k_2 + k_1)}(R)dt$$

Integrating this expression with respect to time yields:

$$-\ln\frac{S}{S_0} = \frac{k_1 k_2}{(k_2 + k_1)}(R)t$$

where S$_0$=initial substrate. Therefore, a plot of the negative log of fraction substrate uncut versus time (in minutes) yields a straight line with slope:

$$\text{slope} = \frac{k_1 k_2}{(k_2 + k_1)}(R) = k_{obs}$$

where k$_{obs}$=observed rate constant. A plot of slope (k$_{obs}$) versus ribozyme concentration yields a straight line with a slope which is:

$$\text{slope} = \frac{k_1 k_2}{(k_2 + k_1)} \text{ which is } \frac{k_{cat}}{K_m}$$

Using these equations the data obtained from the kinetic experiments provides the necessary information to determine which ribozyme tested is most useful, or active. Such ribozymes can be selected and tested in in vivo or ex vivo systems.

Liposome Preparation

Lipid molecules are dissolved in a volatile organic solvent (CHCl$_3$, methanol, diethylether, ethanol, etc.). The organic solvent is removed by evaporation. The lipid is hydrated into suspension with 0.1× phosphate buffered saline (PBS), then freeze-thawed 3× using liquid nitrogen and incubation at room temperature. The suspension is extruded sequentially through a 0.4 µm, 0.2 µm and 0.1 µm polycarbonate filters at maximum pressure of 800 psi. The ribozyme is mixed with the extruded liposome suspension and lyophilized to dryness. The lipid/ribozyme powder is rehydrated with water to one-tenth the original volume. The suspension is diluted to the minimum volume required for extrusion (0.4 ml for 1.5 ml barrel and 1.5 ml for 10 ml barrel) with 1×PBS and re-extruded through 0.4 µm, 0.2 µm, 0.1 µm polycarbonate filters. The liposome entrapped ribozyme is separated from untrapped ribozyme by gel filtration chromatography (SEPHAROSE CL-4B, BIOGEL A5M). The liposome extractions are pooled and sterilized by filtration through a 0.2 µm filter. The free ribozyme is pooled and recovered by ethanol precipitation. The liposome concentration is determined by incorporation of a radioactive lipid. The ribozyme concentration is determined by labeling with $^{32}$P. Rossi et al., 1992 supra (and references cited therein) describe other methods suitable for preparation of liposomes.

In Vivo Assay

The efficacy of action of a chosen ribozyme may be tested in vivo by use of cell cultures sensitive to HCV using standard procedures. For example, monolayer cultures of HCV-sensitive HepG2 cells are grown in 6 or 96 well tissue culture plates. Prior to transduction with HCV expression plasmids, cultures are treated for three to 24 hours with ribozyme-containing liposomes or cationic lipid/ribozyme complexes. Cells are then rinsed with phosphate buffered saline (PBS) and transduced or transfected with HCV expression plasmids. The cells are treated for three to five days with appropriate ribozyme preparations in fresh changes of medium. Total cellular RNA is harvested by the guanidine isothiocyanate technique and the amount of HCV mRNA is quantified and assessed for ribozyme-mediated cleavage using the ribonuclease protection assay. Alternatively, cellular lysates can be prepared and the core particles of HCV could be immunoprecipitated using polyclonal anti-core antiserum adsorbed to protein A-Sepharose according to manufacturers directions. The precipitated cores are treated with ribonuclease to digest any non-encapsidated RNAs and the core protein is digested with proteinase K/phenol extraction. Usually one-half of the total RNA and one-half of the extracted RNA is analyzed using the ribonuclease protection assay.

Ribonuclease Protection Assay

The accumulation of target mRNA in cells or the cleavage of the RNA by ribozymes or RNaseH (in vitro or an vivo) can be quantified using an RNase protection assay.

In this method, antisense riboprobes are transcribed from template DNA using T7 RNA polymerase (U.S. Biochemicals) in 20 µl reactions containing 1× transcription buffer (supplied by the manufacturer), 0.2 mM ATP, GTP and UTP, 1 U/µl pancreatic RNase inhibitor (Boehringer Mannheim Biochemicals) and 200 µCi $^{32}$P-labeled CTP (800 Ci/mmol, New England Nuclear) for 1 h at 37° C. Template DNA is digested with 1 U RNase-free DNase I (U.S. Biochemicals, Cleveland, Ohio) at 37° C. for 15 minutes and unincorporated nucleotides removed by G-50 SEPHADEX spin chromatography.

In a manner similar to the transcription of antisense probe, the target RNA can be transcribed in vitro using a suitable DNA template. The transcript is purified by standard methods and digested with ribozyme at 37° C. according to methods described later.

Alternatively, virus-infected cells are harvested into 1 ml of PBS, transferred to a 1.5 ml EPPENDORF tube, pelleted for 30 seconds at low speed in a microcentrifuge, and lysed in 70 µl of hybridization buffer (4 M guanidine isothiocyanate, 0.1% sarcosyl, 25 mM sodium citrate, pH 7.5). Cell lysate (45 µl) or defined amounts of in vitro transcript (also in hybridization buffer) is then combined with 5 µl of hybridization buffer containing 5×10$^5$ cpm of each antisense riboprobe in 0.5 ml EPPENDORF tubes, overlaid with 25 µl mineral oil, and hybridization accomplished by heating overnight at 55° C. The hybridization reactions are diluted into 0.5 ml RNase solution (20 U/ml RNase A, 2 U/ml RNase T1, 10 U/ml RNase-free DNAse I in 0.4 M NaCl), heated for 30 minutes at 37° C., and 10 µl of 20% SDS and 10 µl of Proteinase K (10 mg/ml) added, followed by an additional 30 minutes incubation at 37° C. Hybrids are partially purified by extraction with 0.5 ml of a 1:1 mixture of phenol/chloroform; aqueous phases are combined with 0.5 ml isopropanol, and RNase-resistant hybrids pelleted for 10 minutes at room temperature (about 20° C.) in a microcentrifuge. Pellets are dissolved in 10 µl loading buffer (95% formamide, 1× TBE, 0.1% bromophenol blue, 0.1% xylene cylanol), heated to 95° C. for five minutes, cooled on ice, and analyzed on 4% polyacrylamide/7 M urea gels under denaturing conditions.

Ribozyme Stability

The chosen ribozyme can be tested to determine its stability, and thus its potential utility. Such a test can also be used to determine the effect of various chemical modifications (e.g., addition of a poly(A) tail) on the ribozyme stability and thus aid selection of a more stable ribozyme. For example, a reaction mixture contains 1 to 5 pmoles of 5' (kinased) and/or 3' labeled ribozyme, 15 µg of cytosolic extract and 2.5 mM MgCl$_2$ in a total volume of 100 µl. The reaction is incubated at 37° C. Eight µl aliquots are taken at timed intervals and mixed with 8 µl of a stop mix (20 mM EDTA, 95% formamide) Samples are separated on a 15% acrylamide sequencing gel, exposed to film, and scanned with an Ambis.

A 3'-labelled ribozyme can be formed by incorporation of the $^{32}$P-labeled cordycepin at the 3' OH using poly(A) polymerase. For example, the poly(A) polymerase reaction contains 40 mM Tris, pH 8, 10 mM MgCl$_2$, 250 mM NaCl, 2.5 mM MnCl$_2$,; 3 µl P$^{32}$ cordycepin, 500 Ci/mM; and 6 units poly(A) polymerase in a total volume of 50 µl. The reaction mixture was incubated for 30 minutes at 37° C.

Effect of Base Substitution Upon Ribozyme Activity

To determine which primary structural characteristics could change ribozyme cleavage of substrate, minor base changes can be made in the substrate cleavage region recognized by a specific ribozyme. For example, the substrate sequences can be changed at the central "C" nucleotide, changing the cleavage site from a GUC to a GUA motif. The $K_{cat}/K_m$ values for cleavage using each substrate are then analyzed to determine if such a change increases ribozyme cleavage rates. Similar experiments can be performed to address the effects of changing bases complementary to the ribozyme binding arms. Changes predicted to maintain strong binding to the complementary substrate are preferred. Minor changes in nucleotide content can alter ribozyme/substrate interactions in ways which are unpredictable based upon binding strength alone. Structures in the catalytic core region of the ribozyme recognize trivial changes in either substrate structure or the three dimensional structure of the ribozyme/substrate complex.

To begin optimizing ribozyme design, the cleavage rates of ribozymes containing varied arm lengths, but targeted to the same length of short RNA substrate can be tested. Minimal arm lengths are required and effective cleavage varies with ribozyme/substrate combinations.

The cleavage activity of selected ribozymes can be assessed using HCV-homologous substrates or HCV genomic RNA. The assays are performed in ribozyme excess and approximate $K_{cat}/K_{min}$ values obtained. Comparison of values obtained with short and long substrates indicates utility in vivo of a ribozyme.

Intracellular Stability of liposome-delivered Ribozymes

To test the stability of a chosen ribozyme in vivo the following test is useful. Ribozymes are $^{32}$P-end labeled, entrapped in liposomes and delivered to HCV sensitive cells for three hours. The cells are fractionated and purified by phenol/chloroform extraction. Cells ($1 \times 10^7$, T-175 flask) are scraped from the surface of the flask and washed twice with cold PBS. The cells are homogenized by douncing 35 times in 4 ml of TSE (10 mM Tris, pH 7.4, 0.25 M Sucrose, mM EDTA). Nuclei are pelleted at 100×g for 10 minutes. Sub-cellular organelles (the membrane fraction) are pelleted at 200,000×g for two hours using an SW60 rotor. The pellet is resuspended in 1 ml of H buffer (0.25 M Sucrose, 50 mM HEPES, pH 7.4) The supernatant contains the cytoplasmic fraction (in approximately 3.7 ml). The nuclear pellet is resuspended in 1 ml of 65% sucrose in TM (50 mM Tris, pH 74., 2.5 mM $MgCl_2$) and banded on a sucrose step gradient (1 ml nuclei in 65% sucrose TM, 1 ml 60% sucrose TM, 1 ml 55% sucrose TM, 50% sucrose TM, 300 ul 25% sucrose TM) for one hour at 37,000×g with an SW60 rotor. The nuclear band is harvested and diluted to 10% sucrose with TM buffer. Nuclei are pelleted at 37,000×g using an SW60 rotor for 15 minutes and the pellet resuspended in 1 ml of TM buffer. Aliquots are size fractionated on denaturing polyacrylamide gels and the intracellular localization determined. By comparison to the migration rate of newly synthesized ribozyme, the various fraction containing intact ribozyme can be determined.

To investigate modifications which would lengthen the half-life of ribozyme molecules intracellularly, the cells may be fractioned as above and the purity of each fraction assessed by assaying enzyme activity known to exist in that fraction.

The various cell fractions are frozen at −70° C. and used to determine relative nuclease resistances of modified ribozyme molecules. Ribozyme molecules may be synthesized with 5 phosphorothioate (ps), or 2'-O-methyl (2'-OMe) modifications at each end of the molecule. These molecules and a phosphodiester version of the ribozyme are end-labeled with $^{32}$P and ATP using T4 polynucleotide kinase. Equal concentrations are added to the cell cytoplasmic extracts and aliquots of each taken at 10 minute intervals. The samples are size fractionated by denaturing PAGE and relative rates of nuclease resistance analyzed by scanning the gel with an Ambis scanner. The results show whether the ribozymes are digested by the cytoplasmic extract, and which versions are relatively more nuclease resistant. Modified ribozymes generally maintain 80–90% of the catalytic activity of the native ribozyme when short RNA substrates are employed.

Unlabeled, 5' end-labeled or 3' end-labeled ribozymes can be used in the assays. These experiments can also be performed with human cell extracts to verify the observations.

Administration of Ribozyme

Selected ribozymes can be administered prophylactically, or to virus infected patients, e.g., by exogenous delivery of the ribozyme to an infected tissue by means of an appropriate delivery vehicle, e.g., a liposome, a controlled release vehicle, by use of iontophoresis, electroporation or ion paired molecules, or covalently attached adducts, and other pharmacologically approved methods of delivery. Routes of administration include intramuscular, aerosol, oral (tablet or pill form), topical, systemic, ocular, intraperitoneal and/or intrathecal. Expression vectors for immunization with ribozymes and/or delivery of ribozymes are also suitable. See Draper, U.S. Ser. No. 08/152,487, filed Nov. 12, 1993, the whole of which including drawings is hereby incorporated herein by reference. See, also, Sullivan, U.S. Ser. No. 08/155,474, the whole of which including drawings is hereby incorporated herein by reference.

The specific delivery route of any selected ribozyme will depend on the use of the ribozyme. Generally, a specific delivery program for each ribozyme will focus on naked ribozyme uptake with regard to intracellular localization, followed by demonstration of efficacy. Alternatively, delivery to these same cells in an organ or tissue of an animal can be pursued. Uptake studies will include uptake assays to evaluate cellular ribozyme uptake, regardless of the delivery vehicle or strategy. Such assays will also determine the intracellular localization of the ribozyme following uptake, ultimately establishing the requirements for maintenance of steady-state concentrations within the cellular compartment containing the target sequence (nucleus and/or cytoplasm). Efficacy and cytotoxicity can then be tested. Toxicity will not only include cell viability but also cell function.

Some methods of delivery that may be used include:

a. encapsulation in liposomes, b. transduction by retroviral vectors, c. conjugation with cholesterol, d. localization to nuclear compartment utilizing antigen binding site found on most snRNAs, e. neutralization of charge of ribozyme by using nucleotide derivatives, and f. use of blood stem cells to distribute ribozymes throughout the body.

At least three types of delivery strategies are useful in the present invention, including: ribozyme modifications, particle carrier drug delivery vehicles, and viral expression vectors. Unmodified ribozymes and antisense oligonucleotides, like most small molecules, are taken up by cells, albeit slowly. To enhance cellular uptake, the ribozyme may be modified essentially at random, in ways which reduces its charge but maintains specific functional groups. This results in a molecule which is able to diffuse across the cell membrane, thus removing the permeability barrier.

Modification of ribozymes to reduce charge is just one approach to enhance the cellular uptake of these larger molecules. The random approach, however, is not advisable since ribozymes are structurally and functionally more complex than small drug molecules. The structural requirements necessary to maintain ribozyme catalytic activity are well understood by those in the art. These requirements are taken into consideration when designing modifications to enhance cellular delivery. The modifications are also designed to reduce susceptibility to nuclease degradation. Both of these characteristics should greatly improve the efficacy of the ribozyme. Cellular uptake can be increased by several orders of magnitude without having to alter the phosphodiester linkages necessary for ribozyme cleavage activity.

Chemical modifications of the phosphate backbone will reduce the negative charge allowing free diffusion across the membrane. This principle has been successfully demonstrated for antisense DNA technology. The similarities in chemical composition between DNA and RNA make this a feasible approach. In the body, maintenance of an external concentration will be necessary to drive the diffusion of the modified ribozyme into the cells of the tissue. Administration routes which allow the diseased tissue to be exposed to a transient high concentration of the drug, which is slowly dissipated by systemic adsorption are preferred. Intravenous administration with a drug carrier designed to increase the circulation half-life of the ribozyme can be used. The size and composition of the drug carrier restricts rapid clearance from the blood stream. The carrier, made to accumulate at the site of infection, can protect the ribozyme from degradative processes.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

From this category of delivery systems, liposomes are preferred. Liposomes increase intracellular stability, increase uptake efficiency and improve biological activity.

Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver RNA to cells and that the RNA remains biologically active.

For example, a liposome delivery vehicle originally designed as a research tool, Lipofectin, has been shown to deliver intact mRNA molecules to cells yielding production of the corresponding protein.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Other controlled release drug delivery systems, such as nonoparticles and hydrogels may be potential delivery vehicles for a ribozyme. These carriers have been developed for chemotherapeutic agents and protein-based pharmaceuticals, and consequently, can be adapted for ribozyme delivery.

Topical administration of ribozymes is advantageous since it allows localized concentration at the site of administration with minimal systemic adsorption. This simplifies the delivery strategy of the ribozyme to the disease site and reduces the extent of toxicological characterization. Furthermore, the amount of material to be applied is far less than that required for other administration routes. Effective delivery requires the ribozyme to diffuse into the infected cells. Chemical modification of the ribozyme to neutralize negative charge may be all that is required for penetration. However, in the event that charge neutralization is insufficient, the modified ribozyme can be co-formulated with permeability enhancers, such as Azone or oleic acid, in a liposome. The liposomes can either represent a slow release presentation vehicle in which the modified ribozyme and permeability enhancer transfer from the liposome into the infected cell, or the liposome phospholipids can participate directly with the modified ribozyme and permeability enhancer in facilitating cellular delivery. In some cases, both the ribozyme and permeability enhancer can be formulated into a suppository formulation for slow release.

Ribozymes may also be systemically administered. Systemic absorption refers to the accumulation of drugs in the blood stream followed by distribution throughout the entire body. Administration routes which lead to systemic absorption include: intravenous, subcutaneous, intraperitoneal, intranasal, intrathecal and ophthalmic. Each of these administration routes expose the ribozyme to an accessible diseased tissue. Subcutaneous administration drains into a localized lymph node which proceeds through the lymphatic network into the circulation. The rate of entry into the circulation has been shown to be a function of molecular weight or size. The use of a liposome or other drug carrier localizes the ribozyme at the lymph node. The ribozyme can be modified to diffuse into the cell, or the liposome can directly participate in the delivery of either the unmodified or modified ribozyme to the cell.

Intraperitoneal administration also leads to entry into the circulation, with once again, the molecular weight or size controlling the rate of entry.

Liposomes injected intravenously show accumulation in the liver, lung and spleen. The composition and size can be adjusted so that this accumulation represents 30% to 40% of the injected dose. The rest is left to circulate in the blood stream for up to 24 hours.

The chosen method of delivery should result in cytoplasmic accumulation and molecules should have some nuclease-resistance for optimal dosing. Nuclear delivery may be used but is less preferable. Most preferred delivery methods include liposomes (10–400 nm), hydrogels, controlled-release polymers, microinjection or electroporation (for ex vivo treatments) and other pharmaceutically applicable vehicles. The dosage will depend upon the disease indication and the route of administration but should be between 100–200 mg/kg of body weight/day. The duration of treatment will extend through the course of the disease symptoms, usually at least 14–16 days and possibly continuously. Multiple daily doses are anticipated for topical applications, ocular applications and vaginal applications. The number of doses will depend upon disease delivery vehicle and efficacy data from clinical trials.

Establishment of therapeutic levels of ribozyme within the cell is dependent upon the rate of uptake and degradation. Decreasing the degree of degradation will prolong the intracellular half-life of the ribozyme. Thus, chemically modified ribozymes, e.g., with modification of the phosphate backbone, or capping of the 5' and 3' ends of the ribozyme with nucleotide analogs may require different dosaging. Descriptions of useful systems are provided in the art cited above, all of which is hereby incorporated by reference herein.

The claimed ribozymes are also useful as diagnostic tools to specifically or non-specifically detect the presence of a target RNA in a sample. That is, the target RNA, if present in the sample, will be specifically cleaved by the ribozyme, and thus can be readily and specifically detected as smaller RNA species. The presence of such smaller RNA species is indicative of the presence of the target RNA in the sample.

Other embodiments are within the following claims.

What is claimed is:

1. An enzymatic nucleic acid molecule which specifically inhibits hepatitis C virus (HCV) replication.

2. The enzymatic nucleic acid molecule of claim 1, wherein said enzymatic nucleic acid molecule is capable of cleaving a separate RNA molecule.

3. The enzymatic nucleic acid molecule of claim 2, wherein said separate RNA molecule is encoded by HCV.

4. The enzymatic nucleic acid molecule of claim 2, wherein said enzymatic nucleic acid cleaves HCV genomic RNA.

5. The enzymatic nucleic acid molecule of claim 2, wherein said enzymatic nucleic acid is in a hammerhead configuration.

6. The enzymatic nucleic acid molecule of claim 2, wherein said enzymatic nucleic acid molecule is in a hairpin motif.

7. The enzymatic nucleic molecule of claim 2, wherein said enzymatic nucleic acid molecule comprises substrate binding region including between 12 and 100 nucleotides complementary to said separate RNA.

8. The enzymatic nucleic acid molecule of claim 7, wherein said substrate binding region comprises between 14 and 24 nucleotides complementary to said separate RNA.

9. An expression vector comprising nucleic acid sequence encoding one or more enzymatic nucleic acid molecule of claim 1 in a manner which allows expression of said enzymatic nucleic acid molecules.

10. The expression vector of claim 9, wherein said expression vector is a viral vector.

11. The expression vector of claim 10, wherein said viral vector is a retrovirus vector.

12. The enzymatic nucleic acid molecule of claim 1, wherein said enzymatic nucleic acid molecule is chemically synthesized.

13. The enzymatic nucleic acid molecule of claim 1, wherein said enzymatic nucleic acid molecule is in a purified form.

14. The enzymatic nucleic acid molecule of claim 1, wherein said enzymatic nucleic acid molecule is active in the presence of divalent metal ions.

15. The enzymatic nucleic acid molecule of claim 14, wherein said divalent metal ion is magnesium.

16. The enzymatic nucleic acid molecule of claim 1, wherein said enzymatic nucleic acid molecule comprises a ribose modification.

17. The expression vector of claim 9, wherein said nucleic acid sequence encoding said enzymatic nucleic acid molecule is under the control of a mammalian transcription promoter.

18. The expression vector of claim 17, wherein said mammalian transcription promoter is a cytomegalovirus promoter.

19. The enzymatic nucleic acid molecule of claim 1, wherein said enzymatic nucleic acid molecule comprises a 5'-cap.

20. The enzymatic nucleic acid molecule of claim 1, wherein said enzymatic nucleic acid molecule comprises a 3'-cap.

21. The enzymatic nucleic acid molecule of claim 1, wherein said enzymatic nucleic acid molecule comprises a 3'-polyA tail.

22. A method of inhibiting HCV replication in a mammalian cell comprising the step of contacting said mammalian cell with the enzymatic nucleic acid molecule of claim 1 under conditions suitable for the inhibition of the HCV replication, wherein said cell is not in a human.

23. The method of claim 22, wherein said mammalian cell is a human cell.

24. The enzymatic nucleic acid molecule of claim 1 or 2, wherein said enzymatic nucleic acid molecule comprises one or more chemical modifications.

25. The enzymatic nucleic acid molecule of claim 24, wherein said chemical modification is a sugar modification.

26. The enzymatic nucleic acid molecule of claim 24, wherein said chemical modification is a nucleic acid base modification.

27. The enzymatic nucleic acid molecule of claim 24, wherein said chemical modification is a phosphodiester backbone modification.

28. The enzymatic nucleic acid molecule of claim 24, wherein said backbone modification is a phosphorothioate modification.

29. The enzymatic nucleic acid molecule of claim 24, wherein said chemical modification localizes said enzymatic nucleic acid to the site of said separate RNA molecule.

* * * * *

SEQUENCE LISTING (1) GENERAL INFORMATION:

(iii) NUMBER OF SEQUENCES: 498

(2) INFORMATION FOR SEQ ID NO: 1:

(i) SEQUENCE CHARACTERISTICS:
      (A) LENGTH:       15
      (B) TYPE:         nucleic acid
      (C) STRANDEDNESS: single
      (D) TOPOLOGY:     linear (xi) SEQUENCE DESCRIPTION: SEQ ID NO: 1:

CGACACUCCA CCAUA                                              15

(2) INFORMATION FOR SEQ ID NO: 2:

(i) SEQUENCE CHARACTERISTICS:
      (A) LENGTH:       15
      (B) TYPE:         nucleic acid
      (C) STRANDEDNESS: single
      (D) TOPOLOGY:     linear (xi) SEQUENCE DESCRIPTION: SEQ ID NO: 2:

GCAGCCUCCA GGACC                                              15

(2) INFORMATION FOR SEQ ID NO: 3:

(i) SEQUENCE CHARACTERISTICS:
      (A) LENGTH:       15
      (B) TYPE:         nucleic acid
      (C) STRANDEDNESS: single
      (D) TOPOLOGY:     linear (xi) SEQUENCE DESCRIPTION: SEQ ID NO: 3:

CCCCCCUCCC GGGAG                                              15

(2) INFORMATION FOR SEQ ID NO: 4:

(i) SEQUENCE CHARACTERISTICS:
      (A) LENGTH:       15
      (B) TYPE:         nucleic acid
      (C) STRANDEDNESS: single
      (D) TOPOLOGY:     linear (xi) SEQUENCE DESCRIPTION: SEQ ID NO: 4:

UAGUGGUCUG CGGAA                                              15

(2) INFORMATION FOR SEQ ID NO: 5:

(i) SEQUENCE CHARACTERISTICS:
      (A) LENGTH:       15
      (B) TYPE:         nucleic acid
      (C) STRANDEDNESS: single
      (D) TOPOLOGY:     linear (xi) SEQUENCE DESCRIPTION: SEQ ID NO: 5:

GGUGAGUACA CCGGA                                              15

(2) INFORMATION FOR SEQ ID NO: 6:

(i) SEQUENCE CHARACTERISTICS:
      (A) LENGTH:       15
      (B) TYPE:         nucleic acid
      (C) STRANDEDNESS: single

```
            (D) TOPOLOGY:         linear (xi) SEQUENCE DESCRIPTION: SEQ ID NO: 6:

CCGGAAUUGC CAGGA                                                15

(2) INFORMATION FOR SEQ ID NO:   7:

(i) SEQUENCE CHARACTERISTICS:
            (A) LENGTH:           15
            (B) TYPE:             nucleic acid
            (C) STRANDEDNESS:     single
            (D) TOPOLOGY:         linear (xi) SEQUENCE DESCRIPTION: SEQ ID NO: 7:

CCUUUCUUGG AUCAA                                                15

(2) INFORMATION FOR SEQ ID NO:   8:

(i) SEQUENCE CHARACTERISTICS:
            (A) LENGTH:           15
            (B) TYPE:             nucleic acid
            (C) STRANDEDNESS:     single
            (D) TOPOLOGY:         linear (xi) SEQUENCE DESCRIPTION: SEQ ID NO: 8:

ACCCGCUCAA UGCCU                                                15

(2) INFORMATION FOR SEQ ID NO:   9:

(i) SEQUENCE CHARACTERISTICS:
            (A) LENGTH:           15
            (B) TYPE:             nucleic acid
            (C) STRANDEDNESS:     single
            (D) TOPOLOGY:         linear (xi) SEQUENCE DESCRIPTION: SEQ ID NO: 9:

GACUGCUAGC CGAGU                                                15

(2) INFORMATION FOR SEQ ID NO:  10:

(i) SEQUENCE CHARACTERISTICS:
            (A) LENGTH:           15
            (B) TYPE:             nucleic acid
            (C) STRANDEDNESS:     single
            (D) TOPOLOGY:         linear (xi) SEQUENCE DESCRIPTION: SEQ ID NO: 10:

GCCGAGUAGU GUUGG                                                15

(2) INFORMATION FOR SEQ ID NO:  11:

(i) SEQUENCE CHARACTERISTICS:
            (A) LENGTH:           15
            (B) TYPE:             nucleic acid
            (C) STRANDEDNESS:     single
            (D) TOPOLOGY:         linear (xi) SEQUENCE DESCRIPTION: SEQ ID NO: 11:

GUAGUGUUGG GUCGC                                                15

(2) INFORMATION FOR SEQ ID NO:  12:

(i) SEQUENCE CHARACTERISTICS:
            (A) LENGTH:           15
            (B) TYPE:             nucleic acid
            (C) STRANDEDNESS:     single
            (D) TOPOLOGY:         linear
```

(xi) SEQUENCE DESCRIPTION: SEQ ID NO: 12:

GUUGGGUCGC GAAAG                                                15

(2) INFORMATION FOR SEQ ID NO:   13:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 13:

UUGUGGUACU GCCUG                                                15

(2) INFORMATION FOR SEQ ID NO:   14:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 14:

GCCUGAUAGG GUGCU                                                15

(2) INFORMATION FOR SEQ ID NO:   15:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 15:

GGGUGCUUGC GAGUG                                                15

(2) INFORMATION FOR SEQ ID NO:   16:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 16:

GGGAGGUCUC GUAGA                                                15

(2) INFORMATION FOR SEQ ID NO:   17:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 17:

GAGGUCUCGU AGACC                                                15

(2) INFORMATION FOR SEQ ID NO:   18:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 18:

GUCUCGUAGA CCGUG                                                15

(2) INFORMATION FOR SEQ ID NO:   19:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 19:

AGGACGUCAA GUUCC                                                15

(2) INFORMATION FOR SEQ ID NO:   20:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 20:

GUCAAGUUCC CGGGC                                                15

(2) INFORMATION FOR SEQ ID NO:   21:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 21:

UCAAGUUCCC GGGCG                                                15

(2) INFORMATION FOR SEQ ID NO:   22:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 22:

CGGUGGUCAG AUCGU                                                15

(2) INFORMATION FOR SEQ ID NO:   23:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 23:

CCCACGUUGG GUGUG                                                15

(2) INFORMATION FOR SEQ ID NO:   24:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 24:

CGCGACUAGG AAGAC                     15

(2) INFORMATION FOR SEQ ID NO: 25:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 25:

GAAGACUUCC GAACG                     15

(2) INFORMATION FOR SEQ ID NO: 26:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 26:

AAGACUUCCG AACGG                     15

(2) INFORMATION FOR SEQ ID NO: 27:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 27:

GAACGGUCGC AACCU                     15

(2) INFORMATION FOR SEQ ID NO: 28:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 28:

ACAACCUAUC CCCAA                     15

(2) INFORMATION FOR SEQ ID NO: 29:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 29:

AACCUAUCCC CAAGG                     15

(2) INFORMATION FOR SEQ ID NO: 30:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 30:

```
CAAGGCUCGC CGACC                                                        15

(2) INFORMATION FOR SEQ ID NO:   31:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 31:

CGAGGGUAGG GCCUG                                                        15

(2) INFORMATION FOR SEQ ID NO:   32:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 32:

CUGGGCUCAG CCUGG                                                        15

(2) INFORMATION FOR SEQ ID NO:   33:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 33:

CCUGGGUACC CUUGG                                                        15

(2) INFORMATION FOR SEQ ID NO:   34:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 34:

GUACCCUUGG CCCCU                                                        15

(2) INFORMATION FOR SEQ ID NO:   35:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 35:

GGCCCCUCUA UGGCA                                                        15

(2) INFORMATION FOR SEQ ID NO:   36:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 36:

CCCCUCUAUG GCAAU                                                        15
```

(2) INFORMATION FOR SEQ ID NO: 37:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 37:

GAUGGCUCCU GUCAC                                                15

(2) INFORMATION FOR SEQ ID NO: 38:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 38:

CUCCUGUCAC CCCGC                                                15

(2) INFORMATION FOR SEQ ID NO: 39:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 39:

CGCGGCUCCC GGCCU                                                15

(2) INFORMATION FOR SEQ ID NO: 40:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 40:

CCGGCCUAGU UGGGG                                                15

(2) INFORMATION FOR SEQ ID NO: 41:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 41:

GCCUAGUUGG GGCCC                                                15

(2) INFORMATION FOR SEQ ID NO: 42:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 42:

GCGCAAUCUG GGUAA                                                15

(2) INFORMATION FOR SEQ ID NO: 43:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 43:

GUAAGGUCAU CGAUA                                  15

(2) INFORMATION FOR SEQ ID NO: 44:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 44:

AGGUCAUCGA UACCC                                  15

(2) INFORMATION FOR SEQ ID NO: 45:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 45:

CAUCGAUACC CUCAC                                  15

(2) INFORMATION FOR SEQ ID NO: 46:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 46:

UGCGGCUUCG CCGAC                                  15

(2) INFORMATION FOR SEQ ID NO: 47:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 47:

GCGGCUUCGC CGACC                                  15

(2) INFORMATION FOR SEQ ID NO: 48:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 48:

AUGGGGUACA UUCCG                                  15

(2) INFORMATION FOR SEQ ID NO: 49:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 49:

GGUACAUUCC GCUCG                                     15

(2) INFORMATION FOR SEQ ID NO: 50:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 50:

GUACAUUCCG CUCGU                                     15

(2) INFORMATION FOR SEQ ID NO: 51:

(i) SEQUENCE CHARACTERISTICS:
        (A) LENGTH:       15
        (B) TYPE:         nucleic acid
        (C) STRANDEDNESS:  single
        (D) TOPOLOGY:     linear (xi) SEQUENCE DESCRIPTION: SEQ ID NO: 51:

UUCCGCUCGU CGGCG                                     15

(2) INFORMATION FOR SEQ ID NO: 52:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 52:

CGCUCGUCGG CGCCC                                     15

(2) INFORMATION FOR SEQ ID NO: 53:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 53:

CCCCCCUAGG GGGCG                                     15

(2) INFORMATION FOR SEQ ID NO: 54:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 54:

AUGGUGUCCG GGUUC                                     15

(2) INFORMATION FOR SEQ ID NO: 55:

```
        (i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 55:

UCCGGGUUCU GGAGG                                                    15

(2) INFORMATION FOR SEQ ID NO:  56:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 56:

CCGGGUUCUG GAGGA                                                    15

(2) INFORMATION FOR SEQ ID NO:  57:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 57:

GUGAACUACG CAACA                                                    15

(2) INFORMATION FOR SEQ ID NO:  58:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 58:

GGGAACUUGC CCGGU                                                    15

(2) INFORMATION FOR SEQ ID NO:  59:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 59:

GCCCGGUUGC UCUUU                                                    15

(2) INFORMATION FOR SEQ ID NO:  60:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 60:

GGUUGCUCUU UCUCU                                                    15

(2) INFORMATION FOR SEQ ID NO:  61:
```

```
            (i) SEQUENCE CHARACTERISTICS:
                  (A) LENGTH:          15
                  (B) TYPE:            nucleic acid
                  (C) STRANDEDNESS:    single
                  (D) TOPOLOGY:        linear (xi) SEQUENCE DESCRIPTION: SEQ ID NO: 61:

AUUGUGUAUG AGGCA                                                        15

(2) INFORMATION FOR SEQ ID NO:  62:

(i) SEQUENCE CHARACTERISTICS:
                  (A) LENGTH:          15
                  (B) TYPE:            nucleic acid
                  (C) STRANDEDNESS:    single
                  (D) TOPOLOGY:        linear (xi) SEQUENCE DESCRIPTION: SEQ ID NO: 62:

GCAUGAUCAU GCAUA                                                        15

(2) INFORMATION FOR SEQ ID NO:  63:

(i) SEQUENCE CHARACTERISTICS:
                  (A) LENGTH:          15
                  (B) TYPE:            nucleic acid
                  (C) STRANDEDNESS:    single
                  (D) TOPOLOGY:        linear (xi) SEQUENCE DESCRIPTION: SEQ ID NO: 63:

GGUGCGUACC CUGCG                                                        15

(2) INFORMATION FOR SEQ ID NO:  64:

(i) SEQUENCE CHARACTERISTICS:
                  (A) LENGTH:          15
                  (B) TYPE:            nucleic acid
                  (C) STRANDEDNESS:    single
                  (D) TOPOLOGY:        linear (xi) SEQUENCE DESCRIPTION: SEQ ID NO: 64:

CCUGCGUUCG GGAGA                                                        15

(2) INFORMATION FOR SEQ ID NO:  65:

(i) SEQUENCE CHARACTERISTICS:
                  (A) LENGTH:          15
                  (B) TYPE:            nucleic acid
                  (C) STRANDEDNESS:    single
                  (D) TOPOLOGY:        linear (xi) SEQUENCE DESCRIPTION: SEQ ID NO: 65:

CUGCGUUCGG GAGAA                                                        15

(2) INFORMATION FOR SEQ ID NO:  66:

(i) SEQUENCE CHARACTERISTICS:
                  (A) LENGTH:          15
                  (B) TYPE:            nucleic acid
                  (C) STRANDEDNESS:    single
                  (D) TOPOLOGY:        linear (xi) SEQUENCE DESCRIPTION: SEQ ID NO: 66:

AACGCCUCCC GUUGU                                                        15

(2) INFORMATION FOR SEQ ID NO:  67:

(i) SEQUENCE CHARACTERISTICS:
```

```
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 67:

CUCCCGUUGU UGGGU                                                        15

(2) INFORMATION FOR SEQ ID NO:   68:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 68:

CCGUUGUUGG GUAGC                                                        15

(2) INFORMATION FOR SEQ ID NO:   69:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 69:

GUUGGGUAGC GCUCA                                                        15

(2) INFORMATION FOR SEQ ID NO:   70:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 70:

GCCACGUCGA CUUGC                                                        15

(2) INFORMATION FOR SEQ ID NO:   71:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 71:

GUCGACUUGC UCGUU                                                        15

(2) INFORMATION FOR SEQ ID NO:   72:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 72:

ACUUGCUCGU UGGGG                                                        15

(2) INFORMATION FOR SEQ ID NO:   73:

(i) SEQUENCE CHARACTERISTICS:
            (A) LENGTH:         15
```

-continued

```
            (B) TYPE:           nucleic acid
            (C) STRANDEDNESS:   single
            (D) TOPOLOGY:       linear (xi) SEQUENCE DESCRIPTION: SEQ ID NO: 73:

UGCUCGUUGG GGCGG                                                  15

(2) INFORMATION FOR SEQ ID NO:   74:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 74:

GCCGCUUUCU GUUCC                                                  15

(2) INFORMATION FOR SEQ ID NO:   75:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 75:

CCGCUUUCUG UUCCG                                                  15

(2) INFORMATION FOR SEQ ID NO:   76:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 76:

UUUCUGUUCC GCCAU                                                  15

(2) INFORMATION FOR SEQ ID NO:   77:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 77:

UUCUGUUCCG CCAUG                                                  15

(2) INFORMATION FOR SEQ ID NO:   78:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 78:

GCCAUGUACG UGGGG                                                  15

(2) INFORMATION FOR SEQ ID NO:   79:

(i) SEQUENCE CHARACTERISTICS:
            (A) LENGTH:         15
            (B) TYPE:           nucleic acid
```

-continued

```
            (C) STRANDEDNESS:     single
            (D) TOPOLOGY:         linear (xi) SEQUENCE DESCRIPTION: SEQ ID NO: 79:

UGCGGAUCCG UUUUC                                                    15

(2) INFORMATION FOR SEQ ID NO:  80:

(i) SEQUENCE CHARACTERISTICS:
            (A) LENGTH:           15
            (B) TYPE:             nucleic acid
            (C) STRANDEDNESS:     single
            (D) TOPOLOGY:         linear (xi) SEQUENCE DESCRIPTION: SEQ ID NO: 80:

GAUCCGUUUU CCUCG                                                    15

(2) INFORMATION FOR SEQ ID NO:  81:

(i) SEQUENCE CHARACTERISTICS:
            (A) LENGTH:           15
            (B) TYPE:             nucleic acid
            (C) STRANDEDNESS:     single
            (D) TOPOLOGY:         linear (xi) SEQUENCE DESCRIPTION: SEQ ID NO: 81:

AUCCGUUUUC CUCGU                                                    15

(2) INFORMATION FOR SEQ ID NO:  82:

(i) SEQUENCE CHARACTERISTICS:
            (A) LENGTH:           15
            (B) TYPE:             nucleic acid
            (C) STRANDEDNESS:     single
            (D) TOPOLOGY:         linear (xi) SEQUENCE DESCRIPTION: SEQ ID NO: 82:

UCCGUUUUCC UCGUC                                                    15

(2) INFORMATION FOR SEQ ID NO:  83:

(i) SEQUENCE CHARACTERISTICS:
            (A) LENGTH:           15
            (B) TYPE:             nucleic acid
            (C) STRANDEDNESS:     single
            (D) TOPOLOGY:         linear (xi) SEQUENCE DESCRIPTION: SEQ ID NO: 83:

CCGUUUUCCU CGUCU                                                    15

(2) INFORMATION FOR SEQ ID NO:  84:

(i) SEQUENCE CHARACTERISTICS:
            (A) LENGTH:           15
            (B) TYPE:             nucleic acid
            (C) STRANDEDNESS:     single
            (D) TOPOLOGY:         linear (xi) SEQUENCE DESCRIPTION: SEQ ID NO: 84:

GCCAUGUAUC AGGUC                                                    15

(2) INFORMATION FOR SEQ ID NO:  85:

(i) SEQUENCE CHARACTERISTICS:
            (A) LENGTH:           15
            (B) TYPE:             nucleic acid
            (C) STRANDEDNESS:     single
```

```
        (D) TOPOLOGY:         linear (xi) SEQUENCE DESCRIPTION: SEQ ID NO: 85:

CAUGUAUCAG GUCAC                                                    15

(2) INFORMATION FOR SEQ ID NO: 86:

(i) SEQUENCE CHARACTERISTICS:
        (A) LENGTH:           15
        (B) TYPE:             nucleic acid
        (C) STRANDEDNESS:     single
        (D) TOPOLOGY:         linear (xi) SEQUENCE DESCRIPTION: SEQ ID NO: 86:

AUCAGGUCAC CGCAU                                                    15

(2) INFORMATION FOR SEQ ID NO: 87:

(i) SEQUENCE CHARACTERISTICS:
        (A) LENGTH:           15
        (B) TYPE:             nucleic acid
        (C) STRANDEDNESS:     single
        (D) TOPOLOGY:         linear (xi) SEQUENCE DESCRIPTION: SEQ ID NO: 87:

AAGCUGUCGU GGAUA                                                    15

(2) INFORMATION FOR SEQ ID NO: 88:

(i) SEQUENCE CHARACTERISTICS:
        (A) LENGTH:           15
        (B) TYPE:             nucleic acid
        (C) STRANDEDNESS:     single
        (D) TOPOLOGY:         linear (xi) SEQUENCE DESCRIPTION: SEQ ID NO: 88:

CGUGGAUAUG GUGGC                                                    15

(2) INFORMATION FOR SEQ ID NO: 89:

(i) SEQUENCE CHARACTERISTICS:
        (A) LENGTH:           15
        (B) TYPE:             nucleic acid
        (C) STRANDEDNESS:     single
        (D) TOPOLOGY:         linear (xi) SEQUENCE DESCRIPTION: SEQ ID NO: 89:

GGGGAGUCCU AGCGG                                                    15

(2) INFORMATION FOR SEQ ID NO: 90:

(i) SEQUENCE CHARACTERISTICS:
        (A) LENGTH:           15
        (B) TYPE:             nucleic acid
        (C) STRANDEDNESS:     single
        (D) TOPOLOGY:         linear (xi) SEQUENCE DESCRIPTION: SEQ ID NO: 90:

GAGUCCUAGC GGGCC                                                    15

(2) INFORMATION FOR SEQ ID NO: 91:

(i) SEQUENCE CHARACTERISTICS:
        (A) LENGTH:           15
        (B) TYPE:             nucleic acid
        (C) STRANDEDNESS:     single
        (D) TOPOLOGY:         linear
```

(xi) SEQUENCE DESCRIPTION: SEQ ID NO: 91:

CGGGCCUUGC CUACU                                                15

(2) INFORMATION FOR SEQ ID NO: 92:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 92:

CUUGCCUACU AUUCC                                                15

(2) INFORMATION FOR SEQ ID NO: 93:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 93:

GCCUACUAUU CCAUG                                                15

(2) INFORMATION FOR SEQ ID NO: 94:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 94:

CUACUAUUCC AUGGU                                                15

(2) INFORMATION FOR SEQ ID NO: 95:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 95:

UACUAUUCCA UGGUG                                                15

(2) INFORMATION FOR SEQ ID NO: 96:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 96:

GCUCCAUCGA CAAGU                                                15

(2) INFORMATION FOR SEQ ID NO: 97:

(i) SEQUENCE CHARACTERISTICS:
        (A) LENGTH:       15
        (B) TYPE:         nucleic acid
        (C) STRANDEDNESS: single
        (D) TOPOLOGY:     linear -continued (xi) SEQUENCE DESCRIPTION: SEQ ID NO: 97:

GACAAGUUCG CUCAG                                                    15

(2) INFORMATION FOR SEQ ID NO: 98:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 98:

ACAAGUUCGC UCAGG                                                    15

(2) INFORMATION FOR SEQ ID NO: 99:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 99:

GUUCGCUCAG GGAUG                                                    15

(2) INFORMATION FOR SEQ ID NO: 100:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 100:

GCCCCAUCAC CUAUA                                                    15

(2) INFORMATION FOR SEQ ID NO: 101:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 101:

AUCACCUAUA CCGAG                                                    15

(2) INFORMATION FOR SEQ ID NO: 102:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 102:

AGGCCUUACU GCUGG                                                    15

(2) INFORMATION FOR SEQ ID NO: 103:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 103:

CUGGCAUUAC GCACC                                                              15

(2) INFORMATION FOR SEQ ID NO:    104:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 104:

UGGCAUUACG CACCU                                                              15

(2) INFORMATION FOR SEQ ID NO:    105:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 105:

CGCACCUCGG CAGUG                                                              15

(2) INFORMATION FOR SEQ ID NO:    106:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 106:

GUGUGGUAUC GUACC                                                              15

(2) INFORMATION FOR SEQ ID NO:    107:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 107:

GUGGUAUCGU ACCUG                                                              15

(2) INFORMATION FOR SEQ ID NO:    108:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 108:

GUAUCGUACC UGCGU                                                              15

(2) INFORMATION FOR SEQ ID NO:    109:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 109:

```
CCUGCGUCGC AGGUG                                                    15

(2) INFORMATION FOR SEQ ID NO:   110:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 110:

GUGUGGUCCA GUGUA                                                    15

(2) INFORMATION FOR SEQ ID NO:   111:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 111:

GCCCUGUUGU AGUGG                                                    15

(2) INFORMATION FOR SEQ ID NO:   112:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 112:

CUGUUGUAGU GGGGA                                                    15

(2) INFORMATION FOR SEQ ID NO:   113:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 113:

GACCGAUCGG UCCGG                                                    15

(2) INFORMATION FOR SEQ ID NO:   114:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 114:

GAUCGGUCCG GUGCC                                                    15

(2) INFORMATION FOR SEQ ID NO:   115:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 115:

UGCCCCUACG UAUAA                                                    15
```

(2) INFORMATION FOR SEQ ID NO: 116:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 116:

CCUACGUAUA ACUGG                                                    15

(2) INFORMATION FOR SEQ ID NO: 117:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 117:

UACGUAUAAC UGGGG                                                    15

(2) INFORMATION FOR SEQ ID NO: 118:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 118:

AACUGGUUUG GCUGU                                                    15

(2) INFORMATION FOR SEQ ID NO: 119:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 119:

ACUGGUUUGG CUGUA                                                    15

(2) INFORMATION FOR SEQ ID NO: 120:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 120:

UGGCUGUACA UGGAU                                                    15

(2) INFORMATION FOR SEQ ID NO: 121:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 121:

GGGCCCUCCG UGCAA                                                    15

(2) INFORMATION FOR SEQ ID NO: 122:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 122:

GCAACAUCGG GGGGG                                                           15

(2) INFORMATION FOR SEQ ID NO: 123:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 123:

GGGGGGUCGG CAACC                                                           15

(2) INFORMATION FOR SEQ ID NO: 124:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 124:

GCAACCUCAC CUUGA                                                           15

(2) INFORMATION FOR SEQ ID NO: 125:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 125:

CUCACCUUGA CCUGC                                                           15

(2) INFORMATION FOR SEQ ID NO: 126:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 126:

GGCCACUUAC ACAAA                                                           15

(2) INFORMATION FOR SEQ ID NO: 127:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 127:

GCCACUUACA CAAAA                                                           15

(2) INFORMATION FOR SEQ ID NO: 128:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 128:

UGUGGCUCGG GGCCA     15

(2) INFORMATION FOR SEQ ID NO: 129:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 129:

CCAUGGUUAA CACCU     15

(2) INFORMATION FOR SEQ ID NO: 130:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 130:

CAUGGUUAAC ACCUA     15

(2) INFORMATION FOR SEQ ID NO: 131:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 131:

UUACCAUCUU UAAGG     15

(2) INFORMATION FOR SEQ ID NO: 132:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 132:

ACCAUCUUUA AGGUU     15

(2) INFORMATION FOR SEQ ID NO: 133:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 133:

ACAGGCUUAG UGCUG     15

(2) INFORMATION FOR SEQ ID NO: 134:

```
    (i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 134:

CAGGCUUAGU GCUGC                                                          15

(2) INFORMATION FOR SEQ ID NO:   135:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 135:

AGAGCGUUGC GACCU                                                          15

(2) INFORMATION FOR SEQ ID NO:   136:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 136:

GACAGAUCGG AGCUC                                                          15

(2) INFORMATION FOR SEQ ID NO:   137:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 137:

CGGAGCUCAG CCCGC                                                          15

(2) INFORMATION FOR SEQ ID NO:   138:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 138:

CUGCUGUCCA CGACA                                                          15

(2) INFORMATION FOR SEQ ID NO:   139:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 139:

UCCACCUCCA UCAGA                                                          15

(2) INFORMATION FOR SEQ ID NO:   140:
```

```
    (i) SEQUENCE CHARACTERISTICS:
         (A) LENGTH:          15
         (B) TYPE:            nucleic acid
         (C) STRANDEDNESS:    single
         (D) TOPOLOGY:        linear (xi) SEQUENCE DESCRIPTION: SEQ ID NO: 140:

CCUCCAUCAG AACAU                                                              15

(2) INFORMATION FOR SEQ ID NO:  141:

(i) SEQUENCE CHARACTERISTICS:
         (A) LENGTH:          15
         (B) TYPE:            nucleic acid
         (C) STRANDEDNESS:    single
         (D) TOPOLOGY:        linear (xi) SEQUENCE DESCRIPTION: SEQ ID NO: 141:

AGAACAUCGU GGACG                                                              15

(2) INFORMATION FOR SEQ ID NO:  142:

(i) SEQUENCE CHARACTERISTICS:
         (A) LENGTH:          15
         (B) TYPE:            nucleic acid
         (C) STRANDEDNESS:    single
         (D) TOPOLOGY:        linear (xi) SEQUENCE DESCRIPTION: SEQ ID NO: 142:

CGCGCGUCUG UGCCU                                                              15

(2) INFORMATION FOR SEQ ID NO:  143:

(i) SEQUENCE CHARACTERISTICS:
         (A) LENGTH:          15
         (B) TYPE:            nucleic acid
         (C) STRANDEDNESS:    single
         (D) TOPOLOGY:        linear (xi) SEQUENCE DESCRIPTION: SEQ ID NO: 143:

CCGCCCUAGA GAACC                                                              15

(2) INFORMATION FOR SEQ ID NO:  144:

(i) SEQUENCE CHARACTERISTICS:
         (A) LENGTH:          15
         (B) TYPE:            nucleic acid
         (C) STRANDEDNESS:    single
         (D) TOPOLOGY:        linear (xi) SEQUENCE DESCRIPTION: SEQ ID NO: 144:

UGGUGGUCCU CAACG                                                              15

(2) INFORMATION FOR SEQ ID NO:  145:

(i) SEQUENCE CHARACTERISTICS:
         (A) LENGTH:          15
         (B) TYPE:            nucleic acid
         (C) STRANDEDNESS:    single
         (D) TOPOLOGY:        linear (xi) SEQUENCE DESCRIPTION: SEQ ID NO: 145:

UGGUCCUCAA CGCGG                                                              15

(2) INFORMATION FOR SEQ ID NO:  146:

(i) SEQUENCE CHARACTERISTICS:
```

```
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 146:

GCCUGGUACA UCAAG                                                15

(2) INFORMATION FOR SEQ ID NO:   147:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 147:

GGUACAUCAA GGGCA                                                15

(2) INFORMATION FOR SEQ ID NO:   148:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 148:

GGCUGGUCCC UGGGG                                                15

(2) INFORMATION FOR SEQ ID NO:   149:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 149:

GCGGCAUAUG CUCUG                                                15

(2) INFORMATION FOR SEQ ID NO:   150:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 150:

AUAUGCUCUG UACGG                                                15

(2) INFORMATION FOR SEQ ID NO:   151:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 151:

GCUCUGUACG GCGUG                                                15

(2) INFORMATION FOR SEQ ID NO:   152:

(i) SEQUENCE CHARACTERISTICS:
        (A) LENGTH:         15
```

(B) TYPE:          nucleic acid
            (C) STRANDEDNESS:  single
            (D) TOPOLOGY:      linear (xi) SEQUENCE DESCRIPTION: SEQ ID NO: 152:

UCCUGCUCCU GCUGG                                                    15

(2) INFORMATION FOR SEQ ID NO:  153:

(i) SEQUENCE CHARACTERISTICS:
            (A) LENGTH:        15
            (B) TYPE:          nucleic acid
            (C) STRANDEDNESS:  single
            (D) TOPOLOGY:      linear (xi) SEQUENCE DESCRIPTION: SEQ ID NO: 153:

ACGGGCUUAC GCCAU                                                    15

(2) INFORMATION FOR SEQ ID NO:  154:

(i) SEQUENCE CHARACTERISTICS:
            (A) LENGTH:        15
            (B) TYPE:          nucleic acid
            (C) STRANDEDNESS:  single
            (D) TOPOLOGY:      linear (xi) SEQUENCE DESCRIPTION: SEQ ID NO: 154:

CGGGCUUACG CCAUG                                                    15

(2) INFORMATION FOR SEQ ID NO:  155:

(i) SEQUENCE CHARACTERISTICS:
            (A) LENGTH:        15
            (B) TYPE:          nucleic acid
            (C) STRANDEDNESS:  single
            (D) TOPOLOGY:      linear (xi) SEQUENCE DESCRIPTION: SEQ ID NO: 155:

UGGUGGUUAC AAUAC                                                    15

(2) INFORMATION FOR SEQ ID NO:  156:

(i) SEQUENCE CHARACTERISTICS:
            (A) LENGTH:        15
            (B) TYPE:          nucleic acid
            (C) STRANDEDNESS:  single
            (D) TOPOLOGY:      linear (xi) SEQUENCE DESCRIPTION: SEQ ID NO: 156:

GGUGGUUACA AUACU                                                    15

(2) INFORMATION FOR SEQ ID NO:  157:

(i) SEQUENCE CHARACTERISTICS:
            (A) LENGTH:        15
            (B) TYPE:          nucleic acid
            (C) STRANDEDNESS:  single
            (D) TOPOLOGY:      linear (xi) SEQUENCE DESCRIPTION: SEQ ID NO: 157:

UUACAAUACU UUAUC                                                    15

(2) INFORMATION FOR SEQ ID NO:  158:

(i) SEQUENCE CHARACTERISTICS:
            (A) LENGTH:        15
            (B) TYPE:          nucleic acid

```
            (C) STRANDEDNESS:    single
            (D) TOPOLOGY:        linear (xi) SEQUENCE DESCRIPTION: SEQ ID NO: 158:

CAAUACUUUA UCACC                                                         15

(2) INFORMATION FOR SEQ ID NO:    159:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 159:

AAUACUUUAU CACCA                                                         15

(2) INFORMATION FOR SEQ ID NO:    160:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 160:

GGCGCAUUUG UGCGU                                                         15

(2) INFORMATION FOR SEQ ID NO:    161:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 161:

GCGCAUUUGU GCGUG                                                         15

(2) INFORMATION FOR SEQ ID NO:    162:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 162:

UGUGGGUCCC CCCUC                                                         15

(2) INFORMATION FOR SEQ ID NO:    163:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 163:

CCCCCCUCUC AAUGU                                                         15

(2) INFORMATION FOR SEQ ID NO:    164:

(i) SEQUENCE CHARACTERISTICS:
            (A) LENGTH:          15
            (B) TYPE:            nucleic acid
            (C) STRANDEDNESS:    single
```

(D) TOPOLOGY:      linear (xi) SEQUENCE DESCRIPTION: SEQ ID NO: 164:

CCCCUCUCAA UGUCC                                                15

(2) INFORMATION FOR SEQ ID NO:   165:

(i) SEQUENCE CHARACTERISTICS:
         (A) LENGTH:        15
         (B) TYPE:          nucleic acid
         (C) STRANDEDNESS:  single
         (D) TOPOLOGY:      linear (xi) SEQUENCE DESCRIPTION: SEQ ID NO: 165:

UCAAUGUCCG GGGGG                                                15

(2) INFORMATION FOR SEQ ID NO:   166:

(i) SEQUENCE CHARACTERISTICS:
         (A) LENGTH:        15
         (B) TYPE:          nucleic acid
         (C) STRANDEDNESS:  single
         (D) TOPOLOGY:      linear (xi) SEQUENCE DESCRIPTION: SEQ ID NO: 166:

CGAUGCUAUC AUCCU                                                15

(2) INFORMATION FOR SEQ ID NO:   167:

(i) SEQUENCE CHARACTERISTICS:
         (A) LENGTH:        15
         (B) TYPE:          nucleic acid
         (C) STRANDEDNESS:  single
         (D) TOPOLOGY:      linear (xi) SEQUENCE DESCRIPTION: SEQ ID NO: 167:

AUGCUAUCAU CCUCC                                                15

(2) INFORMATION FOR SEQ ID NO:   168:

(i) SEQUENCE CHARACTERISTICS:
         (A) LENGTH:        15
         (B) TYPE:          nucleic acid
         (C) STRANDEDNESS:  single
         (D) TOPOLOGY:      linear (xi) SEQUENCE DESCRIPTION: SEQ ID NO: 168:

CUAUCAUCCU CCUCA                                                15

(2) INFORMATION FOR SEQ ID NO:   169:

(i) SEQUENCE CHARACTERISTICS:
         (A) LENGTH:        15
         (B) TYPE:          nucleic acid
         (C) STRANDEDNESS:  single
         (D) TOPOLOGY:      linear (xi) SEQUENCE DESCRIPTION: SEQ ID NO: 169:

UCAUCCUCCU CACAU                                                15

(2) INFORMATION FOR SEQ ID NO:   170:

(i) SEQUENCE CHARACTERISTICS:
         (A) LENGTH:        15
         (B) TYPE:          nucleic acid
         (C) STRANDEDNESS:  single
         (D) TOPOLOGY:      linear (xi) SEQUENCE DESCRIPTION: SEQ ID NO: 170:

UCCUCCUCAC AUGUG                                                    15

(2) INFORMATION FOR SEQ ID NO:   171:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 171:

CUGCCAUAAC UGCGA                                                    15

(2) INFORMATION FOR SEQ ID NO:   172:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 172:

AGGCCAUUAC GUCCA                                                    15

(2) INFORMATION FOR SEQ ID NO:   173:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 173:

GGCCAUUACG UCCAA                                                    15

(2) INFORMATION FOR SEQ ID NO:   174:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 174:

AUUACGUCCA AAUGG                                                    15

(2) INFORMATION FOR SEQ ID NO:   175:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 175:

AUGGCCUUCA UGAAG                                                    15

(2) INFORMATION FOR SEQ ID NO:   176:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 176:

UGGCCUUCAU GAAGC                                                    15

(2) INFORMATION FOR SEQ ID NO: 177:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 177:

CCCCGCUACA GGAUU                                                    15

(2) INFORMATION FOR SEQ ID NO: 178:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 178:

ACAGGAUUGG GCCCA                                                    15

(2) INFORMATION FOR SEQ ID NO: 179:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 179:

CGGGCCUACG AGACC                                                    15

(2) INFORMATION FOR SEQ ID NO: 180:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 180:

GAGACCUUGC GGUGG                                                    15

(2) INFORMATION FOR SEQ ID NO: 181:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 181:

AGCCCGUCGU CUUCU                                                    15

(2) INFORMATION FOR SEQ ID NO: 182:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 182:

```
CCGUCGUCUU CUCUG                                                    15

(2) INFORMATION FOR SEQ ID NO: 183:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 183:

GUCGUCUUCU CUGAC                                                    15

(2) INFORMATION FOR SEQ ID NO: 184:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 184:

CCAAGAUCAU CACCU                                                    15

(2) INFORMATION FOR SEQ ID NO: 185:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 185:

AGAUCAUCAC CUGGG                                                    15

(2) INFORMATION FOR SEQ ID NO: 186:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 186:

GGGACAUCAU CUUGG                                                    15

(2) INFORMATION FOR SEQ ID NO: 187:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 187:

ACAUCAUCUU GGGAC                                                    15

(2) INFORMATION FOR SEQ ID NO: 188:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 188:
```

```
AUCAUCUUGG GACUG                                                  15

(2) INFORMATION FOR SEQ ID NO: 189:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 189:

UGCCCGUCUC CGCCC                                                  15

(2) INFORMATION FOR SEQ ID NO: 190:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 190:

CCCGUCUCCG CCCGA                                                  15

(2) INFORMATION FOR SEQ ID NO: 191:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 191:

GGGAGAUACU UCUGG                                                  15

(2) INFORMATION FOR SEQ ID NO: 192:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 192:

GGCGACUCCU UGCCC                                                  15

(2) INFORMATION FOR SEQ ID NO: 193:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 193:

GACUCCUUGC CCCCA                                                  15

(2) INFORMATION FOR SEQ ID NO: 194:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 194:

CCCCCAUCAC GGCCU                                                  15
```

(2) INFORMATION FOR SEQ ID NO: 195:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 195:

CUAGCCUCAC AGGCC                                        15

(2) INFORMATION FOR SEQ ID NO: 196:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 196:

GGGAGGUUCA AGUGG                                        15

(2) INFORMATION FOR SEQ ID NO: 197:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 197:

GGAGGUUCAA GUGGU                                        15

(2) INFORMATION FOR SEQ ID NO: 198:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 198:

AAGUGGUUUC CACCG                                        15

(2) INFORMATION FOR SEQ ID NO: 199:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 199:

AGUGGUUUCC ACCGC                                        15

(2) INFORMATION FOR SEQ ID NO: 200:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 200:

GUGGUUUCCA CCGCA                                        15

(2) INFORMATION FOR SEQ ID NO: 201:

(i) SEQUENCE CHARACTERISTICS:
        (A) LENGTH:        15
        (B) TYPE:          nucleic acid
        (C) STRANDEDNESS:  single
        (D) TOPOLOGY:     linear (xi) SEQUENCE DESCRIPTION: SEQ ID NO: 201:

UGUGUGUUGG ACCGU                                          15

(2) INFORMATION FOR SEQ ID NO: 202:

(i) SEQUENCE CHARACTERISTICS:
        (A) LENGTH:        15
        (B) TYPE:          nucleic acid
        (C) STRANDEDNESS:  single
        (D) TOPOLOGY:     linear (xi) SEQUENCE DESCRIPTION: SEQ ID NO: 202:

GCCGGCUCAA AGACC                                          15

(2) INFORMATION FOR SEQ ID NO: 203:

(i) SEQUENCE CHARACTERISTICS:
        (A) LENGTH:        15
        (B) TYPE:          nucleic acid
        (C) STRANDEDNESS:  single
        (D) TOPOLOGY:     linear (xi) SEQUENCE DESCRIPTION: SEQ ID NO: 203:

AGACCCUAGC CGGCC                                          15

(2) INFORMATION FOR SEQ ID NO: 204:

(i) SEQUENCE CHARACTERISTICS:
        (A) LENGTH:        15
        (B) TYPE:          nucleic acid
        (C) STRANDEDNESS:  single
        (D) TOPOLOGY:     linear (xi) SEQUENCE DESCRIPTION: SEQ ID NO: 204:

UGCGCCUCCC GGGGC                                          15

(2) INFORMATION FOR SEQ ID NO: 205:

(i) SEQUENCE CHARACTERISTICS:
        (A) LENGTH:        15
        (B) TYPE:          nucleic acid
        (C) STRANDEDNESS:  single
        (D) TOPOLOGY:     linear (xi) SEQUENCE DESCRIPTION: SEQ ID NO: 205:

GGCGCGUUCC CUUAC                                          15

(2) INFORMATION FOR SEQ ID NO: 206:

(i) SEQUENCE CHARACTERISTICS:
        (A) LENGTH:        15
        (B) TYPE:          nucleic acid
        (C) STRANDEDNESS:  single
        (D) TOPOLOGY:     linear (xi) SEQUENCE DESCRIPTION: SEQ ID NO: 206:

GCGCGUUCCC UUACA                                          15

(2) INFORMATION FOR SEQ ID NO: 207:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 207:

GUUCCCUUAC ACCAU                                           15

(2) INFORMATION FOR SEQ ID NO: 208:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 208:

UUCCCUUACA CCAUG                                           15

(2) INFORMATION FOR SEQ ID NO: 209:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 209:

GGUAGCUCGG ACCUC                                         15

(2) INFORMATION FOR SEQ ID NO: 210:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 210:

CGGACCUCUA UCUGG                                         15

(2) INFORMATION FOR SEQ ID NO: 211:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 211:

GACCUCUAUC UGGUC                                         15

(2) INFORMATION FOR SEQ ID NO: 212:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 212:

CCUCUAUCUG GUCAC                                         15

(2) INFORMATION FOR SEQ ID NO: 213:

```
    (i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 213:

AUCUGGUCAC GAGAC                                                          15

(2) INFORMATION FOR SEQ ID NO: 214:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 214:

ACGUCAUUCC GGUGC                                                          15

(2) INFORMATION FOR SEQ ID NO: 215:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 215:

CGUCAUUCCG GUGCG                                                          15

(2) INFORMATION FOR SEQ ID NO: 216:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 216:

UGACGGUCGG GGGAG                                                          15

(2) INFORMATION FOR SEQ ID NO: 217:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 217:

GGAGCCUACU GUCCC                                                          15

(2) INFORMATION FOR SEQ ID NO: 218:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 218:

CUACUGUCCC CCAGA                                                          15

(2) INFORMATION FOR SEQ ID NO: 219:
```

```
    (i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 219:

GGCUCUUCGG GUGGC                                                    15

(2) INFORMATION FOR SEQ ID NO: 220:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 220:

CACUGCUCUG CCCUU                                                    15

(2) INFORMATION FOR SEQ ID NO: 221:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 221:

CUGCCCUUCG GGGCA                                                    15

(2) INFORMATION FOR SEQ ID NO: 222:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 222:

UGCCCUUCGG GGCAC                                                    15

(2) INFORMATION FOR SEQ ID NO: 223:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 223:

ACGCUGUAGG CAUCU                                                    15

(2) INFORMATION FOR SEQ ID NO: 224:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 224:

UAGGCAUCUU CCGGG                                                    15

(2) INFORMATION FOR SEQ ID NO: 225:

(i) SEQUENCE CHARACTERISTICS:
```

```
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 225:

GGCAUCUUCC GGGCU                                                        15

(2) INFORMATION FOR SEQ ID NO:   226:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 226:

GCAUCUUCCG GGCUG                                                        15

(2) INFORMATION FOR SEQ ID NO:   227:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 227:

GGGGGGUUGC GAAGG                                                        15

(2) INFORMATION FOR SEQ ID NO:   228:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 228:

GAGCACUAAA GUGCC                                                        15

(2) INFORMATION FOR SEQ ID NO:   229:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 229:

GCUGCGUACG CAGCC                                                        15

(2) INFORMATION FOR SEQ ID NO:   230:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 230:

CAAGGGUACA AGGUA                                                        15

(2) INFORMATION FOR SEQ ID NO:   231:

(i) SEQUENCE CHARACTERISTICS:
        (A) LENGTH:          15
```

```
            (B) TYPE:           nucleic acid
            (C) STRANDEDNESS:   single
            (D) TOPOLOGY:       linear (xi) SEQUENCE DESCRIPTION: SEQ ID NO: 231:

CAUCUGUUGC CGCCA                                                    15

(2) INFORMATION FOR SEQ ID NO:   232:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 232:

CCAACAUCAG AACUG                                                    15

(2) INFORMATION FOR SEQ ID NO:   233:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 233:

CUGGGGUAAG GACCA                                                    15

(2) INFORMATION FOR SEQ ID NO:   234:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 234:

UCCACCUAUG GUAAG                                                    15

(2) INFORMATION FOR SEQ ID NO:   235:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 235:

CUAUGGUAAG UUCCU                                                    15

(2) INFORMATION FOR SEQ ID NO:   236:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 236:

GGUAAGUUCC UUGCC                                                    15

(2) INFORMATION FOR SEQ ID NO:   237:

(i) SEQUENCE CHARACTERISTICS:
            (A) LENGTH:         15
            (B) TYPE:           nucleic acid
```

```
          (C) STRANDEDNESS:    single
          (D) TOPOLOGY:        linear (xi) SEQUENCE DESCRIPTION: SEQ ID NO: 237:

GUAAGUUCCU UGCCG                                                          15

(2) INFORMATION FOR SEQ ID NO:  238:

(i) SEQUENCE CHARACTERISTICS:
          (A) LENGTH:          15
          (B) TYPE:            nucleic acid
          (C) STRANDEDNESS:    single
          (D) TOPOLOGY:        linear (xi) SEQUENCE DESCRIPTION: SEQ ID NO: 238:

AGUUCCUUGC CGACG                                                          15

(2) INFORMATION FOR SEQ ID NO:  239:

(i) SEQUENCE CHARACTERISTICS:
          (A) LENGTH:          15
          (B) TYPE:            nucleic acid
          (C) STRANDEDNESS:    single
          (D) TOPOLOGY:        linear (xi) SEQUENCE DESCRIPTION: SEQ ID NO: 239:

AUAUCAUAAU AUGUG                                                          15

(2) INFORMATION FOR SEQ ID NO:  240:

(i) SEQUENCE CHARACTERISTICS:
          (A) LENGTH:          15
          (B) TYPE:            nucleic acid
          (C) STRANDEDNESS:    single
          (D) TOPOLOGY:        linear (xi) SEQUENCE DESCRIPTION: SEQ ID NO: 240:

UCAUAAUAUG UGAUG                                                          15

(2) INFORMATION FOR SEQ ID NO:  241:

(i) SEQUENCE CHARACTERISTICS:
          (A) LENGTH:          15
          (B) TYPE:            nucleic acid
          (C) STRANDEDNESS:    single
          (D) TOPOLOGY:        linear (xi) SEQUENCE DESCRIPTION: SEQ ID NO: 241:

GCACAGUCCU GGACC                                                          15

(2) INFORMATION FOR SEQ ID NO:  242:

(i) SEQUENCE CHARACTERISTICS:
          (A) LENGTH:          15
          (B) TYPE:            nucleic acid
          (C) STRANDEDNESS:    single
          (D) TOPOLOGY:        linear (xi) SEQUENCE DESCRIPTION: SEQ ID NO: 242:

CGCGGCUCGU CGUGC                                                          15

(2) INFORMATION FOR SEQ ID NO:  243:

(i) SEQUENCE CHARACTERISTICS:
          (A) LENGTH:          15
          (B) TYPE:            nucleic acid
          (C) STRANDEDNESS:    single
```

(D) TOPOLOGY:      linear (xi) SEQUENCE DESCRIPTION: SEQ ID NO: 243:

GGCUCGUCGU GCUCG                                                           15

(2) INFORMATION FOR SEQ ID NO: 244:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 244:

UCGUGCUCGC CACCG                                                           15

(2) INFORMATION FOR SEQ ID NO: 245:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 245:

CCCAAAUAUU GAGGA                                                           15

(2) INFORMATION FOR SEQ ID NO: 246:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 246:

GCUCUGUCCA ACACU                                                           15

(2) INFORMATION FOR SEQ ID NO: 247:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 247:

GAGAGAUCCC CUUCU                                                           15

(2) INFORMATION FOR SEQ ID NO: 248:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 248:

AGGCCAUCCC CCUCG                                                           15

(2) INFORMATION FOR SEQ ID NO: 249:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 249:

UCCCCCUCGA GGCCA                                                    15

(2) INFORMATION FOR SEQ ID NO:   250:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 250:

AGGCCAUCAA GGGGG                                                    15

(2) INFORMATION FOR SEQ ID NO:   251:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 251:

UGCCACUCCA AGAAG                                                    15

(2) INFORMATION FOR SEQ ID NO:   252:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 252:

UCGGAAUCAA UGCCG                                                    15

(2) INFORMATION FOR SEQ ID NO:   253:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 253:

AUGCCGUAGC GUAUU                                                    15

(2) INFORMATION FOR SEQ ID NO:   254:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 254:

GUAGCGUAUU ACCGG                                                    15

(2) INFORMATION FOR SEQ ID NO:   255:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 255:

AGCGUAUUAC CGGGG                                                        15

(2) INFORMATION FOR SEQ ID NO:   256:

(i) SEQUENCE CHARACTERISTICS:
         (A) LENGTH:         15
         (B) TYPE:           nucleic acid
         (C) STRANDEDNESS:   single
         (D) TOPOLOGY:       linear (xi) SEQUENCE DESCRIPTION: SEQ ID NO: 256:

GCGUAUUACC GGGGU                                                        15

(2) INFORMATION FOR SEQ ID NO:   257:

(i) SEQUENCE CHARACTERISTICS:
         (A) LENGTH:         15
         (B) TYPE:           nucleic acid
         (C) STRANDEDNESS:   single
         (D) TOPOLOGY:       linear (xi) SEQUENCE DESCRIPTION: SEQ ID NO:   257:

UGUCCGUCAU ACCGA                                                        15

(2) INFORMATION FOR SEQ ID NO:   258:

(i) SEQUENCE CHARACTERISTICS:
         (A) LENGTH:         15
         (B) TYPE:           nucleic acid
         (C) STRANDEDNESS:   single
         (D) TOPOLOGY:       linear (xi) SEQUENCE DESCRIPTION: SEQ ID NO: 258:

CCGUCAUACC GACUA                                                        15

(2) INFORMATION FOR SEQ ID NO:   259:

(i) SEQUENCE CHARACTERISTICS:
         (A) LENGTH:         15
         (B) TYPE:           nucleic acid
         (C) STRANDEDNESS:   single
         (D) TOPOLOGY:       linear (xi) SEQUENCE DESCRIPTION: SEQ ID NO: 259:

ACCGACUAGC GGAGA                                                        15

(2) INFORMATION FOR SEQ ID NO:   260:

(i) SEQUENCE CHARACTERISTICS:
         (A) LENGTH:         15
         (B) TYPE:           nucleic acid
         (C) STRANDEDNESS:   single
         (D) TOPOLOGY:       linear (xi) SEQUENCE DESCRIPTION: SEQ ID NO: 260:

ACGGGCUACA CCGGU                                                        15

(2) INFORMATION FOR SEQ ID NO:   261:

(i) SEQUENCE CHARACTERISTICS:
         (A) LENGTH:         15
         (B) TYPE:           nucleic acid
         (C) STRANDEDNESS:   single
         (D) TOPOLOGY:       linear (xi) SEQUENCE DESCRIPTION: SEQ ID NO: 261:

CGGUGAUCGA CUGCA                                                    15

(2) INFORMATION FOR SEQ ID NO: 262:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 262:

GCGGUGUCGC GCUCA                                                    15

(2) INFORMATION FOR SEQ ID NO: 263:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 263:

UCGCGCUCAC AACGG                                                    15

(2) INFORMATION FOR SEQ ID NO: 264:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 264:

CUGUGCUUGG UAUGA                                                    15

(2) INFORMATION FOR SEQ ID NO: 265:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 265:

GCUUGGUAUG AGCUC                                                    15

(2) INFORMATION FOR SEQ ID NO: 266:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 266:

AUGAGCUCAC GCCCG                                                    15

(2) INFORMATION FOR SEQ ID NO: 267:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 267:

UGAGACUACA GUCAG								15

(2) INFORMATION FOR SEQ ID NO: 268:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 268:

CUACAGUCAG GUUGC								15

(2) INFORMATION FOR SEQ ID NO: 269:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 269:

GUCAGGUUGC GGGCU								15

(2) INFORMATION FOR SEQ ID NO: 270:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 270:

GCGGGCUUAC CUGAA								15

(2) INFORMATION FOR SEQ ID NO: 271:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 271:

CGGGCUUACC UGAAU								15

(2) INFORMATION FOR SEQ ID NO: 272:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 272:

CCUGAAUACA CCAGG								15

(2) INFORMATION FOR SEQ ID NO: 273:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 273:

CCAGGGUUGC CCGUC								15

(2) INFORMATION FOR SEQ ID NO: 274:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 274:

UGCCCGUCUG CCAGG                                                15

(2) INFORMATION FOR SEQ ID NO: 275:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 275:

GGACCAUCUG GAGUU                                                15

(2) INFORMATION FOR SEQ ID NO: 276:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 276:

ACCUGGUAGC AUACC                                                15

(2) INFORMATION FOR SEQ ID NO: 277:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 277:

GUAGCAUACC AAGCC                                                15

(2) INFORMATION FOR SEQ ID NO: 278:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 278:

CAGGGCUCAG GCUCC                                                15

(2) INFORMATION FOR SEQ ID NO: 279:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 279:

CUGCUGUAUA GGCUA                                                15

```
(2) INFORMATION FOR SEQ ID NO:   280:

(i) SEQUENCE CHARACTERISTICS:
        (A) LENGTH:           15
        (B) TYPE:             nucleic acid
        (C) STRANDEDNESS:     single
        (D) TOPOLOGY:         linear (xi) SEQUENCE DESCRIPTION: SEQ ID NO: 280:

GCUGUAUAGG CUAGG                                                      15

(2) INFORMATION FOR SEQ ID NO:   281:

(i) SEQUENCE CHARACTERISTICS:
        (A) LENGTH:           15
        (B) TYPE:             nucleic acid
        (C) STRANDEDNESS:     single
        (D) TOPOLOGY:         linear (xi) SEQUENCE DESCRIPTION: SEQ ID NO: 281:

UGGAGGUCGU CACUA                                                      15

(2) INFORMATION FOR SEQ ID NO:   282:

(i) SEQUENCE CHARACTERISTICS:
        (A) LENGTH:           15
        (B) TYPE:             nucleic acid
        (C) STRANDEDNESS:     single
        (D) TOPOLOGY:         linear (xi) SEQUENCE DESCRIPTION: SEQ ID NO: 282:

AGGUCGUCAC UAGCA                                                      15

(2) INFORMATION FOR SEQ ID NO:   283:

(i) SEQUENCE CHARACTERISTICS:
        (A) LENGTH:           15
        (B) TYPE:             nucleic acid
        (C) STRANDEDNESS:     single
        (D) TOPOLOGY:         linear (xi) SEQUENCE DESCRIPTION: SEQ ID NO: 283:

CGUCACUAGC ACCUG                                                      15

(2) INFORMATION FOR SEQ ID NO:   284:

(i) SEQUENCE CHARACTERISTICS:
        (A) LENGTH:           15
        (B) TYPE:             nucleic acid
        (C) STRANDEDNESS:     single
        (D) TOPOLOGY:         linear (xi) SEQUENCE DESCRIPTION: SEQ ID NO: 284:

UGCUGGUAGG CGGAG                                                      15

(2) INFORMATION FOR SEQ ID NO:   285:

(i) SEQUENCE CHARACTERISTICS:
        (A) LENGTH:           15
        (B) TYPE:             nucleic acid
        (C) STRANDEDNESS:     single
        (D) TOPOLOGY:         linear (xi) SEQUENCE DESCRIPTION: SEQ ID NO: 285:

GCGGAGUCCU UGCAG                                                      15
```

(2) INFORMATION FOR SEQ ID NO: 286:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 286:

GAGUCCUUGC AGCUC                                                                   15

(2) INFORMATION FOR SEQ ID NO: 287:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 287:

GCCGCAUAUU GCCUG                                                                   15

(2) INFORMATION FOR SEQ ID NO: 288:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 288:

CGCAUAUUGC CUGAC                                                                   15

(2) INFORMATION FOR SEQ ID NO: 289:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 289:

AACCGGUAGU GUGGU                                                                   15

(2) INFORMATION FOR SEQ ID NO: 290:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 290:

GUAGGAUCAU UUUGU                                                                   15

(2) INFORMATION FOR SEQ ID NO: 291:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 291:

CGGCUGUUGU UCCCG                                                                   15

(2) INFORMATION FOR SEQ ID NO: 292:

(i) SEQUENCE CHARACTERISTICS:
            (A) LENGTH:        15
            (B) TYPE:          nucleic acid
            (C) STRANDEDNESS:  single
            (D) TOPOLOGY:      linear (xi) SEQUENCE DESCRIPTION: SEQ ID NO: 292:

CUGUUGUUCC CGACA                                                          15

(2) INFORMATION FOR SEQ ID NO: 293:

(i) SEQUENCE CHARACTERISTICS:
            (A) LENGTH:        15
            (B) TYPE:          nucleic acid
            (C) STRANDEDNESS:  single
            (D) TOPOLOGY:      linear (xi) SEQUENCE DESCRIPTION: SEQ ID NO: 293:

UGUUGUUCCC GACAG                                                          15

(2) INFORMATION FOR SEQ ID NO: 294:

(i) SEQUENCE CHARACTERISTICS:
            (A) LENGTH:        15
            (B) TYPE:          nucleic acid
            (C) STRANDEDNESS:  single
            (D) TOPOLOGY:      linear (xi) SEQUENCE DESCRIPTION: SEQ ID NO: 294:

GAGCAGUUCA AGCAG                                                          15

(2) INFORMATION FOR SEQ ID NO: 295:

(i) SEQUENCE CHARACTERISTICS:
            (A) LENGTH:        15
            (B) TYPE:          nucleic acid
            (C) STRANDEDNESS:  single
            (D) TOPOLOGY:      linear (xi) SEQUENCE DESCRIPTION: SEQ ID NO: 295:

AGCAGUUCAA GCAGA                                                          15

(2) INFORMATION FOR SEQ ID NO: 296:

(i) SEQUENCE CHARACTERISTICS:
            (A) LENGTH:        15
            (B) TYPE:          nucleic acid
            (C) STRANDEDNESS:  single
            (D) TOPOLOGY:      linear (xi) SEQUENCE DESCRIPTION: SEQ ID NO: 296:

CGCUGCUCCC GUGGU                                                          15

(2) INFORMATION FOR SEQ ID NO: 297:

(i) SEQUENCE CHARACTERISTICS:
            (A) LENGTH:        15
            (B) TYPE:          nucleic acid
            (C) STRANDEDNESS:  single
            (D) TOPOLOGY:      linear (xi) SEQUENCE DESCRIPTION: SEQ ID NO: 297:

GUGGAGUCCA GGUGG                                                          15

(2) INFORMATION FOR SEQ ID NO: 298:

```
    (i) SEQUENCE CHARACTERISTICS:
         (A) LENGTH:         15
         (B) TYPE:           nucleic acid
         (C) STRANDEDNESS:   single
         (D) TOPOLOGY:       linear (xi) SEQUENCE DESCRIPTION: SEQ ID NO: 298:

GGGCCCUUGA GGCCU                                                        15

(2) INFORMATION FOR SEQ ID NO: 299:

(i) SEQUENCE CHARACTERISTICS:
         (A) LENGTH:         15
         (B) TYPE:           nucleic acid
         (C) STRANDEDNESS:   single
         (D) TOPOLOGY:       linear (xi) SEQUENCE DESCRIPTION: SEQ ID NO: 299:

GAGGCCUUCU GGGCA                                                        15

(2) INFORMATION FOR SEQ ID NO: 300:

(i) SEQUENCE CHARACTERISTICS:
         (A) LENGTH:         15
         (B) TYPE:           nucleic acid
         (C) STRANDEDNESS:   single
         (D) TOPOLOGY:       linear (xi) SEQUENCE DESCRIPTION: SEQ ID NO: 300:

AGGCCUUCUG GGCAA                                                        15

(2) INFORMATION FOR SEQ ID NO: 301:

(i) SEQUENCE CHARACTERISTICS:
         (A) LENGTH:         15
         (B) TYPE:           nucleic acid
         (C) STRANDEDNESS:   single
         (D) TOPOLOGY:       linear (xi) SEQUENCE DESCRIPTION: SEQ ID NO: 301:

GCAGGCUUAU CCACU                                                        15

(2) INFORMATION FOR SEQ ID NO: 302:

(i) SEQUENCE CHARACTERISTICS:
         (A) LENGTH:         15
         (B) TYPE:           nucleic acid
         (C) STRANDEDNESS:   single
         (D) TOPOLOGY:       linear (xi) SEQUENCE DESCRIPTION: SEQ ID NO: 302:

CAGGCUUAUC CACUC                                                        15

(2) INFORMATION FOR SEQ ID NO: 303:

(i) SEQUENCE CHARACTERISTICS:
         (A) LENGTH:         15
         (B) TYPE:           nucleic acid
         (C) STRANDEDNESS:   single
         (D) TOPOLOGY:       linear (xi) SEQUENCE DESCRIPTION: SEQ ID NO: 303:

CUCCUGUUCA ACAUC                                                        15

(2) INFORMATION FOR SEQ ID NO: 304:

(i) SEQUENCE CHARACTERISTICS:
```

```
          (A) LENGTH:         15
          (B) TYPE:           nucleic acid
          (C) STRANDEDNESS:   single
          (D) TOPOLOGY:       linear (xi) SEQUENCE DESCRIPTION: SEQ ID NO: 304:

UCCUGUUCAA CAUCU                                                        15

(2) INFORMATION FOR SEQ ID NO:   305:

(i) SEQUENCE CHARACTERISTICS:
          (A) LENGTH:         15
          (B) TYPE:           nucleic acid
          (C) STRANDEDNESS:   single
          (D) TOPOLOGY:       linear (xi) SEQUENCE DESCRIPTION: SEQ ID NO: 305:

CUCAACUCGC UCCUC                                                        15

(2) INFORMATION FOR SEQ ID NO:   306:

(i) SEQUENCE CHARACTERISTICS:
          (A) LENGTH:         15
          (B) TYPE:           nucleic acid
          (C) STRANDEDNESS:   single
          (D) TOPOLOGY:       linear (xi) SEQUENCE DESCRIPTION: SEQ ID NO: 306:

ACUCGCUCCU CCCAG                                                        15

(2) INFORMATION FOR SEQ ID NO:   307:

(i) SEQUENCE CHARACTERISTICS:
          (A) LENGTH:         15
          (B) TYPE:           nucleic acid
          (C) STRANDEDNESS:   single
          (D) TOPOLOGY:       linear (xi) SEQUENCE DESCRIPTION: SEQ ID NO: 307:

GCUGCUUCGG CCUUC                                                        15

(2) INFORMATION FOR SEQ ID NO:   308:

(i) SEQUENCE CHARACTERISTICS:
          (A) LENGTH:         15
          (B) TYPE:           nucleic acid
          (C) STRANDEDNESS:   single
          (D) TOPOLOGY:       linear (xi) SEQUENCE DESCRIPTION: SEQ ID NO: 308:

UCGGCCUUCG UGGGC                                                        15

(2) INFORMATION FOR SEQ ID NO:   309:

(i) SEQUENCE CHARACTERISTICS:
          (A) LENGTH:         15
          (B) TYPE:           nucleic acid
          (C) STRANDEDNESS:   single
          (D) TOPOLOGY:       linear (xi) SEQUENCE DESCRIPTION: SEQ ID NO: 309:

CGGCCUUCGU GGGCG                                                        15

(2) INFORMATION FOR SEQ ID NO:   310:

(i) SEQUENCE CHARACTERISTICS:
          (A) LENGTH:         15
```

```
            (B) TYPE:            nucleic acid
            (C) STRANDEDNESS:    single
            (D) TOPOLOGY:        linear (xi) SEQUENCE DESCRIPTION: SEQ ID NO: 310:

CCGGCAUUGC CGGUG                                                15

(2) INFORMATION FOR SEQ ID NO:   311:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 311:

CGGCCAUUGG CAGCA                                                15

(2) INFORMATION FOR SEQ ID NO:   312:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 312:

GCAGCAUAGG CCUUG                                                15

(2) INFORMATION FOR SEQ ID NO:   313:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 313:

UAGGCCUUGG GAAGG                                                15

(2) INFORMATION FOR SEQ ID NO:   314:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 314:

GCGGGCUAUG GAGCG                                                15

(2) INFORMATION FOR SEQ ID NO:   315:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 315:

GUGCACUCGU GGCUU                                                15

(2) INFORMATION FOR SEQ ID NO:   316:

(i) SEQUENCE CHARACTERISTICS:
            (A) LENGTH:          15
            (B) TYPE:            nucleic acid
```

```
        (C) STRANDEDNESS:     single
        (D) TOPOLOGY:         linear (xi) SEQUENCE DESCRIPTION: SEQ ID NO: 316:

CGUGGCUUUU AAGGU                                                                15

(2) INFORMATION FOR SEQ ID NO: 317:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 317:

GUGGCUUUUA AGGUC                                                                15

(2) INFORMATION FOR SEQ ID NO: 318:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 318:

UGGCUUUUAA GGUCA                                                                15

(2) INFORMATION FOR SEQ ID NO: 319:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 319:

GGCUUUUAAG GUCAU                                                                15

(2) INFORMATION FOR SEQ ID NO: 320:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 320:

UUAAGGUCAU GAGCG                                                                15

(2) INFORMATION FOR SEQ ID NO: 321:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 321:

GCGCCCUCCG CCGAG                                                                15

(2) INFORMATION FOR SEQ ID NO: 322:

(i) SEQUENCE CHARACTERISTICS:
        (A) LENGTH:          15
        (B) TYPE:            nucleic acid
        (C) STRANDEDNESS:    single
```

```
          (D) TOPOLOGY:       linear (xi) SEQUENCE DESCRIPTION: SEQ ID NO: 322:

ACCUGGUUAA CUUGC                                                    15

(2) INFORMATION FOR SEQ ID NO: 323:

(i) SEQUENCE CHARACTERISTICS:
          (A) LENGTH:         15
          (B) TYPE:           nucleic acid
          (C) STRANDEDNESS:   single
          (D) TOPOLOGY:       linear (xi) SEQUENCE DESCRIPTION: SEQ ID NO: 323:

CCUGGUUAAC UUGCU                                                    15

(2) INFORMATION FOR SEQ ID NO: 324:

(i) SEQUENCE CHARACTERISTICS:
          (A) LENGTH:         15
          (B) TYPE:           nucleic acid
          (C) STRANDEDNESS:   single
          (D) TOPOLOGY:       linear (xi) SEQUENCE DESCRIPTION: SEQ ID NO: 324:

ACUUGCUCCC UGCCA                                                    15

(2) INFORMATION FOR SEQ ID NO: 325:

(i) SEQUENCE CHARACTERISTICS:
          (A) LENGTH:         15
          (B) TYPE:           nucleic acid
          (C) STRANDEDNESS:   single
          (D) TOPOLOGY:       linear (xi) SEQUENCE DESCRIPTION: SEQ ID NO: 325:

AUCCUCUCCC CCGGC                                                    15

(2) INFORMATION FOR SEQ ID NO: 326:

(i) SEQUENCE CHARACTERISTICS:
          (A) LENGTH:         15
          (B) TYPE:           nucleic acid
          (C) STRANDEDNESS:   single
          (D) TOPOLOGY:       linear (xi) SEQUENCE DESCRIPTION: SEQ ID NO: 326:

CCCUGGUCGU CGGGG                                                    15

(2) INFORMATION FOR SEQ ID NO: 327:

(i) SEQUENCE CHARACTERISTICS:
          (A) LENGTH:         15
          (B) TYPE:           nucleic acid
          (C) STRANDEDNESS:   single
          (D) TOPOLOGY:       linear (xi) SEQUENCE DESCRIPTION: SEQ ID NO: 327:

UGGUCGUCGG GGUCG                                                    15

(2) INFORMATION FOR SEQ ID NO: 328:

(i) SEQUENCE CHARACTERISTICS:
          (A) LENGTH:         15
          (B) TYPE:           nucleic acid
          (C) STRANDEDNESS:   single
          (D) TOPOLOGY:       linear
```

(xi) SEQUENCE DESCRIPTION: SEQ ID NO: 328:

UCGGGUCGU GUGUG                                                    15

(2) INFORMATION FOR SEQ ID NO:   329:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 329:

CAGCAAUCCU GCGUC                                                   15

(2) INFORMATION FOR SEQ ID NO:   330:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 330:

CCUGCGUCGG CACGU                                                   15

(2) INFORMATION FOR SEQ ID NO:   331:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 331:

AUAGCGUUCG CUUCG                                                   15

(2) INFORMATION FOR SEQ ID NO:   332:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 332:

UAGCGUUCGC UUCGC                                                   15

(2) INFORMATION FOR SEQ ID NO:   333:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 333:

GUUCGCUUCG CGGGG                                                   15

(2) INFORMATION FOR SEQ ID NO:   334:

(i) SEQUENCE CHARACTERISTICS:
        (A) LENGTH:        15
        (B) TYPE:          nucleic acid
        (C) STRANDEDNESS:  single
        (D) TOPOLOGY:      linear

```
        (xi) SEQUENCE DESCRIPTION: SEQ ID NO: 334:

ACGGCAUCAU GCAAA                                                    15

(2) INFORMATION FOR SEQ ID NO:   335:

(i) SEQUENCE CHARACTERISTICS:
          (A) LENGTH:         15
          (B) TYPE:           nucleic acid
          (C) STRANDEDNESS:   single
          (D) TOPOLOGY:       linear (xi) SEQUENCE DESCRIPTION: SEQ ID NO: 335:

CCGAACUAUU CCAGG                                                    15

(2) INFORMATION FOR SEQ ID NO:   336:

(i) SEQUENCE CHARACTERISTICS:
          (A) LENGTH:         15
          (B) TYPE:           nucleic acid
          (C) STRANDEDNESS:   single
          (D) TOPOLOGY:       linear (xi) SEQUENCE DESCRIPTION: SEQ ID NO: 336:

GAACUAUUCC AGGGC                                                    15

(2) INFORMATION FOR SEQ ID NO:   337:

(i) SEQUENCE CHARACTERISTICS:
          (A) LENGTH:         15
          (B) TYPE:           nucleic acid
          (C) STRANDEDNESS:   single
          (D) TOPOLOGY:       linear (xi) SEQUENCE DESCRIPTION: SEQ ID NO: 337:

AACUAUUCCA GGGCG                                                    15

(2) INFORMATION FOR SEQ ID NO:   338:

(i) SEQUENCE CHARACTERISTICS:
          (A) LENGTH:         15
          (B) TYPE:           nucleic acid
          (C) STRANDEDNESS:   single
          (D) TOPOLOGY:       linear (xi) SEQUENCE DESCRIPTION: SEQ ID NO: 338:

GGGGACUUCC ACUAC                                                    15

(2) INFORMATION FOR SEQ ID NO:   339:

(i) SEQUENCE CHARACTERISTICS:
          (A) LENGTH:         15
          (B) TYPE:           nucleic acid
          (C) STRANDEDNESS:   single
          (D) TOPOLOGY:       linear (xi) SEQUENCE DESCRIPTION: SEQ ID NO: 339:

GGGACUUCCA CUACG                                                    15

(2) INFORMATION FOR SEQ ID NO:   340:

(i) SEQUENCE CHARACTERISTICS:
          (A) LENGTH:         15
          (B) TYPE:           nucleic acid
          (C) STRANDEDNESS:   single
          (D) TOPOLOGY:       linear (xi) SEQUENCE DESCRIPTION: SEQ ID NO: 340:
```

UUCCACUACG UGACG                                                    15

(2) INFORMATION FOR SEQ ID NO:    341:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 341:

ACAACGUAAA AUGCC                                                    15

(2) INFORMATION FOR SEQ ID NO:    342:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 342:

CCCGAAUUCU UCACC                                                    15

(2) INFORMATION FOR SEQ ID NO:    343:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 343:

CCGAAUUCUU CACCG                                                    15

(2) INFORMATION FOR SEQ ID NO:    344:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 344:

GAAUUCUUCA CCGAA                                                    15

(2) INFORMATION FOR SEQ ID NO:    345:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 345:

AAUUCUUCAC CGAAU                                                    15

(2) INFORMATION FOR SEQ ID NO:    346:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 346:

```
ACCGAAUUGG ACGGG                                                      15

(2) INFORMATION FOR SEQ ID NO:   347:

(i) SEQUENCE CHARACTERISTICS:
        (A) LENGTH:           15
        (B) TYPE:             nucleic acid
        (C) STRANDEDNESS:     single
        (D) TOPOLOGY:         linear (xi) SEQUENCE DESCRIPTION: SEQ ID NO:   347:

GUGCGGUUGC ACAGG                                                      15

(2) INFORMATION FOR SEQ ID NO:   348:

(i) SEQUENCE CHARACTERISTICS:
        (A) LENGTH:           15
        (B) TYPE:             nucleic acid
        (C) STRANDEDNESS:     single
        (D) TOPOLOGY:         linear (xi) SEQUENCE DESCRIPTION: SEQ ID NO:  348:

CACAGGUACG CUCCG                                                      15

(2) INFORMATION FOR SEQ ID NO:   349:

(i) SEQUENCE CHARACTERISTICS:
        (A) LENGTH:           15
        (B) TYPE:             nucleic acid
        (C) STRANDEDNESS:     single
        (D) TOPOLOGY:         linear (xi) SEQUENCE DESCRIPTION: SEQ ID NO:   349:

GUACGCUCCG GCGUG                                                      15

(2) INFORMATION FOR SEQ ID NO:   350:

(i) SEQUENCE CHARACTERISTICS:
        (A) LENGTH:           15
        (B) TYPE:             nucleic acid
        (C) STRANDEDNESS:     single
        (D) TOPOLOGY:         linear (xi) SEQUENCE DESCRIPTION: SEQ ID NO:   350:

CAGACCUCUC CUACG                                                      15

(2) INFORMATION FOR SEQ ID NO:   351:

(i) SEQUENCE CHARACTERISTICS:
        (A) LENGTH:           15
        (B) TYPE:             nucleic acid
        (C) STRANDEDNESS:     single
        (D) TOPOLOGY:         linear (xi) SEQUENCE DESCRIPTION: SEQ ID NO:   351:

GACCUCUCCU ACGGG                                                      15

(2) INFORMATION FOR SEQ ID NO:   352:

(i) SEQUENCE CHARACTERISTICS:
        (A) LENGTH:           15
        (B) TYPE:             nucleic acid
        (C) STRANDEDNESS:     single
        (D) TOPOLOGY:         linear (xi) SEQUENCE DESCRIPTION: SEQ ID NO:   352:

CUCUCCUACG GGAGG                                                      15
```

```
(2) INFORMATION FOR SEQ ID NO:   353:

(i) SEQUENCE CHARACTERISTICS:
         (A) LENGTH:          15
         (B) TYPE:            nucleic acid
         (C) STRANDEDNESS:    single
         (D) TOPOLOGY:        linear (xi) SEQUENCE DESCRIPTION: SEQ ID NO: 353:

AGGAUGUCAC AUUCC                                                    15

(2) INFORMATION FOR SEQ ID NO:   354:

(i) SEQUENCE CHARACTERISTICS:
         (A) LENGTH:          15
         (B) TYPE:            nucleic acid
         (C) STRANDEDNESS:    single
         (D) TOPOLOGY:        linear (xi) SEQUENCE DESCRIPTION: SEQ ID NO: 354:

UCACAUUCCA GGUCG                                                    15

(2) INFORMATION FOR SEQ ID NO:   355:

(i) SEQUENCE CHARACTERISTICS:
         (A) LENGTH:          15
         (B) TYPE:            nucleic acid
         (C) STRANDEDNESS:    single
         (D) TOPOLOGY:        linear (xi) SEQUENCE DESCRIPTION: SEQ ID NO: 355:

UCCAGGUCGG GCUCA                                                    15

(2) INFORMATION FOR SEQ ID NO:   356:

(i) SEQUENCE CHARACTERISTICS:
         (A) LENGTH:          15
         (B) TYPE:            nucleic acid
         (C) STRANDEDNESS:    single
         (D) TOPOLOGY:        linear (xi) SEQUENCE DESCRIPTION: SEQ ID NO: 356:

UCGGGCUCAA CCAAU                                                    15

(2) INFORMATION FOR SEQ ID NO:   357:

(i) SEQUENCE CHARACTERISTICS:
         (A) LENGTH:          15
         (B) TYPE:            nucleic acid
         (C) STRANDEDNESS:    single
         (D) TOPOLOGY:        linear (xi) SEQUENCE DESCRIPTION: SEQ ID NO: 357:

AACCAAUACC UGGUU                                                    15

(2) INFORMATION FOR SEQ ID NO:   358:

(i) SEQUENCE CHARACTERISTICS:
         (A) LENGTH:          15
         (B) TYPE:            nucleic acid
         (C) STRANDEDNESS:    single
         (D) TOPOLOGY:        linear (xi) SEQUENCE DESCRIPTION: SEQ ID NO: 358:

ACCUGGUUGG GUCAC                                                    15
```

(2) INFORMATION FOR SEQ ID NO: 359:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 359:

GUUGGGUCAC AGCUC          15

(2) INFORMATION FOR SEQ ID NO: 360:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 360:

CACAGCUCCC AUGCG          15

(2) INFORMATION FOR SEQ ID NO: 361:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 361:

UAAACGUAGG CUGGC          15

(2) INFORMATION FOR SEQ ID NO: 362:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 362:

AGGGGGUCUC CCCCC          15

(2) INFORMATION FOR SEQ ID NO: 363:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 363:

GGGGUCUCCC CCCUC          15

(2) INFORMATION FOR SEQ ID NO: 364:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 364:

CCCCCCUCCU UGGCC          15

(2) INFORMATION FOR SEQ ID NO: 365:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 365:

CCCUCCUUGG CCAGC                                               15

(2) INFORMATION FOR SEQ ID NO: 366:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 366:

GCCAGCUCUU CAGCU                                               15

(2) INFORMATION FOR SEQ ID NO: 367:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 367:

AGCCAAUUGU CUGCG                                               15

(2) INFORMATION FOR SEQ ID NO: 368:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 368:

CAAUUGUCUG CGCCU                                               15

(2) INFORMATION FOR SEQ ID NO: 369:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 369:

CCAACCUCCU GUGGC                                               15

(2) INFORMATION FOR SEQ ID NO: 370:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 370:

ACCCGCUUCG AGCGG                                               15

(2) INFORMATION FOR SEQ ID NO: 371:

```
    (i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 371:

CCCGCUUCGA GCGGA                                                    15

(2) INFORMATION FOR SEQ ID NO: 372:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 372:

GGGAAGUAUC CGUUG                                                    15

(2) INFORMATION FOR SEQ ID NO: 373:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 373:

CCCGCGUUGC CAUA                                                     15

(2) INFORMATION FOR SEQ ID NO: 374:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 374:

UGCCCAUAUG GGCAC                                                    15

(2) INFORMATION FOR SEQ ID NO: 375:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 375:

CCCGGAUUAC AACCC                                                    15

(2) INFORMATION FOR SEQ ID NO: 376:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 376:

CCGGAUUACA ACCCU                                                    15

(2) INFORMATION FOR SEQ ID NO: 377:
```

(i) SEQUENCE CHARACTERISTICS:
      (A) LENGTH:        15
      (B) TYPE:          nucleic acid
      (C) STRANDEDNESS:  single
      (D) TOPOLOGY:      linear (xi) SEQUENCE DESCRIPTION: SEQ ID NO: 377:

CCACUGUUAG AGUCC                                                    15

(2) INFORMATION FOR SEQ ID NO: 378:

(i) SEQUENCE CHARACTERISTICS:
      (A) LENGTH:        15
      (B) TYPE:          nucleic acid
      (C) STRANDEDNESS:  single
      (D) TOPOLOGY:      linear (xi) SEQUENCE DESCRIPTION: SEQ ID NO: 378:

CACUGUUAGA GUCCU                                                    15

(2) INFORMATION FOR SEQ ID NO: 379:

(i) SEQUENCE CHARACTERISTICS:
      (A) LENGTH:        15
      (B) TYPE:          nucleic acid
      (C) STRANDEDNESS:  single
      (D) TOPOLOGY:      linear (xi) SEQUENCE DESCRIPTION: SEQ ID NO: 379:

GAAAAGUCCG GACUA                                                    15

(2) INFORMATION FOR SEQ ID NO: 380:

(i) SEQUENCE CHARACTERISTICS:
      (A) LENGTH:        15
      (B) TYPE:          nucleic acid
      (C) STRANDEDNESS:  single
      (D) TOPOLOGY:      linear (xi) SEQUENCE DESCRIPTION: SEQ ID NO: 380:

CCGGACUACG UCCCU                                                    15

(2) INFORMATION FOR SEQ ID NO: 381:

(i) SEQUENCE CHARACTERISTICS:
      (A) LENGTH:        15
      (B) TYPE:          nucleic acid
      (C) STRANDEDNESS:  single
      (D) TOPOLOGY:      linear (xi) SEQUENCE DESCRIPTION: SEQ ID NO: 381:

ACUACGUCCC UCCGG                                                    15

(2) INFORMATION FOR SEQ ID NO: 382:

(i) SEQUENCE CHARACTERISTICS:
      (A) LENGTH:        15
      (B) TYPE:          nucleic acid
      (C) STRANDEDNESS:  single
      (D) TOPOLOGY:      linear (xi) SEQUENCE DESCRIPTION: SEQ ID NO: 382:

CGUCCCUCCG GCGGU                                                    15

(2) INFORMATION FOR SEQ ID NO: 383:

(i) SEQUENCE CHARACTERISTICS:

(A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 383:

UGCCCAUUGC CGCCU                                                          15

(2) INFORMATION FOR SEQ ID NO:   384:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 384:

GCCGCCUACC ACGGG                                                          15

(2) INFORMATION FOR SEQ ID NO:   385:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 385:

ACAGAGUCCA CCGUG                                                          15

(2) INFORMATION FOR SEQ ID NO:   386:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 386:

GCUGGCUACU AAGAC                                                          15

(2) INFORMATION FOR SEQ ID NO:   387:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 387:

GGCUACUAAG ACUUU                                                          15

(2) INFORMATION FOR SEQ ID NO:   388:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 388:

UAAGACUUUC GGCAG                                                          15

(2) INFORMATION FOR SEQ ID NO:   389:

(i) SEQUENCE CHARACTERISTICS:
            (A) LENGTH:          15

(B) TYPE:           nucleic acid
            (C) STRANDEDNESS:   single
            (D) TOPOLOGY:       linear (xi) SEQUENCE DESCRIPTION: SEQ ID NO: 389:

AAGACUUUCG GCAGC                                                        15

(2) INFORMATION FOR SEQ ID NO:  390:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 390:

AGACUUUCGG CAGCU                                                        15

(2) INFORMATION FOR SEQ ID NO:  391:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 391:

UCCGGAUCGU CGGCC                                                        15

(2) INFORMATION FOR SEQ ID NO:  392:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 392:

GGAUCGUCGG CCGUU                                                        15

(2) INFORMATION FOR SEQ ID NO:  393:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 393:

CGGCCGUUGA CAGCG                                                        15

(2) INFORMATION FOR SEQ ID NO:  394:

(i) SEQUENCE CHARACTERISTICS:
            (A) LENGTH:         15
            (B) TYPE:           nucleic acid
            (C) STRANDEDNESS:   single
            (D) TOPOLOGY:       linear (xi) SEQUENCE DESCRIPTION: SEQ ID NO: 394:

UCGUACUCCU CCAUG                                                        15

(2) INFORMATION FOR SEQ ID NO:  395:

(i) SEQUENCE CHARACTERISTICS:
            (A) LENGTH:         15
            (B) TYPE:           nucleic acid

```
            (C) STRANDEDNESS:     single
            (D) TOPOLOGY:         linear (xi) SEQUENCE DESCRIPTION: SEQ ID NO: 395:

UACUCCUCCA UGCCC                                                    15

(2) INFORMATION FOR SEQ ID NO:  396:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 396:

CCCCCCUUGA GGGGG                                                    15

(2) INFORMATION FOR SEQ ID NO:  397:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 397:

CCCUGAUCUC AGCGA                                                    15

(2) INFORMATION FOR SEQ ID NO:  398:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 398:

CUGAUCUCAG CGACG                                                    15

(2) INFORMATION FOR SEQ ID NO:  399:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 399:

GACGGGUCUU GGUCU                                                    15

(2) INFORMATION FOR SEQ ID NO:  400:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 400:

CGGGUCUUGG UCUAC                                                    15

(2) INFORMATION FOR SEQ ID NO:  401:

(i) SEQUENCE CHARACTERISTICS:
            (A) LENGTH:          15
            (B) TYPE:            nucleic acid
            (C) STRANDEDNESS:    single
```

(D) TOPOLOGY:         linear (xi) SEQUENCE DESCRIPTION: SEQ ID NO: 401:

UCUUGGUCUA CCGUG                                                              15

(2) INFORMATION FOR SEQ ID NO:    402:

(i) SEQUENCE CHARACTERISTICS:
            (A) LENGTH:           15
            (B) TYPE:             nucleic acid
            (C) STRANDEDNESS:     single
            (D) TOPOLOGY:         linear (xi) SEQUENCE DESCRIPTION: SEQ ID NO: 402:

UUGGUCUACC GUGAG                                                              15

(2) INFORMATION FOR SEQ ID NO:    403:

(i) SEQUENCE CHARACTERISTICS:
            (A) LENGTH:           15
            (B) TYPE:             nucleic acid
            (C) STRANDEDNESS:     single
            (D) TOPOLOGY:         linear (xi) SEQUENCE DESCRIPTION: SEQ ID NO: 403:

ACGACAUCGU CUGCU                                                              15

(2) INFORMATION FOR SEQ ID NO:    404:

(i) SEQUENCE CHARACTERISTICS:
            (A) LENGTH:           15
            (B) TYPE:             nucleic acid
            (C) STRANDEDNESS:     single
            (D) TOPOLOGY:         linear (xi) SEQUENCE DESCRIPTION: SEQ ID NO: 404:

ACAUCGUCUG CUGCU                                                              15

(2) INFORMATION FOR SEQ ID NO:    405:

(i) SEQUENCE CHARACTERISTICS:
            (A) LENGTH:           15
            (B) TYPE:             nucleic acid
            (C) STRANDEDNESS:     single
            (D) TOPOLOGY:         linear (xi) SEQUENCE DESCRIPTION: SEQ ID NO: 405:

UGCUGCUCAA UGUCC                                                              15

(2) INFORMATION FOR SEQ ID NO:    406:

(i) SEQUENCE CHARACTERISTICS:
            (A) LENGTH:           15
            (B) TYPE:             nucleic acid
            (C) STRANDEDNESS:     single
            (D) TOPOLOGY:         linear (xi) SEQUENCE DESCRIPTION: SEQ ID NO: 406:

UCAAUGUCCU ACACA                                                              15

(2) INFORMATION FOR SEQ ID NO:    407:

(i) SEQUENCE CHARACTERISTICS:
            (A) LENGTH:           15
            (B) TYPE:             nucleic acid
            (C) STRANDEDNESS:     single
            (D) TOPOLOGY:         linear (xi) SEQUENCE DESCRIPTION: SEQ ID NO: 407:

UGCCCAUCAA CGCGU                                                                15

(2) INFORMATION FOR SEQ ID NO:    408:

(i) SEQUENCE CHARACTERISTICS:
          (A) LENGTH:          15
          (B) TYPE:            nucleic acid
          (C) STRANDEDNESS:    single
          (D) TOPOLOGY:        linear (xi) SEQUENCE DESCRIPTION: SEQ ID NO: 408:

ACAACAUCCC GCAGU                                                                15

(2) INFORMATION FOR SEQ ID NO:    409:

(i) SEQUENCE CHARACTERISTICS:
          (A) LENGTH:          15
          (B) TYPE:            nucleic acid
          (C) STRANDEDNESS:    single
          (D) TOPOLOGY:        linear (xi) SEQUENCE DESCRIPTION: SEQ ID NO: 409:

UGCAAGUCCU GGACG                                                                15

(2) INFORMATION FOR SEQ ID NO:    410:

(i) SEQUENCE CHARACTERISTICS:
          (A) LENGTH:          15
          (B) TYPE:            nucleic acid
          (C) STRANDEDNESS:    single
          (D) TOPOLOGY:        linear (xi) SEQUENCE DESCRIPTION: SEQ ID NO: 410:

GACCACUACC GGGAC                                                                15

(2) INFORMATION FOR SEQ ID NO:    411:

(i) SEQUENCE CHARACTERISTICS:
          (A) LENGTH:          15
          (B) TYPE:            nucleic acid
          (C) STRANDEDNESS:    single
          (D) TOPOLOGY:        linear (xi) SEQUENCE DESCRIPTION: SEQ ID NO: 411:

UAAGGCUAAA CUUCU                                                                15

(2) INFORMATION FOR SEQ ID NO:    412:

(i) SEQUENCE CHARACTERISTICS:
          (A) LENGTH:          15
          (B) TYPE:            nucleic acid
          (C) STRANDEDNESS:    single
          (D) TOPOLOGY:        linear (xi) SEQUENCE DESCRIPTION: SEQ ID NO: 412:

AACUUCUAUC CGUAG                                                                15

(2) INFORMATION FOR SEQ ID NO:    413:

(i) SEQUENCE CHARACTERISTICS:
          (A) LENGTH:          15
          (B) TYPE:            nucleic acid
          (C) STRANDEDNESS:    single
          (D) TOPOLOGY:        linear (xi) SEQUENCE DESCRIPTION: SEQ ID NO: 413:

CUUCUAUCCG UAGAA                                                15

(2) INFORMATION FOR SEQ ID NO: 414:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 414:

UAUCCGUAGA AGAAG                                                15

(2) INFORMATION FOR SEQ ID NO: 415:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 415:

GCCAAAUCUA AAUUU                                                15

(2) INFORMATION FOR SEQ ID NO: 416:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 416:

CAAAUCUAAA UUUGG                                                15

(2) INFORMATION FOR SEQ ID NO: 417:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 417:

UCUAAAUUUG GCUAU                                                15

(2) INFORMATION FOR SEQ ID NO: 418:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 418:

CUAAAUUUGG CUAUG                                                15

(2) INFORMATION FOR SEQ ID NO: 419:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 419:

UUUGGCUAUG GGGCA                                                               15

(2) INFORMATION FOR SEQ ID NO:    420:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO:    420:

ACCACAUCCG CUCCG                                                               15

(2) INFORMATION FOR SEQ ID NO:    421:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO:    421:

AUCCGCUCCG UGUGG                                                               15

(2) INFORMATION FOR SEQ ID NO:    422:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO:    422:

CUCGCCUUAU CGUAU                                                               15

(2) INFORMATION FOR SEQ ID NO:    423:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO:    423:

UCGCCUUAUC GUAUU                                                               15

(2) INFORMATION FOR SEQ ID NO:    424:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO:    424:

GCCUUAUCGU AUUCC                                                               15

(2) INFORMATION FOR SEQ ID NO:    425:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO:    425:

```
UCCUCGUACG GAUUC                                                    15
```

(2) INFORMATION FOR SEQ ID NO: 426:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 426:

```
UACGGAUUCC AGUAC                                                    15
```

(2) INFORMATION FOR SEQ ID NO: 427:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 427:

```
UUCCAGUACU CUCCU                                                    15
```

(2) INFORMATION FOR SEQ ID NO: 428:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 428:

```
GUACUCUCCU GGGCA                                                    15
```

(2) INFORMATION FOR SEQ ID NO: 429:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 429:

```
AGCGGGUUGA GUUCC                                                    15
```

(2) INFORMATION FOR SEQ ID NO: 430:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 430:

```
GUUGAGUUCC UGGUG                                                    15
```

(2) INFORMATION FOR SEQ ID NO: 431:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 431:

```
UUGAGUUCCU GGUGA                                                    15
```

(2) INFORMATION FOR SEQ ID NO: 432:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 432:

UGGAAAUCAA AGAAA                                        15

(2) INFORMATION FOR SEQ ID NO: 433:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 433:

AGGCCAUAAA GUCGC                                        15

(2) INFORMATION FOR SEQ ID NO: 434:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 434:

AUAAAGUCGC UCACG                                        15

(2) INFORMATION FOR SEQ ID NO: 435:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 435:

AGUCGCUCAC GGAGC                                        15

(2) INFORMATION FOR SEQ ID NO: 436:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 436:

AGCGGCUCUA CAUCG                                        15

(2) INFORMATION FOR SEQ ID NO: 437:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 437:

CGGCUCUACA UCGGG                                        15

(2) INFORMATION FOR SEQ ID NO: 438:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 438:

UCUACAUCGG GGGCC                                                    15

(2) INFORMATION FOR SEQ ID NO: 439:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 439:

CUGCGGUUAU CGCCG                                                    15

(2) INFORMATION FOR SEQ ID NO: 440:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 440:

UGCGGUUAUC GCCGG                                                    15

(2) INFORMATION FOR SEQ ID NO: 441:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 441:

CGGUUAUCGC CGGUG                                                    15

(2) INFORMATION FOR SEQ ID NO: 442:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 442:

GACGACUAGC UGCGG                                                    15

(2) INFORMATION FOR SEQ ID NO: 443:

(i) SEQUENCE CHARACTERISTICS:
        (A) LENGTH:        15
        (B) TYPE:          nucleic acid
        (C) STRANDEDNESS:  single
        (D) TOPOLOGY:      linear (xi) SEQUENCE DESCRIPTION: SEQ ID NO: 443:

GGCCUGUCGA GCUGC                                                    15

(2) INFORMATION FOR SEQ ID NO: 444:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 444:

CAAAGCUCCA GGACU                                                        15

(2) INFORMATION FOR SEQ ID NO: 445:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 445:

CGAUGCUCGU GAACG                                                        15

(2) INFORMATION FOR SEQ ID NO: 446:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 446:

ACGACCUUGU CGUUA                                                        15

(2) INFORMATION FOR SEQ ID NO: 447:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 447:

ACCUUGUCGU UAUCU                                                        15

(2) INFORMATION FOR SEQ ID NO: 448:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 448:

UUGUCGUUAU CUGUG                                                        15

(2) INFORMATION FOR SEQ ID NO: 449:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 449:

AGGUACUCUG CCCCC                                                        15

(2) INFORMATION FOR SEQ ID NO: 450:

```
        (i) SEQUENCE CHARACTERISTICS:
              (A) LENGTH:           15
              (B) TYPE:             nucleic acid
              (C) STRANDEDNESS:     single
              (D) TOPOLOGY:         linear (xi) SEQUENCE DESCRIPTION: SEQ ID NO: 450:

CCAGAAUACG ACUUG                                                            15

(2) INFORMATION FOR SEQ ID NO:    451:

(i) SEQUENCE CHARACTERISTICS:
              (A) LENGTH:           15
              (B) TYPE:             nucleic acid
              (C) STRANDEDNESS:     single
              (D) TOPOLOGY:         linear (xi) SEQUENCE DESCRIPTION: SEQ ID NO: 451:

UCAUGCUCCU CCAAC                                                            15

(2) INFORMATION FOR SEQ ID NO:    452:

(i) SEQUENCE CHARACTERISTICS:
              (A) LENGTH:           15
              (B) TYPE:             nucleic acid
              (C) STRANDEDNESS:     single
              (D) TOPOLOGY:         linear (xi) SEQUENCE DESCRIPTION: SEQ ID NO: 452:

UGCUCCUCCA ACGUG                                                            15

(2) INFORMATION FOR SEQ ID NO:    453:

(i) SEQUENCE CHARACTERISTICS:
              (A) LENGTH:           15
              (B) TYPE:             nucleic acid
              (C) STRANDEDNESS:     single
              (D) TOPOLOGY:         linear (xi) SEQUENCE DESCRIPTION: SEQ ID NO: 453:

GACGCAUCCG GCAAA                                                            15

(2) INFORMATION FOR SEQ ID NO:    454:

(i) SEQUENCE CHARACTERISTICS:
              (A) LENGTH:           15
              (B) TYPE:             nucleic acid
              (C) STRANDEDNESS:     single
              (D) TOPOLOGY:         linear (xi) SEQUENCE DESCRIPTION: SEQ ID NO: 454:

CCCCCCUUGC ACGGG                                                            15

(2) INFORMATION FOR SEQ ID NO:    455:

(i) SEQUENCE CHARACTERISTICS:
              (A) LENGTH:           15
              (B) TYPE:             nucleic acid
              (C) STRANDEDNESS:     single
              (D) TOPOLOGY:         linear (xi) SEQUENCE DESCRIPTION: SEQ ID NO: 455:

AUCAUGUAUG CGCCC                                                            15

(2) INFORMATION FOR SEQ ID NO:    456:
```

```
            (i) SEQUENCE CHARACTERISTICS:
                  (A) LENGTH:          15
                  (B) TYPE:            nucleic acid
                  (C) STRANDEDNESS:    single
                  (D) TOPOLOGY:        linear (xi) SEQUENCE DESCRIPTION: SEQ ID NO: 456:

CCCACCUUAU GGGCA                                                      15

(2) INFORMATION FOR SEQ ID NO:  457:

(i) SEQUENCE CHARACTERISTICS:
                  (A) LENGTH:          15
                  (B) TYPE:            nucleic acid
                  (C) STRANDEDNESS:    single
                  (D) TOPOLOGY:        linear (xi) SEQUENCE DESCRIPTION: SEQ ID NO: 457:

CCACCUUAUG GGCAA                                                      15

(2) INFORMATION FOR SEQ ID NO:  458:

(i) SEQUENCE CHARACTERISTICS:
                  (A) LENGTH:          15
                  (B) TYPE:            nucleic acid
                  (C) STRANDEDNESS:    single
                  (D) TOPOLOGY:        linear (xi) SEQUENCE DESCRIPTION: SEQ ID NO: 458:

GAUGAUUUUG AUGAC                                                      15

(2) INFORMATION FOR SEQ ID NO:  459:

(i) SEQUENCE CHARACTERISTICS:
                  (A) LENGTH:          15
                  (B) TYPE:            nucleic acid
                  (C) STRANDEDNESS:    single
                  (D) TOPOLOGY:        linear (xi) SEQUENCE DESCRIPTION: SEQ ID NO: 459:

GAUGACUCAC UUCUU                                                      15

(2) INFORMATION FOR SEQ ID NO:  460:

(i) SEQUENCE CHARACTERISTICS:
                  (A) LENGTH:          15
                  (B) TYPE:            nucleic acid
                  (C) STRANDEDNESS:    single
                  (D) TOPOLOGY:        linear (xi) SEQUENCE DESCRIPTION: SEQ ID NO: 460:

CCUGGAUUGU CAGAU                                                      15

(2) INFORMATION FOR SEQ ID NO:  461:

(i) SEQUENCE CHARACTERISTICS:
                  (A) LENGTH:          15
                  (B) TYPE:            nucleic acid
                  (C) STRANDEDNESS:    single
                  (D) TOPOLOGY:        linear (xi) SEQUENCE DESCRIPTION: SEQ ID NO: 461:

GGAUUGUCAG AUCUA                                                      15

(2) INFORMATION FOR SEQ ID NO:  462:

(i) SEQUENCE CHARACTERISTICS:
```

-continued

```
          (A) LENGTH:          15
          (B) TYPE:            nucleic acid
          (C) STRANDEDNESS:    single
          (D) TOPOLOGY:        linear (xi) SEQUENCE DESCRIPTION: SEQ ID NO: 462:

GUCAGAUCUA CGGGG                                                    15

(2) INFORMATION FOR SEQ ID NO:   463:

(i) SEQUENCE CHARACTERISTICS:
          (A) LENGTH:          15
          (B) TYPE:            nucleic acid
          (C) STRANDEDNESS:    single
          (D) TOPOLOGY:        linear (xi) SEQUENCE DESCRIPTION: SEQ ID NO: 463:

CAGAUCUACG GGGCC                                                    15

(2) INFORMATION FOR SEQ ID NO:   464:

(i) SEQUENCE CHARACTERISTICS:
          (A) LENGTH:          15
          (B) TYPE:            nucleic acid
          (C) STRANDEDNESS:    single
          (D) TOPOLOGY:        linear (xi) SEQUENCE DESCRIPTION: SEQ ID NO: 464:

CAUGCCUCAG GAAAC                                                    15

(2) INFORMATION FOR SEQ ID NO:   465:

(i) SEQUENCE CHARACTERISTICS:
          (A) LENGTH:          15
          (B) TYPE:            nucleic acid
          (C) STRANDEDNESS:    single
          (D) TOPOLOGY:        linear (xi) SEQUENCE DESCRIPTION: SEQ ID NO: 465:

GGAAACUUGG GGUAC                                                    15

(2) INFORMATION FOR SEQ ID NO:   466:

(i) SEQUENCE CHARACTERISTICS:
          (A) LENGTH:          15
          (B) TYPE:            nucleic acid
          (C) STRANDEDNESS:    single
          (D) TOPOLOGY:        linear (xi) SEQUENCE DESCRIPTION: SEQ ID NO: 466:

UUGGGGUACC GCCCU                                                    15

(2) INFORMATION FOR SEQ ID NO:   467:

(i) SEQUENCE CHARACTERISTICS:
          (A) LENGTH:          15
          (B) TYPE:            nucleic acid
          (C) STRANDEDNESS:    single
          (D) TOPOLOGY:        linear (xi) SEQUENCE DESCRIPTION: SEQ ID NO: 467:

CCGCCCUUGC GAGUC                                                    15

(2) INFORMATION FOR SEQ ID NO:   468:

(i) SEQUENCE CHARACTERISTICS:
          (A) LENGTH:          15
```

```
            (B) TYPE:            nucleic acid
            (C) STRANDEDNESS:    single
            (D) TOPOLOGY:        linear (xi) SEQUENCE DESCRIPTION: SEQ ID NO: 468:

UGCGAGUCUG GAGAC                                                         15

(2) INFORMATION FOR SEQ ID NO:  469:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 469:

GAAGUGUCCG CGCUA                                                         15

(2) INFORMATION FOR SEQ ID NO:  470:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 470:

CCGCGCUAGG CUACU                                                         15

(2) INFORMATION FOR SEQ ID NO:  471:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 471:

CUAGGCUACU GUCCC                                                         15

(2) INFORMATION FOR SEQ ID NO:  472:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 472:

CUACUGUCCC AAGGG                                                         15

(2) INFORMATION FOR SEQ ID NO:  473:

(i) SEQUENCE CHARACTERISTICS:
            (A) LENGTH:          15
            (B) TYPE:            nucleic acid
            (C) STRANDEDNESS:    single
            (D) TOPOLOGY:        linear (xi) SEQUENCE DESCRIPTION: SEQ ID NO: 473:

GCCGCGUCCC AGCUG                                                         15

(2) INFORMATION FOR SEQ ID NO:  474:

(i) SEQUENCE CHARACTERISTICS:
            (A) LENGTH:          15
            (B) TYPE:            nucleic acid
```

```
        (C) STRANDEDNESS:    single
        (D) TOPOLOGY:        linear (xi) SEQUENCE DESCRIPTION: SEQ ID NO: 474:

CUGGACUUGU CCAGC                                                       15

(2) INFORMATION FOR SEQ ID NO:   475:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 475:

GACUUGUCCA GCUGG                                                       15

(2) INFORMATION FOR SEQ ID NO:   476:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 476:

AGCUGGUUCG UUGCU                                                       15

(2) INFORMATION FOR SEQ ID NO:   477:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 477:

GCUGGUUCGU UGCUG                                                       15

(2) INFORMATION FOR SEQ ID NO:   478:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 478:

GGUUCGUUGC UGGUU                                                       15

(2) INFORMATION FOR SEQ ID NO:   479:

(i) SEQUENCE CHARACTERISTICS:
        (A) LENGTH:          15
        (B) TYPE:            nucleic acid
        (C) STRANDEDNESS:    single
        (D) TOPOLOGY:        linear (xi) SEQUENCE DESCRIPTION: SEQ ID NO: 479:

GAGACAUAUA UCACA                                                       15

(2) INFORMATION FOR SEQ ID NO:   480:

(i) SEQUENCE CHARACTERISTICS:
        (A) LENGTH:          15
        (B) TYPE:            nucleic acid
        (C) STRANDEDNESS:    single
```

-continued (D) TOPOLOGY:        linear (xi) SEQUENCE DESCRIPTION: SEQ ID NO: 480:

GACAUAUAUC ACAGC                                                            15

(2) INFORMATION FOR SEQ ID NO: 481:

(i) SEQUENCE CHARACTERISTICS:
                    (A) LENGTH:          15
                    (B) TYPE:            nucleic acid
                    (C) STRANDEDNESS:    single
                    (D) TOPOLOGY:        linear (xi) SEQUENCE DESCRIPTION: SEQ ID NO: 481:

CAUAUAUCAC AGCCU                                                            15

(2) INFORMATION FOR SEQ ID NO: 482:

(i) SEQUENCE CHARACTERISTICS:
                    (A) LENGTH:          15
                    (B) TYPE:            nucleic acid
                    (C) STRANDEDNESS:    single
                    (D) TOPOLOGY:        linear (xi) SEQUENCE DESCRIPTION: SEQ ID NO: 482:

AGCCUGUCUC GUGCC                                                            15

(2) INFORMATION FOR SEQ ID NO: 483:

(i) SEQUENCE CHARACTERISTICS:
                    (A) LENGTH:          15
                    (B) TYPE:            nucleic acid
                    (C) STRANDEDNESS:    single
                    (D) TOPOLOGY:        linear (xi) SEQUENCE DESCRIPTION: SEQ ID NO: 483:

GGUGCCUACU CCUAC                                                            15

(2) INFORMATION FOR SEQ ID NO: 484:

(i) SEQUENCE CHARACTERISTICS:
                    (A) LENGTH:          15
                    (B) TYPE:            nucleic acid
                    (C) STRANDEDNESS:    single
                    (D) TOPOLOGY:        linear (xi) SEQUENCE DESCRIPTION: SEQ ID NO: 484:

GCCUACUCCU ACUUU                                                            15

(2) INFORMATION FOR SEQ ID NO: 485:

(i) SEQUENCE CHARACTERISTICS:
                    (A) LENGTH:          15
                    (B) TYPE:            nucleic acid
                    (C) STRANDEDNESS:    single
                    (D) TOPOLOGY:        linear (xi) SEQUENCE DESCRIPTION: SEQ ID NO: 485:

UACUCCUACU UUCCG                                                            15

(2) INFORMATION FOR SEQ ID NO: 486:

(i) SEQUENCE CHARACTERISTICS:
                    (A) LENGTH:          15
                    (B) TYPE:            nucleic acid
                    (C) STRANDEDNESS:    single
                    (D) TOPOLOGY:        linear (xi) SEQUENCE DESCRIPTION: SEQ ID NO: 486:

UCCUACUUUC CGUAG                                                                  15

(2) INFORMATION FOR SEQ ID NO:  487:

(i) SEQUENCE CHARACTERISTICS:
             (A) LENGTH:          15
             (B) TYPE:            nucleic acid
             (C) STRANDEDNESS:    single
             (D) TOPOLOGY:        linear (xi) SEQUENCE DESCRIPTION: SEQ ID NO: 487:

CCUACUUUCC GUAGG                                                                  15

(2) INFORMATION FOR SEQ ID NO:  488:

(i) SEQUENCE CHARACTERISTICS:
             (A) LENGTH:          15
             (B) TYPE:            nucleic acid
             (C) STRANDEDNESS:    single
             (D) TOPOLOGY:        linear (xi) SEQUENCE DESCRIPTION: SEQ ID NO: 488:

CUACUUUCCG UAGGG                                                                  15

(2) INFORMATION FOR SEQ ID NO:  489:

(i) SEQUENCE CHARACTERISTICS:
             (A) LENGTH:          15
             (B) TYPE:            nucleic acid
             (C) STRANDEDNESS:    single
             (D) TOPOLOGY:        linear (xi) SEQUENCE DESCRIPTION: SEQ ID NO: 489:

UUUCCGUAGG GGUAG                                                                  15

(2) INFORMATION FOR SEQ ID NO:  490:

(i) SEQUENCE CHARACTERISTICS:
             (A) LENGTH:          15
             (B) TYPE:            nucleic acid
             (C) STRANDEDNESS:    single
             (D) TOPOLOGY:        linear (xi) SEQUENCE DESCRIPTION: SEQ ID NO: 490:

UAGGGGUAGG CAUCU                                                                  15

(2) INFORMATION FOR SEQ ID NO:  491:

(i) SEQUENCE CHARACTERISTICS:
             (A) LENGTH:          15
             (B) TYPE:            nucleic acid
             (C) STRANDEDNESS:    single
             (D) TOPOLOGY:        linear (xi) SEQUENCE DESCRIPTION: SEQ ID NO: 491:

UAGGCAUCUA CCUGC                                                                  15

(2) INFORMATION FOR SEQ ID NO:  492:

(i) SEQUENCE CHARACTERISTICS:
             (A) LENGTH:          15
             (B) TYPE:            nucleic acid
             (C) STRANDEDNESS:    single
             (D) TOPOLOGY:        linear (xi) SEQUENCE DESCRIPTION: SEQ ID NO: 492:

GGCAUCUACC UGCUC                                                      15

(2) INFORMATION FOR SEQ ID NO: 493:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 493:

ACCUGCUCCC CAACC                                                      15

(2) INFORMATION FOR SEQ ID NO: 494:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 494:

GGGAGCUAAU CACUC                                                      15

(2) INFORMATION FOR SEQ ID NO: 495:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 495:

AGCUAAUCAC UCCAG                                                      15

(2) INFORMATION FOR SEQ ID NO: 496:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 496:

AAUCACUCCA GGCCA                                                      15

(2) INFORMATION FOR SEQ ID NO: 497:

(i) SEQUENCE CHARACTERISTICS:
        (A) LENGTH:         15
        (B) TYPE:           nucleic acid
        (C) STRANDEDNESS:   single
        (D) TOPOLOGY:       linear (xi) SEQUENCE DESCRIPTION: SEQ ID NO: 497:

GGCCAAUAGG CCAUC                                                      15

(2) INFORMATION FOR SEQ ID NO: 498:

(i) SEQUENCE CHARACTERISTICS:
        (A) LENGTH:         32
        (B) TYPE:           nucleic acid
        (C) STRANDEDNESS:   single
        (D) TOPOLOGY:       linear (ix) FEATURE:

-continued (D) OTHER INFORMATION: "N" stands for any base.

(xi) SEQUENCE DESCRIPTION: SEQ ID NO: 498:

NNNNNCUGAN GAGGCCGAAAGGCC GAAANNNN                                               32